US007452543B2

(12) United States Patent
Chaddock et al.

(10) Patent No.: US 7,452,543 B2
(45) Date of Patent: Nov. 18, 2008

(54) CONJUGATES OF GALACTOSE-BINDING LECTINS AND CLOSTRIDIAL NEUROTOXINS AS ANALGESICS

(75) Inventors: John Andrew Chaddock, Salisbury (GB); Philip Marks, Salisbury (GB); Michael John Duggan, Salisbury (GB)

(73) Assignee: Syntaxin Ltd. (GB)

( * ) Notice: Subject to any disclaimer, the term of this patent is extended or adjusted under 35 U.S.C. 154(b) by 0 days.

(21) Appl. No.: 11/257,500

(22) Filed: Oct. 25, 2005

(65) Prior Publication Data

US 2006/0121056 A1    Jun. 8, 2006

Related U.S. Application Data

(63) Continuation-in-part of application No. 09/529,130, filed as application No. PCT/GB98/03001 on Oct. 7, 1998, now Pat. No. 7,052,702.

(30) Foreign Application Priority Data

Oct. 8, 1997    (GB)    ................................. 9721189.0

(51) Int. Cl.
*A61K 39/68* (2006.01)
*C07K 14/00* (2006.01)

(52) U.S. Cl. .............. 424/239.1; 424/236.1; 424/183.1; 424/194.1; 424/94.67; 530/350; 530/396; 514/2; 514/12; 435/252.7; 435/320.1; 435/69.1

(58) Field of Classification Search .............. 424/239.1, 424/236.1, 183.1, 194.1, 94.67; 530/350, 530/396; 514/2, 12; 435/252.7, 320.1, 69.1
See application file for complete search history.

(56) References Cited

U.S. PATENT DOCUMENTS

| | | | |
|---|---|---|---|
| 5,433,946 A | 7/1995 | Allen, Jr. et al. | |
| 5,668,255 A | 9/1997 | Murphy | |
| 5,989,545 A * | 11/1999 | Foster et al. ............. | 424/183.1 |
| 6,235,313 B1 | 5/2001 | Mathiowitz et al. | |
| 6,395,513 B1 | 5/2002 | Foster et al. | |
| 6,461,617 B1 | 10/2002 | Shone et al. | |
| 6,632,440 B1 | 10/2003 | Quinn et al. | |
| 7,052,702 B1 * | 5/2006 | Duggan et al. ........... | 424/239.1 |
| 2003/0049264 A1 | 3/2003 | Foster et al. | |
| 2003/0147895 A1 | 8/2003 | Shone et al. | |
| 2003/0166238 A1 | 9/2003 | Shone et al. | |
| 2004/0071736 A1 | 4/2004 | Quinn et al. | |
| 2005/0244435 A1 | 11/2005 | Shone et al. | |
| 2005/0255093 A1 | 11/2005 | Shone et al. | |

FOREIGN PATENT DOCUMENTS

| | | |
|---|---|---|
| DE | 197 35 105 A1 | 3/1999 |
| EP | 0 602 686 A2 | 6/1994 |
| WO | WO 91/09871 | 7/1991 |
| WO | WO 92/15327 | 9/1992 |
| WO | WO 93/04191 | 3/1993 |
| WO | WO 93/15766 | 8/1993 |
| WO | WO 94/21300 | 9/1994 |
| WO | WO 94/28923 | 12/1994 |
| WO | WO 95/32738 | 12/1995 |
| WO | WO 96/12802 | 5/1996 |
| WO | WO 96/33273 | 10/1996 |
| WO | WO 97/18790 | 5/1997 |
| WO | WO 98/07864 | 2/1998 |
| WO | WO 98/08540 | 3/1998 |
| WO | WO 00/57897 | 10/2000 |

OTHER PUBLICATIONS

Abstract of Adar, R., et al., "The amino acid sequence of *Erythrina corallodendron* lectin and its homology with other legume lectins," *FEBS Lett.* 257:81-85, Elsevier B.V. (1989), PubMed ID 2806566.

Abstract of Arango, R., et al., "Cloning and sequence analysis of the *Erythrina corallodendron* lectin cDNA," *FEBS Lett.* 264:109-111, Elsevier B.V. (1990), PubMed ID 1692539.

Abstract of Arango, R., et al., "Expression of *Erythrina corallodendron* lectin in *Escherichia coli*," *Eur. J. Biochem.* 205:575-581, The Federation of European Biochemical Societies and Blackwell Publishing (1992), PubMed ID 1572358.

Abstract of Arora, N., et al., "Cytotoxic effects of a chimeric protein consisting of tetanus toxin light chain and anthrax toxin lethal factor in non-neuronal cells," *J. Biol. Chem.* 269:26165-26171, The American Society for Biochemistry and Molecular Biology, Inc. (1994), PubMed ID 7929330.

Abstract of Brinkmann, U., et al., "A recombinant immunotoxin containing a disulfide-stablilized Fv fragment," *Proc. Natl. Acad. Sci. USA* 90:7538-7542, The National Academy of Sciences (1993), PubMed ID 8356052.

Abstract of Lamb, F.I., et al., "Nucleotide sequence of cloned cDNA coding for preproricin," *Eur. J. Biochem.* 148:265-270, The Federation of European Biochemical Societies and Blackwell Publishing (1985), PubMed ID 3838723.

Abstract of Lorberboum-Galski, H., et al., "Cytotoxic activity of an interleukin 2-Pseudomonas exotoxi chimeric protein produced in *Escherichia coli*," *Proc. Natl. Acad. Sci. USA* 85:1922-1926, The National Academy of Sciences, (1998), PubMed ID 3126499.

(Continued)

*Primary Examiner*—Chih-Min Kam
(74) *Attorney, Agent, or Firm*—Morris, Manning & Martin, LLP; Christopher W. Raimund

(57) ABSTRACT

A class of novel agents that are able to modify nociceptive afferent function is provided. The agents may inhibit the release of neurotransmitters from discrete populations of neurones and thereby reduce or preferably prevent the transmission of afferent pain signals from peripheral to central pain fibers. They comprise a galactose-binding lectin linked to a derivative of a clostridial neurotoxin. The derivative of the clostridial neurotoxin comprises the L-chain, or a fragment thereof, which includes the active proteolytic enzyme domain of the light (L) chain, linked to a molecule or domain with membrane translocating activity. The agents may be used in or as pharmaceuticals for the treatment of pain, particular chronic pain.

8 Claims, 14 Drawing Sheets

OTHER PUBLICATIONS

Abstract of Murphy, J.R., "Diphtheria-related peptide hormone gene fusions: a molecular genetic approach to chimeric toxin development," *Cancer Treat. Res.* 37:123-140, Springer (1988), PubMed ID 2908622.

Abstract of O'Hare, M., et al., "Cytotoxicity of a recombinant ricin-A-chain fusion protein containing a proteolytically-cleavable spacer sequence," *FEBS Lett.* 273:200-204, Elsevier B.V. (1990), PubMed ID 2121540.

Abstract of Plank, C., et al., "The influence of endosome-disruptive peptides on gene transfer using synthetic virus-like gene transfer systems," *J. Biol. Chem.* 269:12918-12924, The American Society for Biochemistry and Molecular Biology, Inc. (1994), PubMed ID 8175709.

Abstract of Williams, D.P., et al., "Diphtheria toxin receptor binding domain substitution with interleukin-2: genetic construction and properties of a diphtheria toxin-related interleukin-2 fusion protein," *Protein Eng.* 1:493-498, Oxford University Press (1987), PubMed ID 3334101.

Abstract of Wood, K.A., et al., "Preproabrin: genomic cloning, characterization and the expression of the A-chain in *Esherichia coli*," *Eur. J. Biochem.* 198:723-732, The Federation of European Biochemical Societies and Blackwell Publishing (1991), PubMed ID 2050149.

Abstract of Yamaguchi, O., et al., "Chemical structures of two subunits, A-subunit and B-subunit, of galactose-specific isoelectins from *Erythrina variegata* seeds," *J. Biochem.* (Tokyo) 114:560-566, Oxford University Press (1993), PubMed ID 8276768.

Bizzini, B., "Investigation of the Mode of Action of Tetanus Toxin With the Aid of Hybrid Molecules Consisting in Part of Tetanus Toxin-Derived Fragments," in *Bacterial Protein Toxins*, pp. 427-434, Academic Press London (1984).

Kurazono, H., et al., "Minimal Essential Domains Specifying Toxicity of the Light Chains of Tetanus Toxin and Botulinum Neurotoxin Type A," *J. Biol. Chem.* 267:14721-14729, The American Society for Biochemistry and Molecular Biology, Inc. (1992).

Law, I.J., et al., "Cloning and expression of cDNA for galactose-binding lectin from peanut nodules," *Plant Sci.* 115:71-79, Elsevier Science Ireland Ltd. (Mar. 1996).

Nathan, S. and Halina, L., "Legume lectins—a large family of homologous proteins," *FASEB J.* 4:3198-3208, The Federation of American Societies for Experimental Biology (1990).

"NeuroBloc (Botulinum Toxin Type B) For Cervical Dystonia Launched in UK," Doctor's Guide, P/S/L Consulting Group Inc. (Mar. 2001), visited online at http://www.pslgroup.com/dg/1F4216.htm on Nov. 28, 2001.

Streit, W.J., et al., "Histochemical Localization of Galactose-Containing Glycoconjugates in Sensory Neurons and Their Processes in the Central and Peripheral Nervous System of the Rat," *J. Histochem. Cytochem.* 33:1042-1052, The Histochemical Society (1985).

Van Damme, E.J.M., et al., "Molecular cloning of the bark and seed lectins from the Japanese pagoda tree (*Sophora japonica*)," *Plant Mol. Biol.* 33:523-536, Kluwer Academic Publishers (Feb. 1997).

Black, J.D., and Dolly, J.O., "Interaction of [125]Labeled Botulinum Neurotoxins with Nerve Terminals. I. Ultrastructural Autoradiographic Localization and Quantitation of Distinct Membrane Acceptors for Types A and B on Motor Nerves," *J. Cell Biol.* 103:521-534, The Rockefeller University Press (1986).

Blaustein, R.O., et al., "The N-terminal half of the heavy chain of botulinum type A neurotoxin forms channels in planar phospholipid bilayers," *FEBS Letts.* 226:115-120, Elsevier Science Publishers B.V. (1987).

Shone, C.C., et al., "Inactivation of *Clostridium botulinum* type A neurotoxin by trypsin and purification of two tryptic fragments. Proteolytic action near the COOH-terminus of the heavy subunit destroys toxin-binding activity," *Eur. J. Biochem.* 151:75-82, Springer International (1985).

Shone, C.C., et al., "A 50-kDa fragment from the $NH_2$-terminus of the heavy subunit of *Clostridium botulinum* type A neurotoxin forms channels in lipid vesicles," *Eur. J. Biochem.* 167:175-180, Springer International (1987).

Sutton, J.M., et al., "Tyrosine-1290 of tetanus neurotoxin plays a key role in its binding to gangliosides and functional binding to neurones," *FEBS Letts.* 493:45-49, Elsevier Science B.V. (Mar. 2001).

Yamazaki, N., et al., "Endogenous lectins as targets for drug delivery," *Advanced Drug Delivery Reviews* 43:225-244, Elsevier Science B.V. (Sep. 2000).

Dialog File 351, WPI Accession No. 1999-168079/199915, Derwent WPI English language abstract for DE 197 35 105 A1 (document AO3).

Diaz, A. and Dickenson, A.H., "Blockade of spinal N- and P-type, but not L-type, calcium channels inhibits the excitability of rat dorsal horn neurones produced by subcutaneous formalin inflammation," *Pain* 69:93-100, Elsevier Science Ireland Ltd. (Jan. 1997).

Edmonds, B.T. and Koenig, E., "Transmembrane Cytoskeletal Modulation in Preterminal Growing Axons: I. Arrest of Bulk and Organelle Transport in Goldfish Retinal Ganglion Cell Axons Regenerating In Vitro by Lectins Binding to Sialoglycoconjugates," *Cell Motil. Cytoskeleton* 17:106-117, Wiley-Liss, Inc. (1990).

Edmonds, B.T. and Koenig, E., "Transmembrane cytoskeletal modulation in preterminal growing axons. II. *Limax flavus* agglutinin-induced receptor redistribution, capping and internalization in varicosities of growing axons," *J. Neurocytol.* 20:232-247, Chapman and Hall Ltd. (1991).

Garber, N., et al., "On the specificity of the D-galactose-binding lectin (PA-I) of *Pseudomonas aeruginosa* and its strong binding to hydrophobic derivatives of D-galactose and thiogalactose," *Biochim. Et Biophys. Acta* 1116:331-333, Elsevier Science Publishers B.V. (1992).

Garret, C., et al., "Pharmacological properties of a potent and selective nonpeptide substance P antagonist," *Proc. Natl. Acad. Sci. USA* 88:10208-10212, National Academy of Sciences (1991).

Gupta, D., et al., "Differences in the Cross-Linking Activities of Native and Recombinant *Erythrina corallodendron* Lectin with Asialofetuin. Evidence for Carbohydrate-Carbohydrate Interactions in Lectin-Glycoprotein Complexes," *Biochem.* 33:2503-2508, American Chemical Society (1994).

Heilman, R.D., et al., "An Evaluation of the Hot Plate Technique to Study Narcotic Antagonists," *Res. Commun. Chem. Pathol. Pharmacol.* 13:635-647, PJD Publications Ltd. (1976).

Iglesias, J.L., et al., "Purification and Properties of a D-Galactose/N-Acetyl-D-galactosamine-Specific Lectin from *Erythrina cristagalli*," *Eur. J. Biochem.* 123:247-252, Blackwell Science Ltd. (1982).

Lembeck, F. and Holzer, P., "Substance P as Neurogenic Mediator of Antidromic Vasodilation and Neurogenic Plasma Extravasation," *Naunyn-Schmied. Arch. Pharmacol.* 310:175-183, Springer-Verlag (1979).

Lis, H. and Sharon, N., "Lectins as Molecules and as Tools," *Ann. Rev. Biochem.* 55:35-67, Annual Reviews, Inc. (1986).

Pintér, E., et al., "Lack of evidence for tachykinin $NK_1$ receptor-mediated neutrophil accumulation in the rat cutaneous microvasculature by thermal injury," *Eur. J. Pharmacol.* 369:91-98, Elsevier Science B.V. (Mar. 1999).

Silverman, J.D. and Kruger, L., "Selective neuronal glycoconjugate expression in sensory and autonomic ganglia: relation of lectin reactivity to peptide and enzyme markers," *J. Neurocytol.* 19:789-801, Chapman and Hall Ltd. (1990).

Sharon, N. and Lis, H., "Legume lectins—a large family of homologous proteins," *FASEB J.* 4:3198-3208, The Federation of American Societies for Experimental Biology (1990).

Welch, M. and Foster, K., "Chapter 26. Cell Culture of Neurons of the Peripheral Nervous System of Birds and Mammals," in: *The Neuron in Tissue Culture*, Haynes, L.W., ed., John Wiley & Sons Ltd., New York, N.Y. pp. 389-393 (Dec. 1999).

Zambenedetti, P., et al., "Identification of lectin binding sites in the rat brain," *Glycoconj. J.* 13:341-346, Chapman & Hall (Jun. 1996).

Zhou, L., et al., "Expression and Purification of the Light Chain of Botulinum Neurotoxin A: A Single Mutation Abolishes Its Cleavage of SNAP-25 and Neurotoxicity after Reconstitution with the Heavy Chain," *Biochem.* 34:15175-15181, American Chemical Society (1995).

Esp@cenet Database 12, English language abstract of European Patent No. 0 602 686 A2 (Document AL3).

Office Communication for U.S. Appl. No. 09/937,484, 12 pages, United States Patent and Trademark Office (mailed Jan. 29, 2004).

Reply to Restriction Requirement for U.S. Appl. No. 09/937,484, 4 pages (filed Feb. 27, 2004).

Office Communication for U.S. Appl. No. 09/937,484, 16 pages, United States Patent and Trademark Office (mailed Jun. 21, 2004).

Petition to the Director Under 37 C.F.R. §§ 1.144 and 1.181 to Withdraw Final Restriction Requirement for U.S. Appl. No. 09/937,484, 14 pages, (filed Aug. 17, 2004).

Amendment and Reply Under 37 C.F.R. § 1.111 for U.S. Appl. No. 09/937,484, 25 pages with Exhibits A-D (filed Sep. 21, 2004).

Prosecution History for U.S. Appl. No. 09/255,829, Shone et al., filed Feb. 23, 1999, now U.S. Patent No. 6,461,617.

Prosecution History for U.S. Appl. No. 09/763,669, Quinn et al., §371 filing date May 29, 2001, now U.S. Patent No. 6,632,440.

Prosecution History for U.S. Appl. No. 09/831,050, Shone et al., 0371 filing date Aug. 20, 2001.

Prosecution History for U.S. Appl. No. 10/130,973, Shone et al., 0371 filing date Jun. 25, 2002, now published as U.S. Application Publication No. 2003/0147895 A1.

Prosecution History for U.S. Appl. No. 10/241,596, Shone et al., filed Sep. 12, 2002, now published as U.S. Application Publication No. 2003/0166238 A1.

Prosecution History for U.S. Appl. No. 10/633,698, Quinn et al., filed Aug. 5, 2003, now published as U.S. Application Publication No. 2004/0071736 A1.

Co-pending U.S. Appl. No. 10/527,411, Shone et al., filed Mar. 11, 2005.

Curriculum vitae for Foster, K.A., General Project Manager at the Centre for Applied Microbiology & Research, 4 pages and Biographical Sketch for Chaddock, J.A., Senior Scientist at the Centre for Applied Microbiology & Research, 2 pages.

Hermanson, G.T., "Detailed Contents," in *Bioconjugate Techniques*, 1st Ed., 14 pages, Academic Press, Inc. (Jan. 1996).

International Search Report for International Application No. PCT/GB98/03001, European Patent Office, Netherlands, mailed Feb. 9, 1999.

Peeters, J.M., et al., "Comparison of four bifunctional reagents for coupling peptides to proteins and the effect of the three moieties on the immunogenicity of the conjugates," *J. Immunol. Meth. 120*:133-143, Elsevier Science Publishers B.V. (1989).

Thorpe, P.E., et al., New Coupling Agents for the Synthesis of Immunotoxins Containing a Hindered Disulfide Bond with Improved Stability *in Vivo*, *Cancer Res. 47*:5924-5931, The American Association for Cancer Research (1987).

Wong, Shan S., "Chemistry of Protein Conjugation and Cross-linking," Pierce Biotechnology, Inc., Product Information Sheet, p. 1, accessed online at http://www.piercenet.com/Products/Browse.cfm?fldID=02051103&Format=Print on Nov. 8, 2004.

Co-pending U.S. Appl. No. 09/529,130, Duggan et al., filed Jun. 22, 2000.

\* cited by examiner

Figure 8

Panel A: eDRG

[Graph: Inhibition of Release (%) vs [WGA-LH$_N$] (microgrammes/ml)]

Panel B: eSC neurons

[Graph: Inhibition of Release (%) vs [WGA-LH$_N$] (microgrammes/ml)]

Figure 9
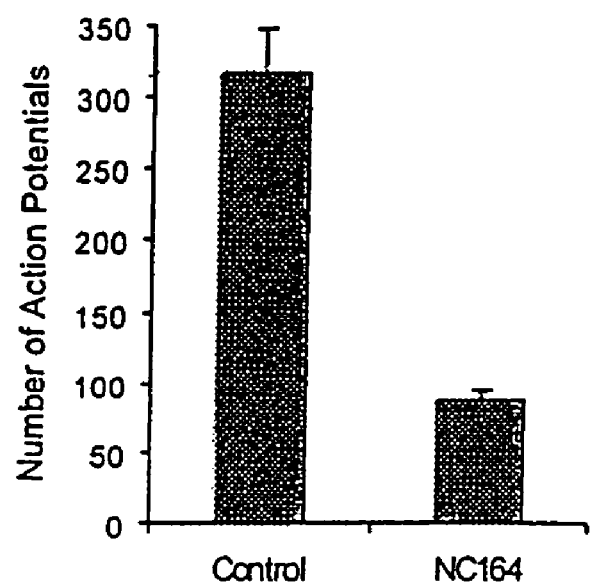
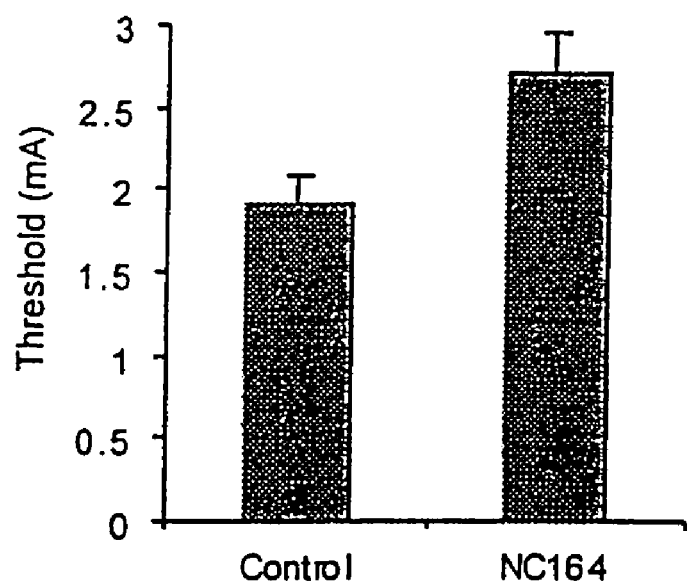

Figure 9
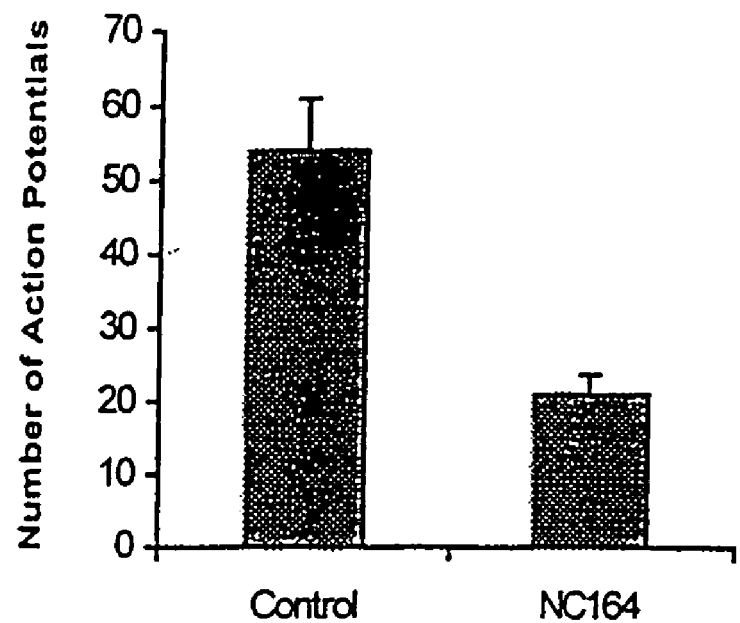
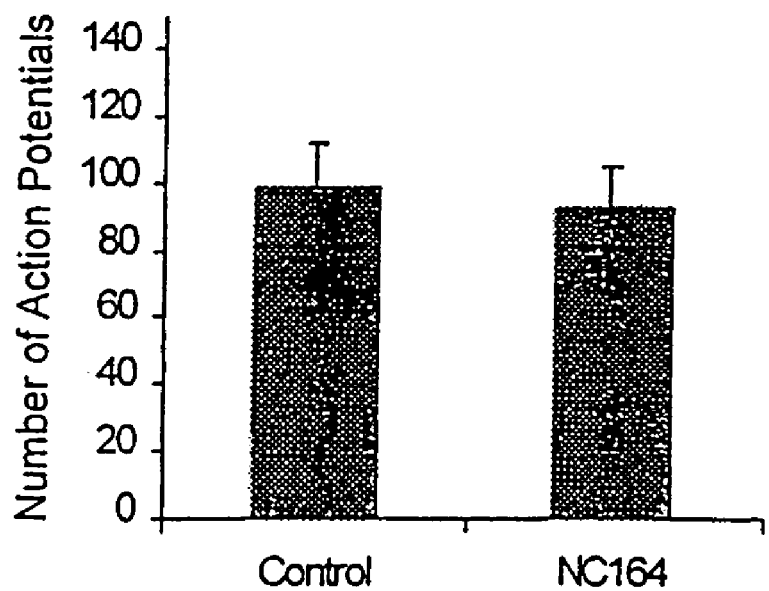

Figure 11. Expression, purification & activation of an LH$_N$/C-ECL fusion protein Lane 1: molecular mass markers
Lane 2: Amylose load
Lane 3: Amylose FT
Lane 4: Amylose FT
Lane 5: Amylose eluent
Lane 6: Amylose eluent
Lane 7: Xa cleavage
Lane 8: Xa cleavage reduced

Figure 12

Figure 12. Expression, purification & activation of an LH$_N$/A-ECL fusion protein Figure 13. Purification and activation of an LH$_N$/B-ECL fusion protein

SEQUENCE LISTING

<160> NUMBER OF SEQ ID NOS: 32

<210> SEQ ID NO 1
<211> LENGTH: 726
<212> TYPE: DNA
<213> ORGANISM: Erythrina cristagalli

<400> SEQUENCE: 1

```
gtggaaacca tatcgtttag cttcagtgag tttgaaccgg gtaacaacga tttgaccttg      60
caaggtgcag ccattattac acaatctggg gttttacaac tcaccaagat taatcaaaat    120
ggcatgccgg cttgggactc aacgggccga actctatata ctaaacctgt gcacatttgg    180
gatatgacca caggcactgt ggccagcttt gaaactagat tctccttttc cattgaacaa    240
ccctatacac gcccactccc cgctgatggt ttagtattct ttatgggacc aacaaagtcc    300
aagccagctc aaggttatgg atacctcgga gtattcaaca actcaaaaca ggataactca    360
taccaaacac ttgctgttga gtttgacact ttcagtaacc catgggaccc tccccaggtt    420
ccacacattg gaatcgatgt caactccatt cgatccatca aaacccaacc ttttcaattg    480
gacaatggcc aagttgccaa tgttgtcata aaatatgatg cttcctccaa aatcttactt    540
gccgtgttgg tttacccttc cagtggagcc atttacacca tcgctgaaat tgtggatgtg    600
aagcaagttc ttcctgagtg ggtcgacgtt ggtctctcgg gtgcaaccgg tgcacagcga    660
gacgccgctg agacacacga cgtttattct tggtcattcc atgcctcgtt gccagaaaca    720
aacgat                                                                726
```

<210> SEQ ID NO 2
<211> LENGTH: 2640
<212> TYPE: DNA
<213> ORGANISM: Artificial sequence
<220> FEATURE:
<223> OTHER INFORMATION: Synthesised DNA sequence of LHn/A with Factor
      Xa activation site

<400> SEQUENCE: 2

```
ggatccatgg agttcgttaa caaacagttc aactataaag acccagttaa cggtgttgac      60
attgcttaca tcaaaatccc gaacgctggc cagatgcagc cggtaaaggc attcaaaatc    120
cacaacaaaa tctgggttat cccggaacgt gataccttta ctaacccgga agaaggtgac    180
ctgaacccgc caccggaagc gaaacaggtg ccggtatctt actatgactc cacctacctg    240
tctaccgata acgaaaagga caactacctg aaaggtgtta ctaaactgtt cgagcgtatt    300
tactccaccg acctgggccg tatgctgctg actagcatcg ttcgcggtat cccgttctgg    360
ggcggttcta ccatcgatac cgaactgaaa gtaatcgaca ctaactgcat caacgttatt    420
cagccggacg gttcctatcg ttccgaagaa ctgaacctgg tgatcatcgg cccgtctgct    480
gatatcatcc agttcgagtg taagagcttt ggtcacgaag ttctgaacct cacccgtaac    540
ggctacggtt ccactcagta catccgtttc tctccggact tcaccttcgg tttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc cacccctgaac    900
```

```
aaagcgaaat ccatcgtggg taccactgct tctctccagt acatgaagaa cgttttaaaa    960 gaaaatacc tgctcagcga agacacctcc ggcaaattct ctgtagacaa gttgaaattc    1020
gataaacttt acaaaatgct gactgaaatt tacaccgaag acaacttcgt taagttcttt    1080
aaagttctga accgcaaaac ctatctgaac ttcgacaagg cagtattcaa aatcaacatc    1140
gtgccgaaag ttaactacac tatctacgat ggtttcaacc tgcgtaacac caacctggct    1200
gctaatttta acggccagaa cacggaaatc aacaacatga acttcacaaa actgaaaaac    1260
ttcactggtc tgttcgagtt ttacaagctg ctgtgcgtcg acggcatcat tacctccaaa    1320
actaaatctc tgatagaagg tagaaacaaa gcgctgaacc tgcagtgtat caaggttaac    1380
aactgggatt tattcttcag cccgagtgaa gacaacttca ccaacgacct gaacaaaggt    1440
gaagaaatca cctcagatac taacatcgaa gcagccgaag aaaacatctc gctgacctg     1500 atccagcagt actacctgac ctttaatttc gacaacgagc cggaaaacat ttctatcgaa    1560
aacctgagct ctgatatcat cggccagctg gaactgatgc cgaacatcga acgtttccca    1620
aacggtaaaa agtacgagct ggacaaatat accatgttcc actacctgcg cgcgcaggaa    1680
tttgaacacg gcaaatcccg tatcgcactg actaactccg ttaacgaagc tctgctcaac    1740
ccgtcccgtg tatacacctt cttctctagc gactacgtga aaaaggtcaa caaagcgact    1800
gaagctgcaa tgttcttggg ttgggttgaa cagcttgttt atgattttac cgacgagacg    1860
tccgaagtat ctactaccga caaaattgcg gatatcacta tcatcatccc gtacatcggt    1920
ccggctctga acattggcaa catgctgtac aaagacgact cgttggcgc actgatcttc     1980 tccggtgcgg tgatcctgct ggagttcatc ccggaaatcg ccatcccggt actgggcacc    2040
tttgctctgg tttcttacat tgcaaacaag gttctgactg tacaaaccat cgacaacgcg    2100
ctgagcaaac gtaacgaaaa atgggatgaa gtttacaaat atatcgtgac caactggctg    2160
gctaaggtta atactcagat cgacctcatc cgcaaaaaaa tgaaagaagc actggaaaac    2220
caggcggaag ctaccaaggc aatcattaac taccagtaca accagtacac cgaggaagaa    2280
aaaaacaaca tcaacttcaa catcgacgat ctgtcctcta aactgaacga atccatcaac    2340
aaagctatga tcaacatcaa caagttcctg aaccagtgct ctgtaagcta tctgatgaac    2400
tccatgatcc cgtacggtgt taaacgtctg gaggacttcg atgcgtctct gaaagacgcc    2460
ctgctgaaat acatttacga caaccgtggc actctgatcg gtcaggttga tcgtctgaag    2520
gacaaagtga acaataccct tatcgaccga tccccttttc agctcagtaa atatgtcgat    2580
aaccaacgcc ttttgtccac tttcaccgaa tacatcaaag gtctagactg atagaagctt    2640
```

<210> SEQ ID NO 3
<211> LENGTH: 775
<212> TYPE: DNA
<213> ORGANISM: Artificial sequence
<220> FEATURE:
<223> OTHER INFORMATION: PCR amplified DNA sequence of GSspacer-ECL

<400> SEQUENCE: 3

```
tctagaaggt ggcggtgggt ccggtggcgg tggctcagtg gaaaccatat cgtttagctt      60
cagtgagttt gaaccgggta caacgatttt gaccttgcaa ggtgcagcca ttattacaca     120 atctgggggtt ttacaactca ccaagattaa tcaaaatggc atgccggctt gggactcaac    180
gggccgaact ctatatacta aacctgtgca catttgggat atgaccacag gcactgtggc    240
cagctttgaa actagattct ccttttccat tgaacaaccc tatacacgcc cactcccgc     300 tgatggttta gtattctta tgggaccaac aaagtccaag ccagctcaag gttatggata     360
```

-continued

| | |
|---|---|
| cctcggagta ttcaacaact caaaacagga taactcatac caaacacttg ctgttgagtt | 420 |
| tgacactttc agtaacccat gggacccctcc ccaggttcca cacattggaa tcgatgtcaa | 480 |
| ctccattcga tccatcaaaa cccaaccttt tcaattggac aatggccaag ttgccaatgt | 540 |
| tgtcataaaa tatgatgctt cctccaaaat cttacttgcc gtgttggttt acccttccag | 600 |
| tggagccatt tacaccatcg ctgaaattgt ggatgtgaag caagttcttc ctgagtgggt | 660 |
| cgacgttggt ctctcggggtg caaccggtgc acagcgagac gccgctgaga cacacgacgt | 720 |
| ttattcttgg tcattccatg cctcgttgcc agaaacaaac gattaatgaa agctt | 775 |

<210> SEQ ID NO 4
<211> LENGTH: 4569
<212> TYPE: DNA
<213> ORGANISM: Artificial sequence
<220> FEATURE:
<223> OTHER INFORMATION: DNA sequence of ORF from pMAL-LHn/A-GSspacer-
ECL

<400> SEQUENCE: 4

| | |
|---|---|
| atgaaaatcg aagaaggtaa actggtaatc tggattaacg cgataaagg ctataacggt | 60 |
| ctcgctgaag tcggtaagaa attcgagaaa gataccggaa ttaaagtcac cgttgagcat | 120 |
| ccggataaac tggaagagaa attcccacag gttgcggcaa ctggcgatgg ccctgacatt | 180 |
| atcttctggg cacacgaccg ctttggtggc tacgctcaat ctggcctgtt ggctgaaatc | 240 |
| accccggaca aagcgttcca ggacaagctg tatccgttta cctgggatgc cgtacgttac | 300 |
| aacggcaagc tgattgctta cccgatcgct gttgaagcgt tatcgctgat ttataacaaa | 360 |
| gatctgctgc cgaacccgcc aaaaacctgg gaagagatcc cggcgctgga taagaactg | 420 |
| aaagcgaaag gtaagagcgc gctgatgttc aacctgcaag aaccgtactt cacctggccg | 480 |
| ctgattgctg ctgacggggg ttatgcgttc aagtatgaaa acggcaagta cgacattaaa | 540 |
| gacgtgggcg tggataacgc tggcgcgaaa gcgggtctga ccttcctggt tgacctgatt | 600 |
| aaaaacaaac acatgaatgc agacaccgat tactccatcg cagaagctgc ctttaataaa | 660 |
| ggcgaaacag cgatgaccat caacggcccg tgggcatggt ccaacatcga caccagcaaa | 720 |
| gtgaattatg gtgtaacggt actgccgacc ttcaagggtc aaccatccaa accgttcgtt | 780 |
| ggcgtgctga gcgcaggtat taacgccgcc agtccgaaca aagagctggc aaaagagttc | 840 |
| ctcgaaaact atctgctgac tgatgaaggt ctggaagcgg ttaataaaga caaaccgctg | 900 |
| ggtgccgtag cgctgaagtc ttacgaggaa gagttggcga agatccacg tattgccgcc | 960 |
| actatggaaa acgccagaa aggtgaaatc atgccgaaca tcccgcagat gtccgctttc | 1020 |
| tggtatgccg tgcgtactgc ggtgatcaac gccgccagcg tcgtcagac tgtcgatgaa | 1080 |
| gccctgaaag acgcgcagac taattcgagc tcgaacaaca caacaataa caataacaac | 1140 |
| aacctcggga tcgagggaag gatttcagaa ttcggatcca tggagttcgt taacaaacag | 1200 |
| ttcaactata agacccagt taacggtgtt gacattgctt acatcaaaat cccgaacgct | 1260 |
| ggccagatgc agccggtaaa ggcattcaaa atccacaaca aatctgggt tatcccggaa | 1320 |
| cgtgatacct ttactaaccc ggaagaaggt gacctgaacc cgccaccgga agcgaaacag | 1380 |
| gtgccggtat cttactatga ctccacctac ctgtctaccg ataacgaaaa ggacaactac | 1440 |
| ctgaaaggtg ttactaaact gttcgagcgt atttactcca ccgacctggg ccgtatgctg | 1500 |
| ctgactagca tcgttcgcgg tatcccgttc tggggcggtt ctaccatcga taccgaactg | 1560 |
| aaagtaatcg acactaactg catcaacgtt attcagccgg acggttccta tcgttccgaa | 1620 |

```
gaactgaacc tggtgatcat cggcccgtct gctgatatca tccagttcga gtgtaagagc   1680
tttggtcacg aagttctgaa cctcacccgt aacggctacg gttccactca gtacatccgt   1740
ttctctccgg acttcacctt cggttttgaa gaatccctgg aagtagacac gaacccactg   1800
ctgggcgctg gtaaattcgc aactgatcct gcggttaccc tggctcacga actgattcat   1860
gcaggccacc gcctgtacgg tatcgccatc aatccgaacc gtgtcttcaa agttaacacc   1920
aacgcgtatt acgagatgtc cggtctggaa gttagcttcg aagaactgcg tactttggc   1980 ggtcacgacg ctaaattcat cgactctctg caagaaaacg agttccgtct gtactactat   2040
aacaagttca agatatcgc atccaccctg aacaaagcga atccatcgt gggtaccact   2100 gcttctctcc agtacatgaa gaacgttttt aagaaaaat acctgctcag cgaagacacc   2160
tccggcaaat tctctgtaga caagttgaaa ttcgataaac tttacaaaat gctgactgaa   2220
atttacaccg aagacaactt cgttaagttc tttaaagttc tgaaccgcaa aacctatctg   2280
aacttcgaca aggcagtatt caaaatcaac atcgtgccga agttaacta cactatctac   2340 gatggtttca acctgcgtaa caccaacctg gctgctaatt ttaacggcca gaacacggaa   2400
atcaacaaca tgaacttcac aaaactgaaa aacttcactg gtctgttcga gttttacaag   2460
ctgctgtgcg tcgacggcat cattacctcc aaaactaaat ctctgataga aggtagaaac   2520
aaagcgctga acctgcagtg tatcaaggtt aacaactggg atttattctt cagcccgagt   2580
gaagacaact tcaccaacga cctgaacaaa ggtgaagaaa tcacctcaga tactaacatc   2640
gaagcagccg aagaaaacat ctcgctggac ctgatccagc agtactacct gacctttaat   2700
ttcgacaacg agccggaaaa catttctatc gaaaacctga gctctgatat catcggccag   2760
ctggaactga tgccgaacat cgaacgtttc ccaaacggta aaaagtacga gctggacaaa   2820
tataccatgt tccactacct gcgcgcgcag gaatttgaac acggcaaatc ccgtatcgca   2880
ctgactaact ccgttaacga agctctgctc aacccgtccc gtgtatacac cttcttctct   2940
agcgactacg tgaaaaaggt caacaaagcg actgaagctg caatgttctt gggttgggtt   3000
gaacagcttg tttatgattt taccgacgag acgtccgaag tatctactac cgacaaaatt   3060
gcggatatca ctatcatcat cccgtacatc ggtccggctc tgaacattgg caacatgctg   3120
tacaaagacg acttcgttgg cgcactgatc ttctccggtg cggtgatcct gctggagttc   3180
atcccggaaa tcgccatccc ggtactgggc acctttgctc tggtttctta cattgcaaac   3240
aaggttctga ctgtacaaac catcgacaac gcgctgagca acgtaacga aaatgggat   3300 gaagtttaca atatatcgt gaccaactgg ctggctaagg ttaatactca gatcgacctc   3360
atccgcaaaa aaatgaaaga agcactgaa accaggcgg aagctaccaa ggcaatcatt   3420
aactaccagt acaaccagta caccgaggaa gaaaaaaaca acatcaactt caacatcgac   3480
gatcgtgcct ctaaactgaa cgaatccatc aacaaagcta tgatcaacat caacaagttc   3540
ctgaaccagt gctctgtaag ctatctgatg aactccatga tcccgtacgg tgttaaacgt   3600
ctggaggact cgatgcgtc tctgaaagac gccctgctga atacatttta cgacaaccgt   3660
ggcactctga tcggtcaggt tgatcgtctg aaggacaaag tgaacaatac cttatcgacc   3720
gacatcccct tcagctcag taaatatgtc gataaccaac gccttttgtc cactttcacc   3780
gaatacatca aggtctagaa ggtggcggt gggtccggtg gcggtggctc agtggaaacc   3840
atatcgttta gcttcagtga gtttgaaccg ggtaacaacg atttgacctt gcaaggtgca   3900
gccattatta cacaatctgg ggttttacaa ctcaccaaga ttaatcaaaa tggcatgccg   3960
```

-continued

```
gcttgggact caacgggccg aactctatat actaaacctg tgcacatttg ggatatgacc    4020
acaggcactg tggccagctt tgaaactaga ttctcctttt ccattgaaca accctataca    4080
cgcccactcc ccgctgatgg tttagtattc tttatgggac aacaaagtc caagccagct    4140 caaggttatg gatacctcgg agtattcaac aactcaaaac aggataactc ataccaaaca    4200
cttgctgttg agtttgacac tttcagtaac ccatgggacc ctccccaggt tccacacatt    4260
ggaatcgatg tcaactccat tcgatccatc aaaacccaac ttttcaatt ggacaatggc    4320 caagttgcca atgttgtcat aaaatatgat gcttcctcca aaatcttact tgccgtgttg    4380
gtttacccct ccagtggagc catttacacc atcgctgaaa ttgtggatgt gaagcaagtt    4440
cttcctgagt gggtcgacgt tggtctctcg ggtgcaaccg gtgcacagcg agacgccgct    4500
gagacacacg acgtttattc ttggtcattc catgcctcgt tgccagaaac aaacgattaa    4560
tgaaagctt                                                           4569
```

<210> SEQ ID NO 5
<211> LENGTH: 1521
<212> TYPE: PRT
<213> ORGANISM: Artificial sequence
<220> FEATURE:
<223> OTHER INFORMATION: Protein sequence of ORF from pMAL-LHn/A-GSspacer-ECL

<400> SEQUENCE: 5

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
```

-continued

```
                245                 250                 255
Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
        290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Leu Gly Ile
        370                 375                 380

Glu Gly Arg Ile Ser Glu Phe Gly Ser Met Glu Phe Val Asn Lys Gln
385                 390                 395                 400

Phe Asn Tyr Lys Asp Pro Val Asn Gly Val Asp Ile Ala Tyr Ile Lys
                405                 410                 415

Ile Pro Asn Ala Gly Gln Met Gln Pro Val Lys Ala Phe Lys Ile His
                420                 425                 430

Asn Lys Ile Trp Val Ile Pro Glu Arg Asp Thr Phe Thr Asn Pro Glu
                435                 440                 445

Glu Gly Asp Leu Asn Pro Pro Pro Glu Ala Lys Gln Val Pro Val Ser
            450                 455                 460

Tyr Tyr Asp Ser Thr Tyr Leu Ser Thr Asp Asn Glu Lys Asp Asn Tyr
465                 470                 475                 480

Leu Lys Gly Val Thr Lys Leu Phe Glu Arg Ile Tyr Ser Thr Asp Leu
                485                 490                 495

Gly Arg Met Leu Leu Thr Ser Ile Val Arg Gly Ile Pro Phe Trp Gly
            500                 505                 510

Gly Ser Thr Ile Asp Thr Glu Leu Lys Val Ile Asp Thr Asn Cys Ile
        515                 520                 525

Asn Val Ile Gln Pro Asp Gly Ser Tyr Arg Ser Glu Glu Leu Asn Leu
            530                 535                 540

Val Ile Ile Gly Pro Ser Ala Asp Ile Ile Gln Phe Glu Cys Lys Ser
545                 550                 555                 560

Phe Gly His Glu Val Leu Asn Leu Thr Arg Asn Gly Tyr Gly Ser Thr
                565                 570                 575

Gln Tyr Ile Arg Phe Ser Pro Asp Phe Thr Phe Gly Phe Glu Glu Ser
            580                 585                 590

Leu Glu Val Asp Thr Asn Pro Leu Leu Gly Ala Gly Lys Phe Ala Thr
        595                 600                 605

Asp Pro Ala Val Thr Leu Ala His Glu Leu Ile His Ala Gly His Arg
    610                 615                 620

Leu Tyr Gly Ile Ala Ile Asn Pro Asn Arg Val Phe Lys Val Asn Thr
625                 630                 635                 640

Asn Ala Tyr Tyr Glu Met Ser Gly Leu Glu Val Ser Phe Glu Glu Leu
                645                 650                 655

Arg Thr Phe Gly Gly His Asp Ala Lys Phe Ile Asp Ser Leu Gln Glu
            660                 665                 670
```

-continued

```
Asn Glu Phe Arg Leu Tyr Tyr Tyr Asn Lys Phe Lys Asp Ile Ala Ser
            675                 680                 685

Thr Leu Asn Lys Ala Lys Ser Ile Val Gly Thr Thr Ala Ser Leu Gln
        690                 695                 700

Tyr Met Lys Asn Val Phe Lys Glu Lys Tyr Leu Leu Ser Glu Asp Thr
705                 710                 715                 720

Ser Gly Lys Phe Ser Val Asp Lys Leu Lys Phe Asp Lys Leu Tyr Lys
                725                 730                 735

Met Leu Thr Glu Ile Tyr Thr Glu Asp Asn Phe Val Lys Phe Phe Lys
            740                 745                 750

Val Leu Asn Arg Lys Thr Tyr Leu Asn Phe Asp Lys Ala Val Phe Lys
        755                 760                 765

Ile Asn Ile Val Pro Lys Val Asn Tyr Thr Ile Tyr Asp Gly Phe Asn
    770                 775                 780

Leu Arg Asn Thr Asn Leu Ala Ala Asn Phe Asn Gly Gln Asn Thr Glu
785                 790                 795                 800

Ile Asn Asn Met Asn Phe Thr Lys Leu Lys Asn Phe Thr Gly Leu Phe
                805                 810                 815

Glu Phe Tyr Lys Leu Leu Cys Val Asp Gly Ile Ile Thr Ser Lys Thr
            820                 825                 830

Lys Ser Leu Ile Glu Gly Arg Asn Lys Ala Leu Asn Leu Gln Cys Ile
        835                 840                 845

Lys Val Asn Asn Trp Asp Leu Phe Phe Ser Pro Ser Glu Asp Asn Phe
    850                 855                 860

Thr Asn Asp Leu Asn Lys Gly Glu Glu Ile Thr Ser Asp Thr Asn Ile
865                 870                 875                 880

Glu Ala Ala Glu Glu Asn Ile Ser Leu Asp Leu Ile Gln Gln Tyr Tyr
                885                 890                 895

Leu Thr Phe Asn Phe Asp Asn Glu Pro Glu Asn Ile Ser Ile Glu Asn
            900                 905                 910

Leu Ser Ser Asp Ile Ile Gly Gln Leu Glu Leu Met Pro Asn Ile Glu
        915                 920                 925

Arg Phe Pro Asn Gly Lys Lys Tyr Glu Leu Asp Lys Tyr Thr Met Phe
    930                 935                 940

His Tyr Leu Arg Ala Gln Glu Phe Glu His Gly Lys Ser Arg Ile Ala
945                 950                 955                 960

Leu Thr Asn Ser Val Asn Glu Ala Leu Leu Asn Pro Ser Arg Val Tyr
                965                 970                 975

Thr Phe Phe Ser Ser Asp Tyr Val Lys Lys Val Asn Lys Ala Thr Glu
            980                 985                 990

Ala Ala Met Phe Leu Gly Trp Val Glu Gln Leu Val Tyr Asp Phe Thr
        995                 1000                1005

Asp Glu Thr Ser Glu Val Ser Thr Thr Asp Lys Ile Ala Asp Ile
    1010                1015                1020

Thr Ile Ile Ile Pro Tyr Ile Gly Pro Ala Leu Asn Ile Gly Asn
    1025                1030                1035

Met Leu Tyr Lys Asp Asp Phe Val Gly Ala Leu Ile Phe Ser Gly
    1040                1045                1050

Ala Val Ile Leu Leu Glu Phe Ile Pro Glu Ile Ala Ile Pro Val
    1055                1060                1065

Leu Gly Thr Phe Ala Leu Val Ser Tyr Ile Ala Asn Lys Val Leu
    1070                1075                1080
```

-continued

```
Thr Val Gln Thr Ile Asp Asn Ala Leu Ser Lys Arg Asn Glu Lys
1085                1090                1095

Trp Asp Glu Val Tyr Lys Tyr Ile Val Thr Asn Trp Leu Ala Lys
1100                1105                1110

Val Asn Thr Gln Ile Asp Leu Ile Arg Lys Lys Met Lys Glu Ala
1115                1120                1125

Leu Glu Asn Gln Ala Glu Ala Thr Lys Ala Ile Ile Asn Tyr Gln
1130                1135                1140

Tyr Asn Gln Tyr Thr Glu Glu Lys Asn Asn Ile Asn Phe Asn
1145                1150                1155

Ile Asp Asp Leu Ser Ser Lys Leu Asn Glu Ser Ile Asn Lys Ala
1160                1165                1170

Met Ile Asn Ile Asn Lys Phe Leu Asn Gln Cys Ser Val Ser Tyr
1175                1180                1185

Leu Met Asn Ser Met Ile Pro Tyr Gly Val Lys Arg Leu Glu Asp
1190                1195                1200

Phe Asp Ala Ser Leu Lys Asp Ala Leu Leu Lys Tyr Ile Tyr Asp
1205                1210                1215

Asn Arg Gly Thr Leu Ile Gly Gln Val Asp Arg Leu Lys Asp Lys
1220                1225                1230

Val Asn Asn Thr Leu Ser Thr Asp Ile Pro Phe Gln Leu Ser Lys
1235                1240                1245

Tyr Val Asp Asn Gln Arg Leu Leu Ser Thr Phe Thr Glu Tyr Ile
1250                1255                1260

Lys Gly Leu Glu Gly Gly Gly Gly Ser Gly Gly Gly Gly Ser Val
1265                1270                1275

Glu Thr Ile Ser Phe Ser Phe Ser Glu Phe Glu Pro Gly Asn Asn
1280                1285                1290

Asp Leu Thr Leu Gln Gly Ala Ala Ile Ile Thr Gln Ser Gly Val
1295                1300                1305

Leu Gln Leu Thr Lys Ile Asn Gln Asn Gly Met Pro Ala Trp Asp
1310                1315                1320

Ser Thr Gly Arg Thr Leu Tyr Thr Lys Pro Val His Ile Trp Asp
1325                1330                1335

Met Thr Thr Gly Thr Val Ala Ser Phe Glu Thr Arg Phe Ser Phe
1340                1345                1350

Ser Ile Glu Gln Pro Tyr Thr Arg Pro Leu Pro Ala Asp Gly Leu
1355                1360                1365

Val Phe Phe Met Gly Pro Thr Lys Ser Lys Pro Ala Gln Gly Tyr
1370                1375                1380

Gly Tyr Leu Gly Val Phe Asn Asn Ser Lys Gln Asp Asn Ser Tyr
1385                1390                1395

Gln Thr Leu Ala Val Glu Phe Asp Thr Phe Ser Asn Pro Trp Asp
1400                1405                1410

Pro Pro Gln Val Pro His Ile Gly Ile Asp Val Asn Ser Ile Arg
1415                1420                1425

Ser Ile Lys Thr Gln Pro Phe Gln Leu Asp Asn Gly Gln Val Ala
1430                1435                1440

Asn Val Val Ile Lys Tyr Asp Ala Ser Ser Lys Ile Leu Leu Ala
1445                1450                1455

Val Leu Val Tyr Pro Ser Ser Gly Ala Ile Tyr Thr Ile Ala Glu
1460                1465                1470

Ile Val Asp Val Lys Gln Val Leu Pro Glu Trp Val Asp Val Gly
```

```
                    1475                1480                1485
            Leu  Ser  Gly  Ala  Thr  Gly  Ala  Gln  Arg  Asp  Ala  Ala  Glu  Thr  His
                    1490                1495                1500

Asp  Val  Tyr  Ser  Trp  Ser  Phe  His  Ala  Ser  Leu  Pro  Glu  Thr  Asn
                    1505                1510                1515

Asp  Lys  Leu
                    1520

<210> SEQ ID NO 6
<211> LENGTH: 2622
<212> TYPE: DNA
<213> ORGANISM: Artificial sequence
<220> FEATURE:
<223> OTHER INFORMATION: Sythesised DNA sequence of LHn/C

<400> SEQUENCE: 6
ggatccatgc cgatcaccat caacaacttc aactacagcg atccggtgga taacaaaaac      60
atcctgtacc tggatacccca tctgaatacc ctggcgaacg aaccggaaaa agcgtttcgt    120
atcaccggca catttgggt tattccggat cgttttagcc gtaacagcaa cccgaatctg     180
aataaaccgc cgcgtgttac cagcccgaaa agcggttatt acgatccgaa ctatctgagc    240
accgatagcg ataaagatac cttcctgaaa gaaatcatca actgttcaa acgcatcaac     300 agccgtgaaa ttggcgaaga actgatctat cgcctgagcc cgatattcc gtttccgggc    360 aacaacaaca ccccgatcaa caccttgat ttcgatgtgg atttcaacag cgttgatgtt   420
aaaacccgcc agggtaacaa ttgggtgaaa accggcagca ttaacccgag cgtgattatt    480
accggtccgc gcgaaaacat tattgatccg gaaccagca cctttaaact gaccaacaac    540 accttgcgg cgcaggaagg ttttggcgcg ctgagcatta ttagcattag cccgcgcttt    600
atgctgacct atagcaacgc gaccaacgat gttggtgaag ccgtttcag caaaagcgaa    660 ttttgcatgg acccgatcct gatcctgatg catgaactga accatgcgat gcataacctg    720
tatggcatcg cgattccgaa cgatcagacc attagcagcg tgaccagcaa catcttttac    780
agccagtaca cgtgaaact ggaatatgcg gaaatctatg cgtttggcgg tccgaccatt    840
gatctgattc cgaaaagcgc gcgcaaatac ttcgaagaaa agcgctgga ttactatcgc    900 agcattgcga acgtctgaa cagcattacc ccgcgaatc cgagcagctt caacaaatat    960
atcggcgaat ataaacagaa actgatccgc aaatatcgct tgtggtgga agcagcggc  1020 gaagttaccg ttaaccgcaa taaattcgtg gaactgtaca cgaactgac ccagatcttc  1080 accgaattta ctatgcgaa atctataac gtgcagaacc gtaaaatcta cctgagcaac  1140
gtgtataccc cggtgaccgc gaatattctg gatgataacg tgtacgatat ccagaacggc  1200
tttaacatcc cgaaaagcaa cctgaacgtt ctgtttatgg ccagaacct gagccgtaat  1260 ccggcgctgc gtaaagtgaa cccggaaaac atgctgtacc tgttcaccaa attttgcgtc  1320
gacgcgattg atggtcgtag cctgtacaac aaaaccctgc agtgtcgtga actgctggtg  1380
aaaaacaccg atctgccgtt tattggcgat atcagcgatg tgaaaaccga tatcttcctg  1440
cgcaaagata tcaacgaaga aaccgaagtg atctactacc cggataacgt gagcgttgat  1500
caggtgatcc tgagcaaaaa caccagcgaa atggtcagc tggatctgct gtatccgagc  1560
attgatagcg aaagcgaaat tctgccgggc gaaaaccagg tgttttacga taaccgtacc  1620
cagaacgtgg attacctgaa cagctattac tacctggaaa gccagaaact gagcgataac  1680
gtggaagatt ttaccttta ccgcagcatt gaagaagcgc tggataacag cgcgaaagtt  1740
```

```
tacacctatt ttccgaccct ggcgaacaaa gttaatgcgg gtgttcaggg cggtctgttt      1800
ctgatgtggg cgaacgatgt ggtggaagat ttcaccacca acatcctgcg taaagatacc      1860
ctggataaaa tcagcgatgt tagcgcgatt attccgtata ttggtccggc gctgaacatt      1920
agcaatagcg tgcgtcgtgg caattttacc gaagcgtttg cggttaccgg tgtgaccatt      1980
ctgctggaag cgtttccgga atttaccatt ccggcgctgg gtgcgtttgt gatctatagc      2040
aaagtgcagg aacgcaacga aatcatcaaa accatcgata actgcctgga acagcgtatt      2100
aaacgctgga agatagcta tgaatggatg atgggcacct ggctgagccg tattatcacc      2160
cagttcaaca acatcagcta ccagatgtac gatagcctga actatcaggc gggtgcgatt      2220
aaagcgaaaa tcgatctgga atacaaaaaa tacagcggca gcgataaaga aaacatcaaa      2280
agccaggttg aaaacctgaa aaacagcctg atgtgaaaa ttagcgaagc gatgaataac      2340
atcaacaaat tcatccgcga atgcagcgtg acctacctgt tcaaaaacat gctgccgaaa      2400
gtgatcgatg aactgaacga atttgatcgc aacaccaaag cgaaactgat caacctgatc      2460
gatagccaca acattattct ggtgggcgaa gtggataaac tgaaagcgaa agttaacaac      2520
agcttccaga acaccatccc gtttaacatc ttcagctata ccaacaacag cctgctgaaa      2580
gatatcatca acgaatactt caatctagac tgatagaagc tt                        2622

<210> SEQ ID NO 7
<211> LENGTH: 781
<212> TYPE: DNA
<213> ORGANISM: Artificial sequence
<220> FEATURE:
<223> OTHER INFORMATION: PCR amplified DNA sequence of HXspacer-ECL

<400> SEQUENCE: 7
tctagaagct gaagctgctg ctaaagaagc tgctgctaaa gctgtggaaa ccatatcgtt       60
tagcttcagt gagtttgaac cgggtaacaa cgatttgacc ttgcaaggtg cagccattat      120
tacacaatct ggggttttac aactcaccaa gattaatcaa aatggcatgc cggcttggga      180
ctcaacgggc cgaactctat atactaaacc tgtgcacatt tgggatatga ccacaggcac      240
tgtggccagc tttgaaacta gattctcctt ttccattgaa caaccctata cacgcccact      300
ccccgctgat ggtttagtat tctttatggg accaacaaag tccaagccag ctcaaggtta      360 tggataccctc ggagtattca caactcaaa acaggataac tcataccaaa cacttgctgt      420
tgagtttgac actttcagta acccatggga ccctccccag gttccacaca ttggaatcga      480
tgtcaactcc attcgatcca tcaaaaccca accttttcaa ttggacaatg ccaagttgc      540 caatgttgtc ataaaatatg atgcttcctc caaaatctta cttgccgtgt tgtttaccc      600 ttccagtgga gccatttaca ccatcgctga aattgtggat gtgaagcaag ttcttcctga      660
gtgggtcgac gttggtctct cgggtgcaac cggtgcacag cgagacgccg ctgagacaca      720
cgacgtttat tcttggtcat tccatgcctc gttgccagaa acaaacgatt aatgaaagct      780
t                                                                     781

<210> SEQ ID NO 8
<211> LENGTH: 4557
<212> TYPE: DNA
<213> ORGANISM: Artificial sequence
<220> FEATURE:
<223> OTHER INFORMATION: DNA sequence of ORF from pMAL-LHn/C-HXspacer-
      ECL

<400> SEQUENCE: 8
```

-continued

| | |
|---|---|
| atgaaaatcg aagaaggtaa actggtaatc tggattaacg gcgataaagg ctataacggt | 60 |
| ctcgctgaag tcggtaagaa attcgagaaa gataccggaa ttaaagtcac cgttgagcat | 120 |
| ccggataaac tggaagagaa attcccacag gttgcggcaa ctggcgatgg ccctgacatt | 180 |
| atcttctggg cacacgaccg ctttggtggc tacgctcaat ctggcctgtt ggctgaaatc | 240 |
| accccggaca aagcgttcca ggacaagctg tatccgttta cctgggatgc cgtacgttac | 300 |
| aacggcaagc tgattgctta cccgatcgct gttgaagcgt tatcgctgat ttataacaaa | 360 |
| gatctgctgc cgaacccgcc aaaaacctgg gaagagatcc cggcgctgga taagaactg | 420 |
| aaagcgaaag gtaagagcgc gctgatgttc aacctgcaag aaccgtactt cacctggccg | 480 |
| ctgattgctg ctgacggggg ttatgcgttc aagtatgaaa acggcaagta cgacattaaa | 540 |
| gacgtgggcg tggataacgc tggcgcgaaa gcgggtctga ccttcctggt tgacctgatt | 600 |
| aaaaacaaac acatgaatgc agacaccgat tactccatcg cagaagctgc ctttaataaa | 660 |
| ggcgaaacag cgatgaccat caacggcccg tgggcatggt ccaacatcga caccagcaaa | 720 |
| gtgaattatg gtgtaacggt actgccgacc ttcaagggtc aaccatccaa accgttcgtt | 780 |
| ggcgtgctga gcgcaggtat taacgccgcc agtccgaaca aagagctggc aaaagagttc | 840 |
| ctcgaaaact atctgctgac tgatgaaggt ctggaagcgg ttaataaaga caaaccgctg | 900 |
| ggtgccgtag cgctgaagtc ttacgaggaa gagttggcga agatccacg tattgccgcc | 960 |
| actatggaaa acgcccagaa aggtgaaatc atgccgaaca tcccgcagat gtccgctttc | 1020 |
| tggtatgccg tgcgtactgc ggtgatcaac gccgccagcg tcgtcagac tgtcgatgaa | 1080 |
| gccctgaaag acgcgcagac taattcgagc tcgaacaaca acaacaataa caataacaac | 1140 |
| aacctcggga tcgagggaag gatttcagaa ttcggatcca tgccgatcac catcaacaac | 1200 |
| ttcaactaca gcgatccggt ggataacaaa aacatcctgt acctggatac ccatctgaat | 1260 |
| accctggcga cgaaccgga aaaagcgttt cgtatcaccg gcaacatttg ggttattccg | 1320 |
| gatcgtttta gccgtaacag caacccgaat ctgaataaac cgccgcgtgt taccagcccg | 1380 |
| aaaagcggtt attacgatcc gaactatctg agcaccgata cgataaaga taccttcctg | 1440 |
| aaagaaatca tcaaactgtt caaacgcatc aacagccgtg aaattggcga gaactgatc | 1500 |
| tatcgcctga gcaccgatat tccgtttccg gcaacaaca acaccccgat caacacccttt | 1560 |
| gatttcgatg tggatttcaa cagcgttgat gttaaaaccc gccagggtaa caattgggtg | 1620 |
| aaaaccggca gcattaaccc gagcgtgatt attaccggtc cgcgcgaaaa cattattgat | 1680 |
| ccggaaacca gcaacctttaa actgaccaac aacacctttg cggcgcagga aggttttggc | 1740 |
| gcgctgagca ttattagcat tagccgcgc tttatgctga cctatagcaa cgcgaccaac | 1800 |
| gatgttggtg aaggccgttt cagcaaaagc gaatttttgca tggacccgat cctgatcctg | 1860 |
| atgcatgaac tgaaccatgc gatgcataac ctgtatggca tcgcgattcc gaacgatcag | 1920 |
| accattagca gcgtgaccag caacatcttt tacagccagt acaacgtgaa actggaatat | 1980 |
| gcggaaatct atgcgtttgg cggtccgacc attgatctga ttccgaaaag cgcgcgcaaa | 2040 |
| tacttcgaag aaaaagcgct ggattactat cgcagcattg cgaacgtct gaacagcatt | 2100 |
| accaccgcga atccgagcag cttcaacaaa tatatcggcg aatataaaca gaaactgatc | 2160 |
| cgcaaatatc gctttgtggt ggaaagcagc ggcgaagtta ccgttaaccg caataaattc | 2220 |
| gtggaactgt acaacgaact gacccagatc ttcaccgaat ttaactatgc gaaaatctat | 2280 |
| aacgtgcaga accgtaaaat ctacctgagc aacgtgtata ccccggtgac cgcgaatatt | 2340 |
| ctggatgata acgtgtacga tatccagaac ggctttaaca tcccgaaaag caacctgaac | 2400 |

-continued

```
gttctgttta tgggccagaa cctgagccgt aatccggcgc tgcgtaaagt gaacccggaa    2460
aacatgctgt acctgttcac caaattttgc gtcgacgcga ttgatggtcg tagcctgtac    2520
aacaaaaccc tgcagtgtcg tgaactgctg gtgaaaaaca ccgatctgcc gtttattggc    2580
gatatcagcg atgtgaaaac cgatatcttc ctgcgcaaag atatcaacga agaaaccgaa    2640
gtgatctact acccggataa cgtgagcgtt gatcaggtga tcctgagcaa aaacaccagc    2700
gaacatggtc agctggatct gctgtatccg agcattgata gcgaaagcga aattctgccg    2760
ggcgaaaacc aggtgttttta cgataaccgt acccagaacg tggattacct gaacagctat    2820
tactacctgg aaagccagaa actgagcgat aacgtggaag attttacctt acccgcagc    2880 attgaagaag cgctggataa cagcgcgaaa gtttacacct atttccgac cctggcgaac    2940 aaagttaatg cgggtgttca gggcggtctg tttctgatgt gggcgaacga tgtggtggaa    3000
gatttcacca ccaacatcct gcgtaaagat accctggata aaatcagcga tgttagcgcg    3060
attattccgt atattggtcc ggcgctgaac attagcaata gcgtgcgtcg tggcaatttt    3120
accgaagcgt ttgcggttac cggtgtgacc attctgctgg aagcgttttcc ggaatttacc    3180 attccggcgc tgggtgcgtt tgtgatctat agcaaagtgc aggaacgcaa cgaaatcatc    3240
aaaaccatcg ataactgcct ggaacagcgt attaaacgct ggaaagatag ctatgaatgg    3300
atgatgggca cctggctgag ccgtattatc acccagttca caacatcag ctaccagatg    3360 tacgatagcc tgaactatca ggcgggtgcg attaaagcga aatcgatct ggaatacaaa    3420 aaatacagcg gcagcgataa agaaaacatc aaaagccagg ttgaaaacct gaaaacagc    3480 ctggatgtga aaattagcga agcgatgaat aacatcaaca aattcatccg gaatgcagc    3540 gtgacctacc tgttcaaaaa catgctgccg aaagtgatcg atgaactgaa cgaatttgat    3600
cgcaacacca aagcgaaact gatcaacctg atcgatagcc acaacattat tctggtgggc    3660
gaagtggata aactgaaagc gaaagttaac aacagcttcc agaacaccat cccgtttaac    3720
atcttcagct ataccaacaa cagcctgctg aaagatatca tcaacgaata cttcaatcta    3780
gaagctgaag ctgctgctaa agaagctgct gctaaagctg tggaaccat atcgtttagc    3840 ttcagtgagt ttgaaccggg taacaacgat ttgaccttgc aaggtgcagc cattattaca    3900
caatctgggg ttttacaact caccaagatt aatcaaaatg gcatgccggc ttgggactca    3960
acgggccgaa ctctatatac taaacctgtg cacatttggg atatgaccac aggcactgtg    4020
gccagctttg aaactagatt ctccttttcc attgaacaac cctatacacg cccactcccc    4080
gctgatggtt tagtattctt tatgggacca acaaagtcca agccagctca aggttatgga    4140
tacctcggag tattcaacaa ctcaaaacag gataactcat accaaacact gctgttgag    4200 tttgacactt tcagtaaccc atgggaccct ccccaggttc cacacattgg aatcgatgtc    4260
aactccattc gatccatcaa aacccaacct tttcaattgg acaatggcca agttgccaat    4320
gttgtcataa aatatgatgc ttcctccaaa atcttacttg ccgtgttggt ttaccctttcc    4380 agtggagcca tttacaccat cgctgaaatt gtggatgtga agcaagttct tcctgagtgg    4440
gtcgacgttg gtctctcggg tgcaaccggt gcacagcgag acgccgctga gacacacgac    4500
gtttattctt ggtcattcca tgcctcgttg ccagaaacaa acgattaatg aaagctt    4557
```

<210> SEQ ID NO 9
<211> LENGTH: 1517
<212> TYPE: PRT
<213> ORGANISM: Artificial sequence
<220> FEATURE:

<223> OTHER INFORMATION: Protein sequence of ORF from pMAL-LHn/C-HXspacer-ECL

<400> SEQUENCE: 9

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Ile Ser Glu Phe Gly Ser Met Pro Ile Thr Ile Asn Asn
385                 390                 395                 400
```

-continued

```
Phe Asn Tyr Ser Asp Pro Val Asp Asn Lys Asn Ile Leu Tyr Leu Asp
            405                 410                 415
Thr His Leu Asn Thr Leu Ala Asn Glu Pro Glu Lys Ala Phe Arg Ile
        420                 425                 430
Thr Gly Asn Ile Trp Val Ile Pro Asp Arg Phe Ser Arg Asn Ser Asn
    435                 440                 445
Pro Asn Leu Asn Lys Pro Pro Arg Val Thr Ser Pro Lys Ser Gly Tyr
450                 455                 460
Tyr Asp Pro Asn Tyr Leu Ser Thr Asp Ser Asp Lys Asp Thr Phe Leu
465                 470                 475                 480
Lys Glu Ile Ile Lys Leu Phe Lys Arg Ile Asn Ser Arg Glu Ile Gly
                485                 490                 495
Glu Glu Leu Ile Tyr Arg Leu Ser Thr Asp Ile Pro Phe Pro Gly Asn
            500                 505                 510
Asn Asn Thr Pro Ile Asn Thr Phe Asp Phe Asp Val Asp Phe Asn Ser
        515                 520                 525
Val Asp Val Lys Thr Arg Gln Gly Asn Asn Trp Val Lys Thr Gly Ser
    530                 535                 540
Ile Asn Pro Ser Val Ile Ile Thr Gly Pro Arg Glu Asn Ile Ile Asp
545                 550                 555                 560
Pro Glu Thr Ser Thr Phe Lys Leu Thr Asn Asn Thr Phe Ala Ala Gln
                565                 570                 575
Glu Gly Phe Gly Ala Leu Ser Ile Ile Ser Ile Ser Pro Arg Phe Met
            580                 585                 590
Leu Thr Tyr Ser Asn Ala Thr Asn Asp Val Gly Glu Gly Arg Phe Ser
        595                 600                 605
Lys Ser Glu Phe Cys Met Asp Pro Ile Leu Ile Leu Met His Glu Leu
    610                 615                 620
Asn His Ala Met His Asn Leu Tyr Gly Ile Ala Ile Pro Asn Asp Gln
625                 630                 635                 640
Thr Ile Ser Ser Val Thr Ser Asn Ile Phe Tyr Ser Gln Tyr Asn Val
                645                 650                 655
Lys Leu Glu Tyr Ala Glu Ile Tyr Ala Phe Gly Gly Pro Thr Ile Asp
            660                 665                 670
Leu Ile Pro Lys Ser Ala Arg Lys Tyr Phe Glu Glu Lys Ala Leu Asp
        675                 680                 685
Tyr Tyr Arg Ser Ile Ala Lys Arg Leu Asn Ser Ile Thr Thr Ala Asn
    690                 695                 700
Pro Ser Ser Phe Asn Lys Tyr Ile Gly Glu Tyr Lys Gln Lys Leu Ile
705                 710                 715                 720
Arg Lys Tyr Arg Phe Val Val Glu Ser Ser Gly Glu Val Thr Val Asn
                725                 730                 735
Arg Asn Lys Phe Val Glu Leu Tyr Asn Glu Leu Thr Gln Ile Phe Thr
            740                 745                 750
Glu Phe Asn Tyr Ala Lys Ile Tyr Asn Val Gln Asn Arg Lys Ile Tyr
        755                 760                 765
Leu Ser Asn Val Tyr Thr Pro Val Thr Ala Asn Ile Leu Asp Asp Asn
    770                 775                 780
Val Tyr Asp Ile Gln Asn Gly Phe Asn Ile Pro Lys Ser Asn Leu Asn
785                 790                 795                 800
Val Leu Phe Met Gly Gln Asn Leu Ser Arg Asn Pro Ala Leu Arg Lys
                805                 810                 815
```

-continued

```
Val Asn Pro Glu Asn Met Leu Tyr Leu Phe Thr Lys Phe Cys Val Asp
            820                 825                 830

Ala Ile Asp Gly Arg Ser Leu Tyr Asn Lys Thr Leu Gln Cys Arg Glu
        835                 840                 845

Leu Leu Val Lys Asn Thr Asp Leu Pro Phe Ile Gly Asp Ile Ser Asp
    850                 855                 860

Val Lys Thr Asp Ile Phe Leu Arg Lys Asp Ile Asn Glu Glu Thr Glu
865                 870                 875                 880

Val Ile Tyr Tyr Pro Asp Asn Val Ser Val Asp Gln Val Ile Leu Ser
                885                 890                 895

Lys Asn Thr Ser Glu His Gly Gln Leu Asp Leu Leu Tyr Pro Ser Ile
            900                 905                 910

Asp Ser Glu Ser Glu Ile Leu Pro Gly Glu Asn Gln Val Phe Tyr Asp
        915                 920                 925

Asn Arg Thr Gln Asn Val Asp Tyr Leu Asn Ser Tyr Tyr Tyr Leu Glu
    930                 935                 940

Ser Gln Lys Leu Ser Asp Asn Val Glu Asp Phe Thr Phe Thr Arg Ser
945                 950                 955                 960

Ile Glu Glu Ala Leu Asp Asn Ser Ala Lys Val Tyr Tyr Phe Pro
                965                 970                 975

Thr Leu Ala Asn Lys Val Asn Ala Gly Val Gln Gly Gly Leu Phe Leu
            980                 985                 990

Met Trp Ala Asn Asp Val Val Glu Asp Phe Thr Thr Asn Ile Leu Arg
        995                 1000                1005

Lys Asp Thr Leu Asp Lys Ile Ser Asp Val Ser Ala Ile Ile Pro
    1010                1015                1020

Tyr Ile Gly Pro Ala Leu Asn Ile Ser Asn Ser Val Arg Arg Gly
    1025                1030                1035

Asn Phe Thr Glu Ala Phe Ala Val Thr Gly Val Thr Ile Leu Leu
    1040                1045                1050

Glu Ala Phe Pro Glu Phe Thr Ile Pro Ala Leu Gly Ala Phe Val
    1055                1060                1065

Ile Tyr Ser Lys Val Gln Glu Arg Asn Glu Ile Ile Lys Thr Ile
    1070                1075                1080

Asp Asn Cys Leu Glu Gln Arg Ile Lys Arg Trp Lys Asp Ser Tyr
    1085                1090                1095

Glu Trp Met Met Gly Thr Trp Leu Ser Arg Ile Ile Thr Gln Phe
    1100                1105                1110

Asn Asn Ile Ser Tyr Gln Met Tyr Asp Ser Leu Asn Tyr Gln Ala
    1115                1120                1125

Gly Ala Ile Lys Ala Lys Ile Asp Leu Glu Tyr Lys Lys Tyr Ser
    1130                1135                1140

Gly Ser Asp Lys Glu Asn Ile Lys Ser Gln Val Glu Asn Leu Lys
    1145                1150                1155

Asn Ser Leu Asp Val Lys Ile Ser Glu Ala Met Asn Asn Ile Asn
    1160                1165                1170

Lys Phe Ile Arg Glu Cys Ser Val Thr Tyr Leu Phe Lys Asn Met
    1175                1180                1185

Leu Pro Lys Val Ile Asp Glu Leu Asn Glu Phe Asp Arg Asn Thr
    1190                1195                1200

Lys Ala Lys Leu Ile Asn Leu Ile Asp Ser His Asn Ile Ile Leu
    1205                1210                1215

Val Gly Glu Val Asp Lys Leu Lys Ala Lys Val Asn Asn Ser Phe
```

|  |  |  |  |  |  |  |  |  |  |
|--|--|--|--|--|--|--|--|--|--|
| Gln | Asn | Thr | Ile | Pro | Phe | Asn | Ile | Phe | Ser | Tyr | Thr | Asn | Asn | Ser |
| 1235 |  |  |  |  | 1240 |  |  |  |  | 1245 |  |  |  |  |

Gln Asn Thr Ile Pro Phe Asn Ile Phe Ser Tyr Thr Asn Asn Ser
    1235                1240                1245

Leu Leu Lys Asp Ile Ile Asn Glu Tyr Phe Asn Leu Glu Ala Glu
    1250                1255                1260

Ala Ala Ala Lys Glu Ala Ala Lys Ala Val Glu Thr Ile Ser
    1265                1270                1275

Phe Ser Phe Ser Glu Phe Glu Pro Gly Asn Asn Asp Leu Thr Leu
    1280                1285                1290

Gln Gly Ala Ala Ile Ile Thr Gln Ser Gly Val Leu Gln Leu Thr
    1295                1300                1305

Lys Ile Asn Gln Asn Gly Met Pro Ala Trp Asp Ser Thr Gly Arg
    1310                1315                1320

Thr Leu Tyr Thr Lys Pro Val His Ile Trp Asp Met Thr Thr Gly
    1325                1330                1335

Thr Val Ala Ser Phe Glu Thr Arg Phe Ser Phe Ser Ile Glu Gln
    1340                1345                1350

Pro Tyr Thr Arg Pro Leu Pro Ala Asp Gly Leu Val Phe Phe Met
    1355                1360                1365

Gly Pro Thr Lys Ser Lys Pro Ala Gln Gly Tyr Gly Tyr Leu Gly
    1370                1375                1380

Val Phe Asn Asn Ser Lys Gln Asp Asn Ser Tyr Gln Thr Leu Ala
    1385                1390                1395

Val Glu Phe Asp Thr Phe Ser Asn Pro Trp Asp Pro Pro Gln Val
    1400                1405                1410

Pro His Ile Gly Ile Asp Val Asn Ser Ile Arg Ser Ile Lys Thr
    1415                1420                1425

Gln Pro Phe Gln Leu Asp Asn Gly Gln Val Ala Asn Val Val Ile
    1430                1435                1440

Lys Tyr Asp Ala Ser Ser Lys Ile Leu Leu Ala Val Leu Val Tyr
    1445                1450                1455

Pro Ser Ser Gly Ala Ile Tyr Thr Ile Ala Glu Ile Val Asp Val
    1460                1465                1470

Lys Gln Val Leu Pro Glu Trp Val Asp Val Gly Leu Ser Gly Ala
    1475                1480                1485

Thr Gly Ala Gln Arg Asp Ala Ala Glu Thr His Asp Val Tyr Ser
    1490                1495                1500

Trp Ser Phe His Ala Ser Leu Pro Glu Thr Asn Asp Lys Leu
    1505                1510                1515

<210> SEQ ID NO 10
<211> LENGTH: 775
<212> TYPE: DNA
<213> ORGANISM: Artificial sequence
<220> FEATURE:
<223> OTHER INFORMATION: Synthesised DNA sequence of GSspacer-ECorL

<400> SEQUENCE: 10
tctagaaggt ggcggtgggt ccggtggcgg tggctcagtg gagacgattt ctttctcatt    60
ctcagaattc gaaccgggta atgataacct gacgctgcaa ggtgccgcgt tgataacaca   120
gtccggtgtc ttacagctca ctaaaatcaa tcagaatggg atgcctgcat gggactcgac   180
cgggcggacc ctgtatgcca aaccagtaca tatctgggac atgaccactg gaaccgttgc   240
cagtttcgag accgtttct cttttagcat agaacagccg tataccgcc cactacctgc   300

-continued

```
tgatggcctg gttttttta tgggcccgac taagtctaaa ccagcgcagg ggtatggcta      360
tcttggcatc tttaataaca gcaaacaaga taacagctac cagacgctgg gcgttgaatt      420 tgatacctttt cgaaccagt gggacccgcc ccaagttccg cacatcggta ttgatgtcaa      480
cagcattcgt agtattaaaa cgcaacccctt tcagctcgat aatggtcagg tggcgaacgt      540
ggtaattaaa tatgacgctt cctctaaaat tttacatgca gttctggtct acccgagctc      600
aggagcgatt tacacgatcg cagaaatcgt tgatgtgaag caggtcctgc cggaatgggt      660
agacgtggga ttgagtggcg ctacaggggc gcaacgcgat gcagccgaaa ctcacgatgt      720
gtactcgtgg tcctttcagg ccagtcttcc tgagacaaat gattaatgaa agctt           775
```

<210> SEQ ID NO 11
<211> LENGTH: 4569
<212> TYPE: DNA
<213> ORGANISM: Artificial sequence
<220> FEATURE:
<223> OTHER INFORMATION: DNA sequence of ORF from pMAL-LHn/A-GSspacer-
      ECorL

<400> SEQUENCE: 11

```
atgaaaatcg aagaaggtaa actggtaatc tggattaacg gcgataaagg ctataacggt       60
ctcgctgaag tcggtaagaa attcgagaaa gataccggaa ttaaagtcac cgttgagcat     120
ccggataaac tggaagagaa attcccacag gttgcgcaa ctggcgatgg ccctgacatt      180
atcttctggg cacacgaccg ctttggtggc tacgctcaat ctggcctgtt ggctgaaatc      240
accccggaca aagcgttcca ggacaagctg tatccgttta cctgggatgc cgtacgttac      300
aacggcaagc tgattgctta cccgatcgct gttgaagcgt tatcgctgat ttataacaaa      360
gatctgctgc cgaacccgcc aaaaacctgg gaagagatcc cggcgctgga taagaaactg      420
aaagcgaaag gtaagagcgc gctgatgttc aacctgcaag aaccgtactt cacctggccg      480
ctgattgctg ctgacggggg ttatgcgttc aagtatgaaa acggcaagta cgacattaaa      540
gacgtgggcg tggataacgc tggcgcgaaa gcgggtctga ccttcctggt tgacctgatt      600
aaaaacaaac acatgaatgc agacaccgat tactccatcg cagaagctgc ctttaataaa      660
ggcgaaacag cgatgaccat caacggcccg tgggcatggt ccaacatcga caccagcaaa      720
gtgaattatg gtgtaacggt actgccgacc ttcaagggtc aaccatccaa accgttcgtt      780
ggcgtgctga gcgcaggtat taacgccgcc agtccgaaca aagagctggc aaaagagttc      840
ctcgaaaact atctgctgac tgatgaaggt ctggaagcgg ttaataaaga caaaccgctg      900
ggtgccgtag cgctgaagtc ttacgaggaa gagttggcga agatccacg tattgccgcc      960 actatggaaa cgcccagaa aggtgaaatc atgccgaaca tcccgcagat gtccgctttc     1020
tggtatgccg tgcgtactgc ggtgatcaac gccgccagcg gtcgtcagac tgtcgatgaa     1080
gccctgaaag acgcgcagac taattcgagc tcgaacaaca caacaataa caataacaac     1140 aacctcggga tcgagggaag gatttcagaa ttcggatcca tggagttcgt taacaaacag     1200
ttcaactata agacccagt taacggtgtt gacattgctt acatcaaaat cccgaacgct     1260
ggccagatgc agccggtaaa ggcattcaaa atccacaaca aatctgggt tatcccggaa     1320 cgtgatacct ttactaaccc ggaagaaggt gacctgaacc cgccaccgga agcgaaacag     1380
gtgccggtat cttactatga ctccacctac ctgtctaccg ataacgaaaa ggacaactac     1440
ctgaaaggtg ttactaaact gttcgagcgt atttactcca ccgacctggg ccgtatgctg     1500
ctgactagca tcgttcgcgg tatcccgttc tggggcggtt ctaccatcga taccgaactg     1560
```

```
aaagtaatcg acactaactg catcaacgtt attcagccgg acggttccta tcgttccgaa    1620
gaactgaacc tggtgatcat cggcccgtct gctgatatca tccagttcga gtgtaagagc    1680
tttggtcacg aagttctgaa cctcacccgt aacggctacg gttccactca gtacatccgt    1740
ttctctccgg acttcacctt cggttttgaa gaatccctgg aagtagacac gaacccactg    1800
ctgggcgctg gtaaattcgc aactgatcct gcggttaccc tggctcacga actgattcat    1860
gcaggccacc gcctgtacgg tatcgccatc aatccgaacc gtgtcttcaa agttaacacc    1920
aacgcgtatt acgagatgtc cggtctggaa gttagcttcg aagaactgcg tacttttggc    1980
ggtcacgacg ctaaattcat cgactctctg caagaaaacg agttccgtct gtactactat    2040
aacaagttca agatatcgc atccaccctg aacaaagcga atccatcgt gggtaccact    2100 gcttctctcc agtacatgaa gaacgttttt aagaaaaat acctgctcag cgaagacacc    2160
tccggcaaat tctctgtaga caagttgaaa ttcgataaac tttacaaaat gctgactgaa    2220
atttacaccg aagacaactt cgttaagttc tttaaagttc tgaaccgcaa aacctatctg    2280
aacttcgaca aggcagtatt caaaatcaac atcgtgccga agttaacta cactatctac    2340 gatggtttca acctgcgtaa caccaacctg gctgctaatt ttaacggcca gaacacggaa    2400
atcaacaaca tgaacttcac aaaactgaaa aacttcactg gtctgttcga gttttacaag    2460
ctgctgtgcg tcgacggcat cattacctcc aaaactaaat ctctgataga aggtagaaac    2520
aaagcgctga acctgcagtg tatcaaggtt aacaactggg atttattctt cagcccgagt    2580
gaagacaact tcaccaacga cctgaacaaa ggtgaagaaa tcacctcaga tactaacatc    2640
gaagcagccg aagaaaacat ctcgctggac ctgatccagc agtactacct gacctttaat    2700
ttcgacaacg agccggaaaa catttctatc gaaaacctga gctctgatat catcggccag    2760
ctggaactga tgccgaacat cgaacgtttc ccaaacggta aaaagtacga gctggacaaa    2820
tataccatgt tccactacct gcgcgcgcag gaatttgaac acggcaaatc ccgtatcgca    2880
ctgactaact ccgttaacga agctctgctc aacccgtccc gtgtatacac cttcttctct    2940
agcgactacg tgaaaaaggt caacaaagcg actgaagctg caatgttctt gggttgggtt    3000
gaacagcttg tttatgattt taccgacgag acgtccgaag tatctactac cgacaaaatt    3060
gcggatatca ctatcatcat cccgtacatc ggtccggctc tgaacattgg caacatgctg    3120
tacaaagacg acttcgttgg cgcactgatc ttctccggtg cggtgatcct gctggagttc    3180
atcccggaaa tcgccatccc ggtactgggc acctttgctc tggtttctta cattgcaaac    3240
aaggttctga ctgtacaaac catcgacaac gcgctgagca acgtaacga aaatgggat    3300 gaagtttaca atatatcgt gaccaactgg ctggctaagg ttaatactca gatcgacctc    3360
atccgcaaaa aaatgaaaga agcactggaa accaggcgg aagctaccaa ggcaatcatt    3420
aactaccagt acaaccagta caccgaggaa gaaaaaaaca acatcaactt caacatcgac    3480
gatctgtcct ctaaactgaa cgaatccatc aacaaagcta tgatcaacat caacaagttc    3540
ctgaaccagt gctctgtaag ctatctgatg aactccatga tcccgtacgg tgttaaacgt    3600
ctggaggact cgatgcgtc tctgaaagac gccctgctga atacattta cgacaaccgt    3660 ggcactctga tcggtcaggt tgatcgtctg aaggacaaag tgaacaatac cttatcgacc    3720 gacatcccctt ttcagctcag taaatatgtc gataaccaac gccttttgtc cactttcacc    3780
gaatacatca aggtctaga aggtggcggt gggtccggtg gcggtggctc agtggagacg    3840
atttctttct cattctcaga attcgaaccg ggtaatgata acctgacgct gcaaggtgcc    3900
gcgttgataa cacagtccgg tgtcttacag ctcactaaaa tcaatcagaa tggtatgcct    3960
```

-continued

```
gcatgggact cgaccgggcg gaccctgtat gccaaaccag tacatatctg ggacatgacc      4020
actggaaccg ttgccagttt cgagacccgt ttctctttta gcatagaaca gccgtatacc      4080
cgcccactac ctgctgatgg cctggttttt tttatgggcc cgactaagtc taaaccagcg      4140
caggggtatg gctatcttgg catctttaat aacagcaaac aagataacag ctaccagacg      4200
ctgggcgttg aatttgatac cttttcgaac cagtgggacc cgccccaagt tccgcacatc      4260
ggtattgatg tcaacagcat tcgtagtatt aaaacgcaac cctttcagct cgataatggt      4320
caggtggcga acgtggtaat taaatatgac gcttcctcta aaattttaca tgcagttctg      4380
gtctacccga gctcaggagc gatttacacg atcgcagaaa tcgttgatgt gaagcaggtc      4440
ctgccggaat gggtagacgt gggattgagt ggcgctacag gggcgcaacg cgatgcagcc      4500
gaaactcacg atgtgtactc gtggtccttt caggccagtc ttcctgagac aaatgattaa      4560
tgaaagctt                                                              4569
```

<210> SEQ ID NO 12
<211> LENGTH: 1521
<212> TYPE: PRT
<213> ORGANISM: Artificial sequence
<220> FEATURE:
<223> OTHER INFORMATION: Protein sequence of ORF from pMAL-LHn/A-
    GSspacer-ECorL

<400> SEQUENCE: 12

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240
```

-continued

```
Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Asn Asn Asn Asn Asn Asn Asn Asn Asn Leu Gly Ile
    370                 375                 380

Glu Gly Arg Ile Ser Glu Phe Gly Ser Met Glu Phe Val Asn Lys Gln
385                 390                 395                 400

Phe Asn Tyr Lys Asp Pro Val Asn Gly Val Asp Ile Ala Tyr Ile Lys
                405                 410                 415

Ile Pro Asn Ala Gly Gln Met Gln Pro Val Lys Ala Phe Lys Ile His
            420                 425                 430

Asn Lys Ile Trp Val Ile Pro Glu Arg Asp Thr Phe Thr Asn Pro Glu
        435                 440                 445

Glu Gly Asp Leu Asn Pro Pro Glu Ala Lys Gln Val Pro Val Ser
    450                 455                 460

Tyr Tyr Asp Ser Thr Tyr Leu Ser Thr Asp Asn Glu Lys Asp Asn Tyr
465                 470                 475                 480

Leu Lys Gly Val Thr Lys Leu Phe Glu Arg Ile Tyr Ser Thr Asp Leu
                485                 490                 495

Gly Arg Met Leu Leu Thr Ser Ile Val Arg Gly Ile Pro Phe Trp Gly
            500                 505                 510

Gly Ser Thr Ile Asp Thr Glu Leu Lys Val Ile Asp Thr Asn Cys Ile
        515                 520                 525

Asn Val Ile Gln Pro Asp Gly Ser Tyr Arg Ser Glu Glu Leu Asn Leu
    530                 535                 540

Val Ile Ile Gly Pro Ser Ala Asp Ile Ile Gln Phe Glu Cys Lys Ser
545                 550                 555                 560

Phe Gly His Glu Val Leu Asn Leu Thr Arg Asn Gly Tyr Gly Ser Thr
                565                 570                 575

Gln Tyr Ile Arg Phe Ser Pro Asp Phe Thr Phe Gly Phe Glu Glu Ser
            580                 585                 590

Leu Glu Val Asp Thr Asn Pro Leu Leu Gly Ala Gly Lys Phe Ala Thr
        595                 600                 605

Asp Pro Ala Val Thr Leu Ala His Glu Leu Ile His Ala Gly His Arg
    610                 615                 620

Leu Tyr Gly Ile Ala Ile Asn Pro Asn Arg Val Phe Lys Val Asn Thr
625                 630                 635                 640

Asn Ala Tyr Tyr Glu Met Ser Gly Leu Glu Val Ser Phe Glu Glu Leu
                645                 650                 655

Arg Thr Phe Gly Gly His Asp Ala Lys Phe Ile Asp Ser Leu Gln Glu
```

```
                    660                 665                 670
Asn Glu Phe Arg Leu Tyr Tyr Asn Lys Phe Lys Asp Ile Ala Ser
            675                 680                 685
Thr Leu Asn Lys Ala Lys Ser Ile Val Gly Thr Thr Ala Ser Leu Gln
        690                 695                 700
Tyr Met Lys Asn Val Phe Lys Glu Lys Tyr Leu Leu Ser Glu Asp Thr
705                 710                 715                 720
Ser Gly Lys Phe Ser Val Asp Lys Leu Lys Phe Asp Lys Leu Tyr Lys
                725                 730                 735
Met Leu Thr Glu Ile Tyr Thr Glu Asp Asn Phe Val Lys Phe Phe Lys
            740                 745                 750
Val Leu Asn Arg Lys Thr Tyr Leu Asn Phe Asp Lys Ala Val Phe Lys
            755                 760                 765
Ile Asn Ile Val Pro Lys Val Asn Tyr Thr Ile Tyr Asp Gly Phe Asn
            770                 775                 780
Leu Arg Asn Thr Asn Leu Ala Ala Asn Phe Asn Gly Gln Asn Thr Glu
785                 790                 795                 800
Ile Asn Asn Met Asn Phe Thr Lys Leu Lys Asn Phe Thr Gly Leu Phe
                805                 810                 815
Glu Phe Tyr Lys Leu Leu Cys Val Asp Gly Ile Ile Thr Ser Lys Thr
            820                 825                 830
Lys Ser Leu Ile Glu Gly Arg Asn Lys Ala Leu Asn Leu Gln Cys Ile
        835                 840                 845
Lys Val Asn Asn Trp Asp Leu Phe Phe Ser Pro Ser Glu Asp Asn Phe
850                 855                 860
Thr Asn Asp Leu Asn Lys Gly Glu Glu Ile Thr Ser Asp Thr Asn Ile
865                 870                 875                 880
Glu Ala Ala Glu Glu Asn Ile Ser Leu Asp Leu Ile Gln Gln Tyr Tyr
                885                 890                 895
Leu Thr Phe Asn Phe Asp Asn Glu Pro Glu Asn Ile Ser Ile Glu Asn
            900                 905                 910
Leu Ser Ser Asp Ile Ile Gly Gln Leu Glu Leu Met Pro Asn Ile Glu
        915                 920                 925
Arg Phe Pro Asn Gly Lys Lys Tyr Glu Leu Asp Lys Tyr Thr Met Phe
        930                 935                 940
His Tyr Leu Arg Ala Gln Glu Phe Glu His Gly Lys Ser Arg Ile Ala
945                 950                 955                 960
Leu Thr Asn Ser Val Asn Glu Ala Leu Leu Asn Pro Ser Arg Val Tyr
                965                 970                 975
Thr Phe Phe Ser Ser Asp Tyr Val Lys Lys Val Asn Lys Ala Thr Glu
            980                 985                 990
Ala Ala Met Phe Leu Gly Trp Val Glu Gln Leu Val Tyr Asp Phe Thr
        995                 1000                1005
Asp Glu Thr Ser Glu Val Ser Thr Thr Asp Lys Ile Ala Asp Ile
    1010                1015                1020
Thr Ile Ile Ile Pro Tyr Ile Gly Pro Ala Leu Asn Ile Gly Asn
    1025                1030                1035
Met Leu Tyr Lys Asp Asp Phe Val Gly Ala Leu Ile Phe Ser Gly
    1040                1045                1050
Ala Val Ile Leu Leu Glu Phe Ile Pro Glu Ile Ala Ile Pro Val
    1055                1060                1065
Leu Gly Thr Phe Ala Leu Val Ser Tyr Ile Ala Asn Lys Val Leu
    1070                1075                1080
```

```
Thr Val Gln Thr Ile Asp Asn Ala Leu Ser Lys Arg Asn Glu Lys
    1085            1090                1095

Trp Asp Glu Val Tyr Lys Tyr Ile Val Thr Asn Trp Leu Ala Lys
    1100            1105                1110

Val Asn Thr Gln Ile Asp Leu Ile Arg Lys Lys Met Lys Glu Ala
    1115            1120                1125

Leu Glu Asn Gln Ala Glu Ala Thr Lys Ala Ile Ile Asn Tyr Gln
    1130            1135                1140

Tyr Asn Gln Tyr Thr Glu Glu Lys Asn Asn Ile Asn Phe Asn
    1145            1150                1155

Ile Asp Asp Leu Ser Ser Lys Leu Asn Glu Ser Ile Asn Lys Ala
    1160            1165                1170

Met Ile Asn Ile Asn Lys Phe Leu Asn Gln Cys Ser Val Ser Tyr
    1175            1180                1185

Leu Met Asn Ser Met Ile Pro Tyr Gly Val Lys Arg Leu Glu Asp
    1190            1195                1200

Phe Asp Ala Ser Leu Lys Asp Ala Leu Leu Lys Tyr Ile Tyr Asp
    1205            1210                1215

Asn Arg Gly Thr Leu Ile Gly Gln Val Asp Arg Leu Lys Asp Lys
    1220            1225                1230

Val Asn Asn Thr Leu Ser Thr Asp Ile Pro Phe Gln Leu Ser Lys
    1235            1240                1245

Tyr Val Asp Asn Gln Arg Leu Leu Ser Thr Phe Thr Glu Tyr Ile
    1250            1255                1260

Lys Gly Leu Glu Gly Gly Gly Gly Ser Gly Gly Gly Gly Ser Val
    1265            1270                1275

Glu Thr Ile Ser Phe Ser Phe Ser Glu Phe Glu Pro Gly Asn Asp
    1280            1285                1290

Asn Leu Thr Leu Gln Gly Ala Ala Leu Ile Thr Gln Ser Gly Val
    1295            1300                1305

Leu Gln Leu Thr Lys Ile Asn Gln Asn Gly Met Pro Ala Trp Asp
    1310            1315                1320

Ser Thr Gly Arg Thr Leu Tyr Ala Lys Pro Val His Ile Trp Asp
    1325            1330                1335

Met Thr Thr Gly Thr Val Ala Ser Phe Glu Thr Arg Phe Ser Phe
    1340            1345                1350

Ser Ile Glu Gln Pro Tyr Thr Arg Pro Leu Pro Ala Asp Gly Leu
    1355            1360                1365

Val Phe Phe Met Gly Pro Thr Lys Ser Lys Pro Ala Gln Gly Tyr
    1370            1375                1380

Gly Tyr Leu Gly Ile Phe Asn Asn Ser Lys Gln Asp Asn Ser Tyr
    1385            1390                1395

Gln Thr Leu Gly Val Glu Phe Asp Thr Phe Ser Asn Gln Trp Asp
    1400            1405                1410

Pro Pro Gln Val Pro His Ile Gly Ile Asp Val Asn Ser Ile Arg
    1415            1420                1425

Ser Ile Lys Thr Gln Pro Phe Gln Leu Asp Asn Gly Gln Val Ala
    1430            1435                1440

Asn Val Val Ile Lys Tyr Asp Ala Ser Ser Lys Ile Leu His Ala
    1445            1450                1455

Val Leu Val Tyr Pro Ser Ser Gly Ala Ile Tyr Thr Ile Ala Glu
    1460            1465                1470
```

-continued

```
Ile Val  Asp Val Lys Gln Val  Leu Pro Glu Trp Val  Asp Val Gly
    1475                 1480                 1485

Leu Ser  Gly Ala Thr Gly Ala  Gln Arg Asp Ala Ala  Glu Thr His
    1490                 1495                 1500

Asp Val  Tyr Ser Trp Ser Phe  Gln Ala Ser Leu Pro  Glu Thr Asn
    1505                 1510                 1515

Asp Lys  Leu
    1520

<210> SEQ ID NO 13
<211> LENGTH: 808
<212> TYPE: DNA
<213> ORGANISM: Artificial sequence
<220> FEATURE:
<223> OTHER INFORMATION: Synthesised DNA sequence of GSspacer-SBA

<400> SEQUENCE: 13
tctagaaggt ggcggtgggt ccggtggcgg tggctcagct gaaacggtct catttagttg     60
gaataagttt gtacctaaac agccgaacat gatcttgcaa ggcgacgcca tcgtgaccag    120
ctcgggcaaa ttacagctca ataaagtgga cgaaaatggc actccaaaac cgagctctct    180
cgggcgcgcc ctttacagta ctccgattca tatatgggat aaagagactg gttcggtggc    240
atccttcgca gcgtctttca attttacctt ttatgcaccg gatacgaaac ggctggccga    300
cggtctggcg tttttcctgg ccccaatcga tactaagcct caaacccatg cgggctatct    360
gggtctgttt aacgaaaacg aaagtgggga tcaggttgta gcggtggagt ttgatacctt    420
ccgtaattca tgggacccgc ccaacccgca tattggcatt aatgtaaact ctatccgctc    480
tattaagacg acctcctggg atttagctaa caataaagtg gccaaagtcc tgatcaccta    540
tgatgcttcc acatcacttc tggtcgcatc gttggtgtac ccgagccagc gtacaagcaa    600
catactgtcg gacgttgtcg atctgaaaac gtctttacca gaatgggtta gaattggatt    660
ttcagcagcg accggtctgg acatccccgg agaaagtcac gatgttctgt cctggagctt    720
cgcgagcaat ctacctcacg ctagcagtaa cattgatccg ttagatctta catcattcgt    780
tttgcatgag gccatttaat gaaagctt                                       808

<210> SEQ ID NO 14
<211> LENGTH: 4584
<212> TYPE: DNA
<213> ORGANISM: Artificial sequence
<220> FEATURE:
<223> OTHER INFORMATION: DNA sequence of ORF from pMAL-LHn/C-GSspacer-
      SBA

<400> SEQUENCE: 14
atgaaaatcg aagaaggtaa actggtaatc tggattaacg gcgataaagg ctataacggt     60
ctcgctgaag tcggtaagaa attcgagaaa gataccggaa ttaaagtcac cgttgagcat    120
ccggataaac tggaagagaa attcccacag gttgcggcaa ctggcgatgg ccctgacatt    180
atcttctggg cacacgaccg ctttggtggc tacgctcaat ctggcctgtt ggctgaaatc    240
accccggaca aagcgttcca ggacaagctg tatccgttta cctgggatgc cgtacgttac    300
aacggcaagc tgattgctta cccgatcgct gttgaagcgt tatcgctgat ttataacaaa    360
gatctgctgc cgaacccgcc aaaaacctgg gaagagatcc cggcgctgga taaagaactg    420
aaagcgaaag gtaagagcgc gctgatgttc aacctgcaag aaccgtactt cacctggccg    480
ctgattgctg ctgacggggg ttatgcgttc aagtatgaaa acggcaagta cgacattaaa    540
```

-continued

```
gacgtgggcg tggataacgc tggcgcgaaa gcgggtctga ccttcctggt tgacctgatt      600
aaaaacaaac acatgaatgc agacaccgat tactccatcg cagaagctgc ctttaataaa      660
ggcgaaacag cgatgaccat caacggcccg tgggcatggt ccaacatcga caccagcaaa      720
gtgaattatg gtgtaacggt actgccgacc ttcaagggtc aaccatccaa accgttcgtt      780
ggcgtgctga cgcagggtat taacgccgcc agtccgaaca aagagctggc aaaagagttc      840
ctcgaaaact atctgctgac tgatgaaggt ctggaagcgg ttaataaaga caaaccgctg      900
ggtgccgtag cgctgaagtc ttacgaggaa gagttggcga agatccacg tattgccgcc       960 actatggaaa acgcccagaa aggtgaaatc atgccgaaca tcccgcagat gtccgctttc     1020
tggtatgccg tgcgtactgc ggtgatcaac gccgccagcg tcgtcagac tgtcgatgaa      1080 gccctgaaag acgcgcagac taattcgagc tcgaacaaca caacaataa caataacaac      1140 aacctcggga tcgagggaag gatttcagaa ttcggatcca tgccgatcac catcaacaac      1200
ttcaactaca gcgatccggt ggataacaaa aacatcctgt acctggatac ccatctgaat      1260
accctggcga acgaaccgga aaaagcgttt cgtatcaccg gcaacatttg ggttattccg      1320
gatcgtttta ccgtaacag caacccgaat ctgaataaac cgccgcgtgt taccagcccg       1380
aaaagcggtt attacgatcc gaactatctg agcaccgata gcgataaaga taccttcctg      1440
aaagaaatca tcaaactgtt caaacgcatc aacagccgtg aaattggcga agaactgatc      1500
tatcgcctga gcaccgatat tccgtttccg ggcaacaaca cacccccgat caacaccttt     1560
gatttcgatg tggatttcaa cagcgttgat gttaaaaccc gccagggtaa caattgggtg      1620
aaaaccggca gcattaaccc gagcgtgatt attaccggtc cgcgcgaaaa cattattgat      1680
ccggaaacca gcacctttaa actgaccaac aacacctttg cggcgcagga aggttttggc      1740
gcgctgagca ttattagcat tagcccgcgc tttatgctga cctatagcaa cgcgaccaac      1800
gatgttggtg aaggccgttt cagcaaaagc gaattttgca tggacccgat cctgatcctg      1860
atgcatgaac tgaaccatgc gatgcataac ctgtatggca tcgcgattcc gaacgatcag      1920
accattagca gcgtgaccag caacatcttt tacagccagt acaacgtgaa actggaatat      1980
gcggaaatct atgcgtttgg cggtccgacc attgatctga ttccgaaaag cgcgcgcaaa      2040
tacttcgaag aaaaagcgct ggattactat cgcagcattg cgaaacgtct gaacagcatt      2100
accaccgcga atccgagcag cttcaacaaa tatatcggcg aatataaaca gaaactgatc      2160
cgcaaatatc gctttgtggt ggaaagcagc ggcgaagtta ccgttaaccg caataaattc      2220
gtggaactgt acaacgaact gacccagatc ttcaccgaat ttaactatgc gaaaatctat      2280
aacgtgcaga accgtaaaat ctacctgagc aacgtgtata ccccggtgac cgcgaatatt      2340
ctggatgata acgtgtacga tatccagaac ggctttaaca tcccgaaaag caacctgaac      2400
gttctgtttt agggccagaa cctgagccgt aatccggcgc tgcgtaaagt gaacccggaa      2460
aacatgctgt acctgttcac caaattttgc gtcgacgcga ttgatggtcg tagcctgtac      2520
aacaaaaccc tgcagtgtcg tgaactgctg gtgaaaaaca ccgatctgcc gtttattggc      2580
gatatcagcg atgtgaaaac cgatatcttc ctgcgcaaag atatcaacga agaaaccgaa      2640
gtgatctact acccggataa cgtgagcgtt gatcaggtga tcctgagcaa aaacaccagc      2700
gaacatggtc agctggatct gctgtatccg agcattgata gcgaaagcga aattctgccg      2760
ggcgaaaacc aggtgtttta cgataaccgt acccagaacg tggattacct gaacagctat      2820
tactacctgg aaagccagaa actgagcgat aacgtggaag attttacctt acccgcagc      2880 attgaagaag cgctggataa cagcgcgaaa gtttacaccct attttccgac cctggcgaac      2940
```

-continued

```
aaagttaatg cgggtgttca gggcggtctg tttctgatgt gggcgaacga tgtggtggaa   3000
gatttcacca ccaacatcct gcgtaaagat accctggata aaatcagcga tgttagcgcg   3060
attattccgt atattggtcc ggcgctgaac attagcaata gcgtgcgtcg tggcaatttt   3120
accgaagcgt ttgcggttac cggtgtgacc attctgctgg aagcgtttcc ggaatttacc   3180
attccggcgc tgggtgcgtt tgtgatctat agcaaagtgc aggaacgcaa cgaaatcatc   3240
aaaaccatcg ataactgcct ggaacagcgt attaaacgct ggaaagatag ctatgaatgg   3300
atgatgggca cctggctgag ccgtattatc acccagttca acaacatcag ctaccagatg   3360
tacgatagcc tgaactatca ggcgggtgcg attaaagcga aaatcgatct ggaatacaaa   3420
aaatacagcg gcagcgataa agaaaacatc aaaagccagg ttgaaaacct gaaaaacagc   3480
ctggatgtga aaattagcga agcgatgaat aacatcaaca aattcatccg cgaatgcagc   3540
gtgacctacc tgttcaaaaa catgctgccg aaagtgatcg atgaactgaa cgaatttgat   3600
cgcaacacca aagcgaaact gatcaacctg atcgatagcc acaacattat tctggtgggc   3660
gaagtggata aactgaaagc gaaagttaac aacagcttcc agaacaccat cccgtttaac   3720
atcttcagct ataccaacaa cagcctgctg aaagatatca tcaacgaata cttcaatcta   3780
gaaggtggcg gtgggtccgg tggcggtggc tcagctgaaa cggtctcatt tagttggaat   3840
aagtttgtac ctaaacagcc gaacatgatc ttgcaaggcg acgccatcgt gaccagctcg   3900
ggcaaattac agctcaataa agtggacgaa aatggcactc caaaaccgag ctctctcggg   3960
cgcgcccttt acagtactcc gattcatata tgggataaag agactggttc ggtggcatcc   4020
ttcgcagcgt ctttcaattt taccttttat gcaccggata cgaaacggct ggccgacggt   4080
ctggcgtttt tcctggcccc aatcgatact aagcctcaaa cccatgcggg ctatctgggt   4140
ctgtttaacg aaaacgaaag tggggatcag gttgtagcgg tggagtttga taccttccgt   4200
aattcatggg acccgcccaa cccgcatatt ggcattaatg taaactctat ccgctctatt   4260
aagacgacct cctgggattt agctaacaat aaagtggcca aagtcctgat cacctatgat   4320
gcttccacat cacttctggt cgcatcgttg gtgtacccga gccagcgtac aagcaacata   4380
ctgtcggacg ttgtcgatct gaaaacgtct ttaccagaat gggttagaat tggattttca   4440
gcagcgaccg gtctggacat ccccggagaa agtcacgatg ttctgtcctg gagcttcgcg   4500
agcaatctac ctcacgctag cagtaacatt gatccgttag atcttacatc attcgttttg   4560
catgaggcca tttaatgaaa gctt                                          4584
```

<210> SEQ ID NO 15
<211> LENGTH: 1526
<212> TYPE: PRT
<213> ORGANISM: Artificial sequence
<220> FEATURE:
<223> OTHER INFORMATION: Protein sequence of ORF from pMAL-LHn/C-GSspacer-SBA

<400> SEQUENCE: 15

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60
```

-continued

```
His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Asn Leu Gly Ile
370                 375                 380

Glu Gly Arg Ile Ser Glu Phe Gly Ser Met Pro Ile Thr Ile Asn Asn
385                 390                 395                 400

Phe Asn Tyr Ser Asp Pro Val Asp Asn Lys Asn Ile Leu Tyr Leu Asp
                405                 410                 415

Thr His Leu Asn Thr Leu Ala Asn Glu Pro Glu Lys Ala Phe Arg Ile
            420                 425                 430

Thr Gly Asn Ile Trp Val Ile Pro Asp Arg Phe Ser Arg Asn Ser Asn
            435                 440                 445

Pro Asn Leu Asn Lys Pro Pro Arg Val Thr Ser Pro Lys Ser Gly Tyr
450                 455                 460

Tyr Asp Pro Asn Tyr Leu Ser Thr Asp Ser Asp Lys Asp Thr Phe Leu
465                 470                 475                 480
```

-continued

Lys Glu Ile Ile Lys Leu Phe Lys Arg Ile Asn Ser Arg Glu Ile Gly
                485                 490                 495

Glu Glu Leu Ile Tyr Arg Leu Ser Thr Asp Ile Pro Phe Pro Gly Asn
            500                 505                 510

Asn Asn Thr Pro Ile Asn Thr Phe Asp Phe Asp Val Asp Phe Asn Ser
        515                 520                 525

Val Asp Val Lys Thr Arg Gln Gly Asn Asn Trp Val Lys Thr Gly Ser
    530                 535                 540

Ile Asn Pro Ser Val Ile Ile Thr Gly Pro Arg Glu Asn Ile Ile Asp
545                 550                 555                 560

Pro Glu Thr Ser Thr Phe Lys Leu Thr Asn Asn Thr Phe Ala Ala Gln
                565                 570                 575

Glu Gly Phe Gly Ala Leu Ser Ile Ile Ser Ile Ser Pro Arg Phe Met
            580                 585                 590

Leu Thr Tyr Ser Asn Ala Thr Asn Asp Val Gly Glu Gly Arg Phe Ser
        595                 600                 605

Lys Ser Glu Phe Cys Met Asp Pro Ile Leu Ile Leu Met His Glu Leu
    610                 615                 620

Asn His Ala Met His Asn Leu Tyr Gly Ile Ala Ile Pro Asn Asp Gln
625                 630                 635                 640

Thr Ile Ser Ser Val Thr Ser Asn Ile Phe Tyr Ser Gln Tyr Asn Val
                645                 650                 655

Lys Leu Glu Tyr Ala Glu Ile Tyr Ala Phe Gly Gly Pro Thr Ile Asp
            660                 665                 670

Leu Ile Pro Lys Ser Ala Arg Lys Tyr Phe Glu Glu Lys Ala Leu Asp
        675                 680                 685

Tyr Tyr Arg Ser Ile Ala Lys Arg Leu Asn Ser Ile Thr Thr Ala Asn
    690                 695                 700

Pro Ser Ser Phe Asn Lys Tyr Ile Gly Glu Tyr Lys Gln Lys Leu Ile
705                 710                 715                 720

Arg Lys Tyr Arg Phe Val Val Glu Ser Ser Gly Glu Val Thr Val Asn
                725                 730                 735

Arg Asn Lys Phe Val Glu Leu Tyr Asn Glu Leu Thr Gln Ile Phe Thr
            740                 745                 750

Glu Phe Asn Tyr Ala Lys Ile Tyr Asn Val Gln Asn Arg Lys Ile Tyr
        755                 760                 765

Leu Ser Asn Val Tyr Thr Pro Val Thr Ala Asn Ile Leu Asp Asp Asn
    770                 775                 780

Val Tyr Asp Ile Gln Asn Gly Phe Asn Ile Pro Lys Ser Asn Leu Asn
785                 790                 795                 800

Val Leu Phe Met Gly Gln Asn Leu Ser Arg Asn Pro Ala Leu Arg Lys
                805                 810                 815

Val Asn Pro Glu Asn Met Leu Tyr Leu Phe Thr Lys Phe Cys Val Asp
            820                 825                 830

Ala Ile Asp Gly Arg Ser Leu Tyr Asn Lys Thr Leu Gln Cys Arg Glu
        835                 840                 845

Leu Leu Val Lys Asn Thr Asp Leu Pro Phe Ile Gly Asp Ile Ser Asp
    850                 855                 860

Val Lys Thr Asp Ile Phe Leu Arg Lys Asp Ile Asn Glu Glu Thr Glu
865                 870                 875                 880

Val Ile Tyr Tyr Pro Asp Asn Val Ser Val Asp Gln Val Ile Leu Ser
                885                 890                 895

Lys Asn Thr Ser Glu His Gly Gln Leu Asp Leu Leu Tyr Pro Ser Ile

-continued

```
                900             905             910
Asp Ser Glu Ser Glu Ile Leu Pro Gly Glu Asn Gln Val Phe Tyr Asp
            915                 920                 925
Asn Arg Thr Gln Asn Val Asp Tyr Leu Asn Ser Tyr Tyr Tyr Leu Glu
        930                 935                 940
Ser Gln Lys Leu Ser Asp Asn Val Glu Asp Phe Thr Phe Thr Arg Ser
945                 950                 955                 960
Ile Glu Glu Ala Leu Asp Asn Ser Ala Lys Val Tyr Thr Tyr Phe Pro
                965                 970                 975
Thr Leu Ala Asn Lys Val Asn Ala Gly Val Gln Gly Gly Leu Phe Leu
            980                 985                 990
Met Trp Ala Asn Asp Val Val Glu Asp Phe Thr Thr Asn Ile Leu Arg
        995                 1000                1005
Lys Asp Thr Leu Asp Lys Ile Ser Asp Val Ser Ala Ile Ile Pro
    1010                1015                1020
Tyr Ile Gly Pro Ala Leu Asn Ile Ser Asn Ser Val Arg Arg Gly
    1025                1030                1035
Asn Phe Thr Glu Ala Phe Ala Val Thr Gly Val Thr Ile Leu Leu
    1040                1045                1050
Glu Ala Phe Pro Glu Phe Thr Ile Pro Ala Leu Gly Ala Phe Val
    1055                1060                1065
Ile Tyr Ser Lys Val Gln Glu Arg Asn Glu Ile Ile Lys Thr Ile
    1070                1075                1080
Asp Asn Cys Leu Glu Gln Arg Ile Lys Arg Trp Lys Asp Ser Tyr
    1085                1090                1095
Glu Trp Met Met Gly Thr Trp Leu Ser Arg Ile Ile Thr Gln Phe
    1100                1105                1110
Asn Asn Ile Ser Tyr Gln Met Tyr Asp Ser Leu Asn Tyr Gln Ala
    1115                1120                1125
Gly Ala Ile Lys Ala Lys Ile Asp Leu Glu Tyr Lys Lys Tyr Ser
    1130                1135                1140
Gly Ser Asp Lys Glu Asn Ile Lys Ser Gln Val Glu Asn Leu Lys
    1145                1150                1155
Asn Ser Leu Asp Val Lys Ile Ser Glu Ala Met Asn Asn Ile Asn
    1160                1165                1170
Lys Phe Ile Arg Glu Cys Ser Val Thr Tyr Leu Phe Lys Asn Met
    1175                1180                1185
Leu Pro Lys Val Ile Asp Glu Leu Asn Glu Phe Asp Arg Asn Thr
    1190                1195                1200
Lys Ala Lys Leu Ile Asn Leu Ile Asp Ser His Asn Ile Ile Leu
    1205                1210                1215
Val Gly Glu Val Asp Lys Leu Lys Ala Lys Val Asn Asn Ser Phe
    1220                1225                1230
Gln Asn Thr Ile Pro Phe Asn Ile Phe Ser Tyr Thr Asn Asn Ser
    1235                1240                1245
Leu Leu Lys Asp Ile Ile Asn Glu Tyr Phe Asn Leu Glu Gly Gly
    1250                1255                1260
Gly Gly Ser Gly Gly Gly Ser Ala Glu Thr Val Ser Phe Ser
    1265                1270                1275
Trp Asn Lys Phe Val Pro Lys Gln Pro Asn Met Ile Leu Gln Gly
    1280                1285                1290
Asp Ala Ile Val Thr Ser Ser Gly Lys Leu Gln Leu Asn Lys Val
    1295                1300                1305
```

| Asp | Glu | Asn | Gly | Thr | Pro | Lys | Pro | Ser | Ser | Leu | Gly | Arg | Ala | Leu |
| | 1310 | | | | 1315 | | | | | 1320 | | | | |

| Tyr | Ser | Thr | Pro | Ile | His | Ile | Trp | Asp | Lys | Glu | Thr | Gly | Ser | Val |
| 1325 | | | | | 1330 | | | | | 1335 | | | | |

| Ala | Ser | Phe | Ala | Ala | Ser | Phe | Asn | Phe | Thr | Phe | Tyr | Ala | Pro | Asp |
| 1340 | | | | | 1345 | | | | | 1350 | | | | |

| Thr | Lys | Arg | Leu | Ala | Asp | Gly | Leu | Ala | Phe | Phe | Leu | Ala | Pro | Ile |
| 1355 | | | | | 1360 | | | | | 1365 | | | | |

| Asp | Thr | Lys | Pro | Gln | Thr | His | Ala | Gly | Tyr | Leu | Gly | Leu | Phe | Asn |
| 1370 | | | | | 1375 | | | | | 1380 | | | | |

| Glu | Asn | Glu | Ser | Gly | Asp | Gln | Val | Val | Ala | Val | Glu | Phe | Asp | Thr |
| 1385 | | | | | 1390 | | | | | 1395 | | | | |

| Phe | Arg | Asn | Ser | Trp | Asp | Pro | Pro | Asn | Pro | His | Ile | Gly | Ile | Asn |
| 1400 | | | | | 1405 | | | | | 1410 | | | | |

| Val | Asn | Ser | Ile | Arg | Ser | Ile | Lys | Thr | Thr | Ser | Trp | Asp | Leu | Ala |
| 1415 | | | | | 1420 | | | | | 1425 | | | | |

| Asn | Asn | Lys | Val | Ala | Lys | Val | Leu | Ile | Thr | Tyr | Asp | Ala | Ser | Thr |
| 1430 | | | | | 1435 | | | | | 1440 | | | | |

| Ser | Leu | Leu | Val | Ala | Ser | Leu | Val | Tyr | Pro | Ser | Gln | Arg | Thr | Ser |
| 1445 | | | | | 1450 | | | | | 1455 | | | | |

| Asn | Ile | Leu | Ser | Asp | Val | Val | Asp | Leu | Lys | Thr | Ser | Leu | Pro | Glu |
| 1460 | | | | | 1465 | | | | | 1470 | | | | |

| Trp | Val | Arg | Ile | Gly | Phe | Ser | Ala | Ala | Thr | Gly | Leu | Asp | Ile | Pro |
| 1475 | | | | | 1480 | | | | | 1485 | | | | |

| Gly | Glu | Ser | His | Asp | Val | Leu | Ser | Trp | Ser | Phe | Ala | Ser | Asn | Leu |
| 1490 | | | | | 1495 | | | | | 1500 | | | | |

| Pro | His | Ala | Ser | Ser | Asn | Ile | Asp | Pro | Leu | Asp | Leu | Thr | Ser | Phe |
| 1505 | | | | | 1510 | | | | | 1515 | | | | |

| Val | Leu | His | Glu | Ala | Ile | Lys | Leu | | | | | | | |
| 1520 | | | | | 1525 | | | | | | | | | |

<210> SEQ ID NO 16
<211> LENGTH: 415
<212> TYPE: DNA
<213> ORGANISM: Artificial sequence
<220> FEATURE:
<223> OTHER INFORMATION: Synthesised DNA sequence of GSspacer-PA-I

<400> SEQUENCE: 16

```
tctagaaggt ggcggtgggt ccggtggcgg tggctcaatg gcctggaaag gtgaggtatt    60
agccaataac gaagcaggcc aagtaacttc gattatctac aacccgggcg atgtcatcac   120
catcgttgct gccggttggg cgagctacgg tcctacgcaa aagtggggac cccagggcga   180
tcgcgaacat ccagaccagg ggttgatctg ccacgatgcg ttctgtggcg cgctggtgat   240
gaaaattggg aattctggca ccattccggt gaataccggc cttttccgtt gggttgctcc   300
gaacaatgtc cagggagcaa ttacgctgat ttataacgac gtgccaggta cctatggtaa   360
taactccggg tcatttagcg ttaatatagg taaagatcag agttaatgaa agctt         415
```

<210> SEQ ID NO 17
<211> LENGTH: 4209
<212> TYPE: DNA
<213> ORGANISM: Artificial sequence
<220> FEATURE:
<223> OTHER INFORMATION: DNA sequence of ORF from pMAL-LHn/A-
      GSspacer-PA-I

<400> SEQUENCE: 17

```
atgaaaatcg aagaaggtaa actggtaatc tggattaacg gcgataaagg ctataacggt      60
ctcgctgaag tcggtaagaa attcgagaaa gataccggaa ttaaagtcac cgttgagcat     120
ccggataaac tggaagagaa attcccacag gttgcggcaa ctggcgatgg ccctgacatt     180
atcttctggg cacacgaccg ctttggtggc tacgctcaat ctggcctgtt ggctgaaatc     240
accccggaca aagcgttcca ggacaagctg tatccgttta cctgggatgc cgtacgttac     300
aacggcaagc tgattgctta cccgatcgct gttgaagcgt tatcgctgat ttataacaaa     360
gatctgctgc cgaacccgcc aaaaacctgg gaagagatcc cggcgctgga taaagaactg     420
aaagcgaaag gtaagagcgc gctgatgttc aacctgcaag aaccgtactt cacctggccg     480
ctgattgctg ctgacggggg ttatgcgttc aagtatgaaa acggcaagta cgacattaaa     540
gacgtgggcg tggataacgc tggcgcgaaa gcgggtctga ccttcctggt tgacctgatt     600
aaaaacaaac acatgaatgc agacaccgat tactccatcg cagaagctgc ctttaataaa     660
ggcgaaacag cgatgaccat caacggcccg tgggcatggt ccaacatcga caccagcaaa     720
gtgaattatg gtgtaacggt actgccgacc ttcaagggtc aaccatccaa accgttcgtt     780
ggcgtgctga gcgcaggtat taacgccgcc agtccgaaca aagagctggc aaaagagttc     840
ctcgaaaact atctgctgac tgatgaaggt ctggaagcgg ttaataaaga caaaccgctg     900
ggtgccgtag cgctgaagtc ttacgaggaa gagttggcga agatccacg tattgccgcc     960
actatggaaa acgcccagaa aggtgaaatc atgccgaaca tcccgcagat gtccgctttc    1020
tggtatgccg tgcgtactgc ggtgatcaac gccgccagcg gtcgtcagac tgtcgatgaa    1080
gccctgaaag acgcgcagac taattcgagc tcgaacaaca caacaataa  caataacaac    1140
aacctcggga tcgagggaag gattttcagaa ttcggatcca tggagttcgt taacaaacag    1200
ttcaactata aagacccagt taacggtgtt gacattgctt acatcaaaat cccgaacgct    1260
ggccagatgc agccggtaaa ggcattcaaa atccacaaca aaatctgggt tatcccggaa    1320
cgtgataccc ttactaaccc ggaagaaggt gacctgaacc cgccaccgga agcgaaacag    1380
gtgccggtat cttactatga ctccacctac ctgtctaccg ataacgaaaa ggacaactac    1440
ctgaaaggtg ttactaaact gttcgagcgt atttactcca ccgacctggg ccgtatgctg    1500
ctgactagca tcgttcgcgg tatcccgttc tggggcggtt ctaccatcga taccgaactg    1560
aaagtaatcg acactaactg catcaacgtt attcagccgg acggttccta tcgttccgaa    1620
gaactgaacc tggtgatcat cggcccgtct gctgatatca tccagttcga gtgtaagagc    1680
tttggtcacg aagttctgaa cctcacccgt aacggctacg gttccactca gtacatccgt    1740
ttctctccgg acttcacctt cggttttgaa gaatccctgg aagtagacac gaacccactg    1800
ctgggcgctg gtaaattcgc aactgatcct gcggttaccc tggctcacga actgattcat    1860
gcaggccacc gcctgtacgg tatcgccatc aatccgaacc gtgtcttcaa agttaacacc    1920
aacgcgtatt acgagatgtc cggtctggaa gttagcttcg aagaactgcg tacttttggc    1980
ggtcacgacg ctaaattcat cgactctctg caagaaaacg agttccgtct gtactactat    2040
aacaagttca aagatatcgc atccacccctg aacaaagcga atccatcgt gggtaccact    2100
gcttctctcc agtacatgaa gaacgttttt aagaaaaat acctgctcag cgaagacacc    2160
tccggcaaat tctctgtaga caagttgaaa ttcgataaac tttacaaaat gctgactgaa    2220
atttacaccg aagacaactt cgttaagttc tttaaagttc tgaaccgcaa aacctatctg    2280
aacttcgaca aggcagtatt caaaatcaac atcgtgccga aagttaacta cactatctac    2340
```

```
gatggtttca acctgcgtaa caccaacctg gctgctaatt ttaacggcca gaacacggaa    2400
atcaacaaca tgaacttcac aaaactgaaa aacttcactg gtctgttcga gttttacaag    2460
ctgctgtgcg tcgacggcat cattacctcc aaaactaaat ctctgataga aggtagaaac    2520
aaagcgctga acctgcagtg tatcaaggtt aacaactggg atttattctt cagcccgagt    2580
gaagacaact tcaccaacga cctgaacaaa ggtgaagaaa tcacctcaga tactaacatc    2640
gaagcagccg aagaaaacat ctcgctggac ctgatccagc agtactacct gacctttaat    2700
ttcgacaacg agccggaaaa catttctatc gaaaacctga gctctgatat catcggccag    2760
ctggaactga tgccgaacat cgaacgtttc ccaaacggta aaagtacga gctggacaaa    2820 tataccatgt ccactacct gcgcgcgcag gaatttgaac acggcaaatc ccgtatcgca    2880
ctgactaact ccgttaacga agctctgctc aacccgtccc gtgtatacac cttcttctct    2940
agcgactacg tgaaaaaggt caacaaagcg actgaagctg caatgttctt gggttgggtt    3000
gaacagcttg tttatgattt taccgacgag acgtccgaag tatctactac cgacaaaatt    3060
gcggatatca ctatcatcat cccgtacatc ggtccggctc tgaacattgg caacatgctg    3120
tacaaagacg acttcgttgg cgcactgatc ttctccggtg cggtgatcct gctggagttc    3180
atcccggaaa tcgccatccc ggtactgggc acctttgctc tggttcctta cattgcaaac    3240
aaggttctga ctgtacaaac catcgacaac gcgctgagca acgtaacga aaaatgggat    3300 gaagtttaca atatatcgt gaccaactgg ctggctaagg ttaatactca gatcgacctc    3360
atccgcaaaa aaatgaaaga agcactggaa accaggcgg aagctaccaa ggcaatcatt    3420
aactaccagt acaaccagta caccgaggaa gaaaaaaaca acatcaactt caacatcgac    3480
gatctgtcct ctaaactgaa cgaatccatc aacaaagcta tgatcaacat caacaagttc    3540
ctgaaccagt gctctgtaag ctatctgatg aactccatga tcccgtacgg tgttaaacgt    3600
ctggaggact cgatgcgtc tctgaaagac gccctgctga atacatttta cgacaaccgt    3660
ggcactctga tcggtcaggt tgatcgtctg aaggacaaag tgaacaatac cttatcgacc    3720 gacatcccctt ttcagctcag taaatatgtc gataaccaac gccttttgtc cactttcacc    3780
gaatacatca aggtctaga aggtggcggt gggtccggtg gcggtggctc aatggcctgg    3840
aaaggtgagg tattagccaa taacgaagca ggccaagtaa cttcgattat ctacaacccg    3900
ggcgatgtca tcaccatcgt tgctgccggt tgggcgagct acggtcctac gcaaaagtgg    3960
ggaccccagg gcgatcgcga acatccgac caggggttga tctgccacga tgcgttctgt    4020
ggcgcgctgg tgatgaaaat tgggaattct ggcaccattc cggtgaatac aggcctttt    4080 cgttgggttg ctccgaacaa tgtccaggga gcaattacgc tgatttataa cgacgtgcca    4140
ggtacctatg gtaataactc cgggtcattt agcgttaata taggtaaaga tcagagttaa    4200
tgaaagctt                                                            4209
```

<210> SEQ ID NO 18
<211> LENGTH: 1401
<212> TYPE: PRT
<213> ORGANISM: Artificial sequence
<220> FEATURE:
<223> OTHER INFORMATION: Protein sequence of ORF from pMAL-LHn/A-
     GSspacer-PA-I

<400> SEQUENCE: 18

Met Lys Ile Glu Glu Gly Lys Leu Val Ile Trp Ile Asn Gly Asp Lys
1               5                   10                  15

-continued

```
Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
370                 375                 380

Glu Gly Arg Ile Ser Glu Phe Gly Ser Met Glu Phe Val Asn Lys Gln
385                 390                 395                 400

Phe Asn Tyr Lys Asp Pro Val Asn Gly Val Asp Ile Ala Tyr Ile Lys
                405                 410                 415

Ile Pro Asn Ala Gly Gln Met Gln Pro Val Lys Ala Phe Lys Ile His
            420                 425                 430

Asn Lys Ile Trp Val Ile Pro Glu Arg Asp Thr Phe Thr Asn Pro Glu
```

-continued

```
              435                 440                 445
Glu Gly Asp Leu Asn Pro Pro Glu Ala Lys Gln Val Pro Val Ser
    450                 455                 460

Tyr Tyr Asp Ser Thr Tyr Leu Ser Thr Asp Asn Glu Lys Asp Asn Tyr
465                 470                 475                 480

Leu Lys Gly Val Thr Lys Leu Phe Glu Arg Ile Tyr Ser Thr Asp Leu
                485                 490                 495

Gly Arg Met Leu Leu Thr Ser Ile Val Arg Gly Ile Pro Phe Trp Gly
                500                 505                 510

Gly Ser Thr Ile Asp Thr Glu Leu Lys Val Ile Asp Thr Asn Cys Ile
            515                 520                 525

Asn Val Ile Gln Pro Asp Gly Ser Tyr Arg Ser Glu Glu Leu Asn Leu
    530                 535                 540

Val Ile Ile Gly Pro Ser Ala Asp Ile Ile Gln Phe Glu Cys Lys Ser
545                 550                 555                 560

Phe Gly His Glu Val Leu Asn Leu Thr Arg Asn Gly Tyr Gly Ser Thr
                565                 570                 575

Gln Tyr Ile Arg Phe Ser Pro Asp Phe Thr Phe Gly Phe Glu Glu Ser
            580                 585                 590

Leu Glu Val Asp Thr Asn Pro Leu Leu Gly Ala Gly Lys Phe Ala Thr
        595                 600                 605

Asp Pro Ala Val Thr Leu Ala His Glu Leu Ile His Ala Gly His Arg
    610                 615                 620

Leu Tyr Gly Ile Ala Ile Asn Pro Asn Arg Val Phe Lys Val Asn Thr
625                 630                 635                 640

Asn Ala Tyr Tyr Glu Met Ser Gly Leu Glu Val Ser Phe Glu Glu Leu
                645                 650                 655

Arg Thr Phe Gly Gly His Asp Ala Lys Phe Ile Asp Ser Leu Gln Glu
            660                 665                 670

Asn Glu Phe Arg Leu Tyr Tyr Asn Lys Phe Lys Asp Ile Ala Ser
        675                 680                 685

Thr Leu Asn Lys Ala Lys Ser Ile Val Gly Thr Thr Ala Ser Leu Gln
    690                 695                 700

Tyr Met Lys Asn Val Phe Lys Glu Lys Tyr Leu Leu Ser Glu Asp Thr
705                 710                 715                 720

Ser Gly Lys Phe Ser Val Asp Lys Leu Lys Phe Asp Lys Leu Tyr Lys
                725                 730                 735

Met Leu Thr Glu Ile Tyr Thr Glu Asp Asn Phe Val Lys Phe Phe Lys
            740                 745                 750

Val Leu Asn Arg Lys Thr Tyr Leu Asn Phe Asp Lys Ala Val Phe Lys
        755                 760                 765

Ile Asn Ile Val Pro Lys Val Asn Tyr Thr Ile Tyr Asp Gly Phe Asn
    770                 775                 780

Leu Arg Asn Thr Asn Leu Ala Ala Asn Phe Asn Gly Gln Asn Thr Glu
785                 790                 795                 800

Ile Asn Asn Met Asn Phe Thr Lys Leu Lys Asn Phe Thr Gly Leu Phe
                805                 810                 815

Glu Phe Tyr Lys Leu Leu Cys Val Asp Gly Ile Ile Thr Ser Lys Thr
            820                 825                 830

Lys Ser Leu Ile Glu Gly Arg Asn Lys Ala Leu Asn Leu Gln Cys Ile
        835                 840                 845

Lys Val Asn Asn Trp Asp Leu Phe Phe Ser Pro Ser Glu Asp Asn Phe
    850                 855                 860
```

-continued

```
Thr Asn Asp Leu Asn Lys Gly Glu Glu Ile Thr Ser Asp Thr Asn Ile
865                 870                 875                 880

Glu Ala Ala Glu Glu Asn Ile Ser Leu Asp Leu Ile Gln Gln Tyr Tyr
                885                 890                 895

Leu Thr Phe Asn Phe Asp Asn Glu Pro Glu Asn Ile Ser Ile Glu Asn
                900                 905                 910

Leu Ser Ser Asp Ile Ile Gly Gln Leu Glu Leu Met Pro Asn Ile Glu
                915                 920                 925

Arg Phe Pro Asn Gly Lys Lys Tyr Glu Leu Asp Lys Tyr Thr Met Phe
            930                 935                 940

His Tyr Leu Arg Ala Gln Glu Phe Glu His Gly Lys Ser Arg Ile Ala
945                 950                 955                 960

Leu Thr Asn Ser Val Asn Glu Ala Leu Leu Asn Pro Ser Arg Val Tyr
                965                 970                 975

Thr Phe Phe Ser Ser Asp Tyr Val Lys Lys Val Asn Lys Ala Thr Glu
                980                 985                 990

Ala Ala Met Phe Leu Gly Trp Val Glu Gln Leu Val Tyr Asp Phe Thr
            995                 1000                1005

Asp Glu Thr Ser Glu Val Ser Thr Thr Asp Lys Ile Ala Asp Ile
    1010                1015                1020

Thr Ile Ile Ile Pro Tyr Ile Gly Pro Ala Leu Asn Ile Gly Asn
    1025                1030                1035

Met Leu Tyr Lys Asp Asp Phe Val Gly Ala Leu Ile Phe Ser Gly
    1040                1045                1050

Ala Val Ile Leu Leu Glu Phe Ile Pro Glu Ile Ala Ile Pro Val
    1055                1060                1065

Leu Gly Thr Phe Ala Leu Val Ser Tyr Ile Ala Asn Lys Val Leu
    1070                1075                1080

Thr Val Gln Thr Ile Asp Asn Ala Leu Ser Lys Arg Asn Glu Lys
    1085                1090                1095

Trp Asp Glu Val Tyr Lys Tyr Ile Val Thr Asn Trp Leu Ala Lys
    1100                1105                1110

Val Asn Thr Gln Ile Asp Leu Ile Arg Lys Lys Met Lys Glu Ala
    1115                1120                1125

Leu Glu Asn Gln Ala Glu Ala Thr Lys Ala Ile Ile Asn Tyr Gln
    1130                1135                1140

Tyr Asn Gln Tyr Thr Glu Glu Lys Asn Asn Ile Asn Phe Asn
    1145                1150                1155

Ile Asp Asp Leu Ser Ser Lys Leu Asn Glu Ser Ile Asn Lys Ala
    1160                1165                1170

Met Ile Asn Ile Asn Lys Phe Leu Asn Gln Cys Ser Val Ser Tyr
    1175                1180                1185

Leu Met Asn Ser Met Ile Pro Tyr Gly Val Lys Arg Leu Glu Asp
    1190                1195                1200

Phe Asp Ala Ser Leu Lys Asp Ala Leu Leu Lys Tyr Ile Tyr Asp
    1205                1210                1215

Asn Arg Gly Thr Leu Ile Gly Gln Val Asp Arg Leu Lys Asp Lys
    1220                1225                1230

Val Asn Asn Thr Leu Ser Thr Asp Ile Pro Phe Gln Leu Ser Lys
    1235                1240                1245

Tyr Val Asp Asn Gln Arg Leu Leu Ser Thr Phe Thr Glu Tyr Ile
    1250                1255                1260
```

-continued

| | | | | | | | | | | |
|---|---|---|---|---|---|---|---|---|---|---|
| Lys | Gly | Leu | Glu | Gly | Gly | Gly | Ser | Gly | Gly | Gly | Ser | Met |
| | 1265 | | | | 1270 | | | | 1275 | | |

Ala Trp Lys Gly Glu Val Leu Ala Asn Asn Glu Ala Gly Gln Val
     1280                1285                1290

Thr Ser Ile Ile Tyr Asn Pro Gly Asp Val Ile Thr Ile Val Ala
     1295                1300                1305

Ala Gly Trp Ala Ser Tyr Gly Pro Thr Gln Lys Trp Gly Pro Gln
     1310                1315                1320

Gly Asp Arg Glu His Pro Asp Gln Gly Leu Ile Cys His Asp Ala
     1325                1330                1335

Phe Cys Gly Ala Leu Val Met Lys Ile Gly Asn Ser Gly Thr Ile
     1340                1345                1350

Pro Val Asn Thr Gly Leu Phe Arg Trp Val Ala Pro Asn Asn Val
     1355                1360                1365

Gln Gly Ala Ile Thr Leu Ile Tyr Asn Asp Val Pro Gly Thr Tyr
     1370                1375                1380

Gly Asn Asn Ser Gly Ser Phe Ser Val Asn Ile Gly Lys Asp Gln
     1385                1390                1395

Ser Lys Leu
     1400

<210> SEQ ID NO 19
<211> LENGTH: 1893
<212> TYPE: DNA
<213> ORGANISM: Artificial sequence
<220> FEATURE:
<223> OTHER INFORMATION: Synthesised DNA sequence of LC/A-DT with a
      Factor Xa activation site

<400> SEQUENCE: 19
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaaccccgc caccggaagc gaaacaggtg ccggtatctt actatgactc cacctacctg     240
tctaccgata cgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg ttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt tccgtctgta ctactataac aagttcaaag atatcgcatc caccctgaac     900
aaagcgaaat ccatcgtggg taccactgct ctctctccagt acatgaagaa cgttttttaaa     960
gaaaaatacc tgctcagcga agacacctcc ggcaaattct ctgtagacaa gttgaaattc     1020
gataaacttt acaaaatgct gactgaaatt tacaccgaag acaacttcgt taagttcttt     1080
aaagttctga accgcaaaac ctatctgaac ttcgacaagg cagtattcaa atcaacatc     1140

```
gtgccgaaag ttaactacac tatctacgat ggtttcaacc tgcgtaacac caacctggct   1200
gctaatttta acggccagaa cacgaaatc aacaacatga acttcacaaa actgaaaaac   1260
ttcactggtc tgttcgagtt ttacaagctg ctgtgcgctg gcaatattga aggccggtct   1320
gtcggtagct cactgtcgtg tatcaatctg gattgggacg taatccgtga taagaccaaa   1380
acaaaaatcg agtctttgaa agaacacggc ccgatcaaaa ataagatgtc tgaatcaccc   1440
aataaaactg tttcggagga aaaagcgaaa cagtatttgg aagagtttca tcaaaccgcg   1500
cttgaacatc cggagctcag tgaactgaaa acagtgacgg gaacgaatcc tgttttgca    1560 ggcgcaaact atgcggcttg ggccgtgaat gttgcccaag taattgatag tgagaccgca   1620
gacaacctgg aaaagacgac cgcagcgtta agcattttac cgggggattgg ttccgtgatg   1680 ggtatagcgg atggagcggt ccaccataac actgaggaaa ttgtcgccca gtcaatcgct   1740
ctgagttccc tgatggttgc acaggctatc ccactagtgg gggaactggt tgacataggt   1800
ttcgccgcct acaacttcgt agaaagcatt attaatcttt ttcaggtggt gcataacagc   1860
tacaaccgcc caggtctaga ctgatagaag ctt                                1893

<210> SEQ ID NO 20
<211> LENGTH: 3822
<212> TYPE: DNA
<213> ORGANISM: Artificial sequence
<220> FEATURE:
<223> OTHER INFORMATION: DNA sequence of ORF from pMAL-LC/A-DT-
      GSspacer-ECL

<400> SEQUENCE: 20
atgaaaatcg aagaaggtaa actggtaatc tggattaacg gcgataaagg ctataacggt     60
ctcgctgaag tcgtaagaa attcgagaaa gatacccgga ttaaagtcac cgttgagcat   120
ccggataaac tggaagagaa attcccacag gttgcggcaa ctggcgatgg ccctgacatt   180
atcttctggg cacacgaccg ctttggtggc tacgctcaat ctggcctgtt ggctgaaatc   240
accccggaca aagcgttcca ggacaagctg tatccgttta cctgggatgc cgtacgttac   300
aacggcaagc tgattgctta cccgatcgct gttgaagcgt tatcgctgat ttataacaaa   360
gatctgctgc cgaacccgcc aaaaacctgg gaagagatcc cggcgctgga taagaactg    420 aaagcgaaag gtaagagcgc gctgatgttc aacctgcaag aaccgtactt cacctggccg   480
ctgattgctg ctgacggggg ttatgcgttc aagtatgaaa acggcaagta cgacattaaa   540
gacgtgggcg tggataacgc tggcgcgaaa gcgggtctga ccttcctggt tgacctgatt   600
aaaaacaaac acatgaatgc agacaccgat tactccatcg cagaagctgc ctttaataaa   660
ggcgaaacag cgatgaccat caacggcccg tgggcatggt caacatcga caccagcaaa   720 gtgaattatg gtgtaacggt actgccgacc ttcaagggtc aaccatccaa accgttcgtt   780
ggcgtgctga cgcagggtat aacgccgcc agtccgaaca aagagctggc aaaagagttc   840
ctcgaaaact atctgctgac tgatgaaggt ctggaagcgg ttaataaaga caaaccgctg   900
ggtgccgtag cgctgaagtc ttacgaggaa gagttggcga agatccacg tattgccgcc   960 actatggaaa acgcccagaa aggtgaaatc atgccgaaca tcccgcagat gtccgctttc  1020
tggtatgccg tgcgtactgc ggtgatcaac gccgccagcg tcgtcagac tgtcgatgaa  1080 gccctgaaag acgcgcagac taattcgagc tcgaacaaca acaacaataa caataacaac  1140
aacctcggga tcgagggaag gatttcagaa ttcggatcca tggagttcgt taacaaacag  1200
ttcaactata agacccagt taacggtgtt gacattgctt acatcaaaat cccgaacgct  1260
```

```
ggccagatgc agccggtaaa ggcattcaaa atccacaaca aaatctgggt tatcccggaa    1320
cgtgatacct ttactaaccc ggaagaaggt gacctgaacc cgccaccgga agcgaaacag    1380
gtgccggtat cttactatga ctccacctac ctgtctaccg ataacgaaaa ggacaactac    1440
ctgaaaggtg ttactaaact gttcgagcgt atttactcca ccgacctggg ccgtatgctg    1500
ctgactagca tcgttcgcgg tatcccgttc tggggcggtt ctaccatcga taccgaactg    1560
aaagtaatcg acactaactg catcaacgtt attcagccgg acggttccta tcgttccgaa    1620
gaactgaacc tggtgatcat cggcccgtct gctgatatca tccagttcga gtgtaagagc    1680
tttggtcacg aagttctgaa cctcacccgt aacggctacg gttccactca gtacatccgt    1740
ttctctccgg acttcacctt cggttttgaa gaatccctgg aagtagacac gaacccactg    1800
ctgggcgctg taaattcgc aactgatcct gcggttaccc tggctcacga actgattcat    1860
gcaggccacc gcctgtacgg tatcgccatc aatccgaacc gtgtcttcaa agttaacacc    1920
aacgcgtatt acgagatgtc cggtctgaa gttagcttcg aagaactgcg tacttttggc    1980
ggtcacgacg ctaaattcat cgactctctg caagaaaacg agttccgtct gtactactat    2040
aacaagttca agatatcgc atccaccctg aacaaagcga atccatcgt gggtaccact    2100 gcttctctcc agtacatgaa gaacgttttt aaagaaaaat acctgctcag cgaagacacc    2160
tccggcaaat ctctgtagaa caagttgaaa ttcgataaac tttacaaaat gctgactgaa    2220
atttacaccg aagacaactt cgttaagttc tttaaagttc tgaaccgcaa aacctatctg    2280
aacttcgaca aggcagtatt caaaatcaac atcgtgccga agttaacta cactatctac    2340 gatggtttca acctgcgtaa caccaacctg gctgctaatt ttaacggcca gaacacggaa    2400
atcaacaaca tgaacttcac aaaactgaaa aacttcactg gtctgttcga gttttacaag    2460
ctgctgtgcg ctggcaatat tgaaggccgg tctgtcggta gctcactgtc gtgtatcaat    2520
ctggattggg acgtaatccg tgataagacc aaaacaaaa tcgagtcttt gaaagaacac    2580
ggcccgatca aaataagat gtctgaatca cccaataaaa ctgtttcgga ggaaaaagcg    2640
aaacagtatt tggaagagtt tcatcaaacc gcgcttgaac atccggagct cagtgaactg    2700
aaaacagtga cgggaacgaa tcctgttttt gcaggcgcaa actatgcggc ttgggccgtg    2760
aatgttgccc aagtaattga tagtgagacc gcagacaacc tggaaaagac gaccgcagcg    2820
ttaagcattt taccggggat tggttccgtg atgggtatag cggatggagc ggtccaccat    2880
aacactgagg aaattgtcgc ccagtcaatc gctctgagtt ccctgatggt tgcacaggct    2940
atcccactag tgggggaact ggttgacata ggtttcgccg cctacaactt cgtagaaagc    3000
attattaatc tttttcaggt ggtgcataac agctacaacc gcccaggtct agaaggtggc    3060
ggtgggtccg gtggcggtgg ctcagtggaa accatatcgt ttagcttcag tgagtttgaa    3120
ccgggtaaca acgatttgac cttgcaaggt gcagccatta ttacacaatc tggggtttta    3180
caactcacca agattaatca aaatggcatg ccggcttggg actcaacggg ccgaactcta    3240
tatactaaac ctgtgcacat ttgggatatg accacaggca ctgtggccag ctttgaaact    3300
agattctcct tttccattga caacccctat acacgcccac tccccgctga tggtttagta    3360
ttctttatgg gaccaacaaa gtccaagcca gctcaaggtt atggatacct cggagtattc    3420
aacaactcaa aacaggataa ctcataccaa acacttgctg ttgagtttga cactttcagt    3480
aacccatggg accctcccca ggttccacac attggaatcg atgtcaactc cattcgatcc    3540
atcaaaaccc aacctttttca attggacaat ggccaagttg ccaatgttgt cataaaatat    3600
gatgcttcct ccaaaatctt acttgccgtg ttggtttacc cttccagtgg agccatttac    3660
```

```
accatcgctg aaattgtgga tgtgaagcaa gttcttcctg agtgggtcga cgttggtctc    3720
tcgggtgcaa ccggtgcaca gcgagacgcc gctgagacac acgacgttta ttcttggtca    3780
ttccatgcct cgttgccaga acaaacgat  taatgaaagc tt                       3822
```

<210> SEQ ID NO 21
<211> LENGTH: 1272
<212> TYPE: PRT
<213> ORGANISM: Artificial sequence
<220> FEATURE:
<223> OTHER INFORMATION: Protein sequence of ORF from pMAL-LC/A-DT-GSspacer-ECL

<400> SEQUENCE: 21

```
Met Lys Ile Glu Glu Gly Lys Leu Val Ile Trp Ile Asn Gly Asp Lys
  1               5                  10                  15

Gly Tyr Asn Gly Leu Ala Glu Val Gly Lys Lys Phe Glu Lys Asp Thr
                 20                  25                  30

Gly Ile Lys Val Thr Val Glu His Pro Asp Lys Leu Glu Glu Lys Phe
             35                  40                  45

Pro Gln Val Ala Ala Thr Gly Asp Gly Pro Asp Ile Ile Phe Trp Ala
         50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
        290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
```

-continued

```
                325                 330                 335
Met Ser Ala Phe Trp Tyr Ala Val Arg Thr Ala Val Ile Asn Ala Ala
                    340                 345                 350

Ser Gly Arg Gln Thr Val Asp Glu Ala Leu Lys Asp Ala Gln Thr Asn
                    355                 360                 365

Ser Ser Ser Asn Asn Asn Asn Asn Asn Asn Asn Asn Leu Gly Ile
                    370                 375                 380

Glu Gly Arg Ile Ser Glu Phe Gly Ser Met Glu Phe Val Asn Lys Gln
385                 390                 395                 400

Phe Asn Tyr Lys Asp Pro Val Asn Gly Val Asp Ile Ala Tyr Ile Lys
                    405                 410                 415

Ile Pro Asn Ala Gly Gln Met Gln Pro Val Lys Ala Phe Lys Ile His
                    420                 425                 430

Asn Lys Ile Trp Val Ile Pro Glu Arg Asp Thr Phe Thr Asn Pro Glu
                    435                 440                 445

Glu Gly Asp Leu Asn Pro Pro Pro Glu Ala Lys Gln Val Pro Val Ser
                    450                 455                 460

Tyr Tyr Asp Ser Thr Tyr Leu Ser Thr Asp Asn Glu Lys Asp Asn Tyr
465                 470                 475                 480

Leu Lys Gly Val Thr Lys Leu Phe Glu Arg Ile Tyr Ser Thr Asp Leu
                    485                 490                 495

Gly Arg Met Leu Leu Thr Ser Ile Val Arg Gly Ile Pro Phe Trp Gly
                    500                 505                 510

Gly Ser Thr Ile Asp Thr Glu Leu Lys Val Ile Asp Thr Asn Cys Ile
                    515                 520                 525

Asn Val Ile Gln Pro Asp Gly Ser Tyr Arg Ser Glu Glu Leu Asn Leu
                    530                 535                 540

Val Ile Ile Gly Pro Ser Ala Asp Ile Ile Gln Phe Glu Cys Lys Ser
545                 550                 555                 560

Phe Gly His Glu Val Leu Asn Leu Thr Arg Asn Gly Tyr Gly Ser Thr
                    565                 570                 575

Gln Tyr Ile Arg Phe Ser Pro Asp Phe Thr Phe Gly Phe Glu Glu Ser
                    580                 585                 590

Leu Glu Val Asp Thr Asn Pro Leu Leu Gly Ala Gly Lys Phe Ala Thr
                    595                 600                 605

Asp Pro Ala Val Thr Leu Ala His Glu Leu Ile His Ala Gly His Arg
                    610                 615                 620

Leu Tyr Gly Ile Ala Ile Asn Pro Asn Arg Val Phe Lys Val Asn Thr
625                 630                 635                 640

Asn Ala Tyr Tyr Glu Met Ser Gly Leu Glu Val Ser Phe Glu Glu Leu
                    645                 650                 655

Arg Thr Phe Gly Gly His Asp Ala Lys Phe Ile Asp Ser Leu Gln Glu
                    660                 665                 670

Asn Glu Phe Arg Leu Tyr Tyr Asn Lys Phe Lys Asp Ile Ala Ser
                    675                 680                 685

Thr Leu Asn Lys Ala Lys Ser Ile Val Gly Thr Thr Ala Ser Leu Gln
                    690                 695                 700

Tyr Met Lys Asn Val Phe Lys Glu Lys Tyr Leu Leu Ser Glu Asp Thr
705                 710                 715                 720

Ser Gly Lys Phe Ser Val Asp Lys Leu Lys Phe Asp Lys Leu Tyr Lys
                    725                 730                 735

Met Leu Thr Glu Ile Tyr Thr Glu Asp Asn Phe Val Lys Phe Phe Lys
                    740                 745                 750
```

-continued

```
Val Leu Asn Arg Lys Thr Tyr Leu Asn Phe Asp Lys Ala Val Phe Lys
            755                 760                 765

Ile Asn Ile Val Pro Lys Val Asn Tyr Thr Ile Tyr Asp Gly Phe Asn
            770                 775                 780

Leu Arg Asn Thr Asn Leu Ala Ala Asn Phe Asn Gly Gln Asn Thr Glu
785                 790                 795                 800

Ile Asn Asn Met Asn Phe Thr Lys Leu Lys Asn Phe Thr Gly Leu Phe
            805                 810                 815

Glu Phe Tyr Lys Leu Leu Cys Ala Gly Asn Ile Glu Gly Arg Ser Val
            820                 825                 830

Gly Ser Ser Leu Ser Cys Ile Asn Leu Asp Trp Asp Val Ile Arg Asp
            835                 840                 845

Lys Thr Lys Thr Lys Ile Glu Ser Leu Lys Glu His Gly Pro Ile Lys
            850                 855                 860

Asn Lys Met Ser Glu Ser Pro Asn Lys Thr Val Ser Glu Glu Lys Ala
865                 870                 875                 880

Lys Gln Tyr Leu Glu Glu Phe His Gln Thr Ala Leu Glu His Pro Glu
            885                 890                 895

Leu Ser Glu Leu Lys Thr Val Thr Gly Thr Asn Pro Val Phe Ala Gly
            900                 905                 910

Ala Asn Tyr Ala Ala Trp Ala Val Asn Val Ala Gln Val Ile Asp Ser
            915                 920                 925

Glu Thr Ala Asp Asn Leu Glu Lys Thr Thr Ala Ala Leu Ser Ile Leu
930                 935                 940

Pro Gly Ile Gly Ser Val Met Gly Ile Ala Asp Gly Ala Val His His
945                 950                 955                 960

Asn Thr Glu Glu Ile Val Ala Gln Ser Ile Ala Leu Ser Ser Leu Met
            965                 970                 975

Val Ala Gln Ala Ile Pro Leu Val Gly Glu Leu Val Asp Ile Gly Phe
            980                 985                 990

Ala Ala Tyr Asn Phe Val Glu Ser Ile Ile Asn Leu Phe Gln Val Val
            995                 1000                1005

His Asn Ser Tyr Asn Arg Pro Gly Leu Glu Gly Gly Gly Gly Ser
            1010                1015                1020

Gly Gly Gly Gly Ser Val Glu Thr Ile Ser Phe Ser Phe Ser Glu
            1025                1030                1035

Phe Glu Pro Gly Asn Asn Asp Leu Thr Leu Gln Gly Ala Ala Ile
            1040                1045                1050

Ile Thr Gln Ser Gly Val Leu Gln Leu Thr Lys Ile Asn Gln Asn
            1055                1060                1065

Gly Met Pro Ala Trp Asp Ser Thr Gly Arg Thr Leu Tyr Thr Lys
            1070                1075                1080

Pro Val His Ile Trp Asp Met Thr Thr Gly Thr Val Ala Ser Phe
            1085                1090                1095

Glu Thr Arg Phe Ser Phe Ser Ile Glu Gln Pro Tyr Thr Arg Pro
            1100                1105                1110

Leu Pro Ala Asp Gly Leu Val Phe Phe Met Gly Pro Thr Lys Ser
            1115                1120                1125

Lys Pro Ala Gln Gly Tyr Gly Tyr Leu Gly Val Phe Asn Asn Ser
            1130                1135                1140

Lys Gln Asp Asn Ser Tyr Gln Thr Leu Ala Val Glu Phe Asp Thr
            1145                1150                1155
```

```
Phe Ser Asn Pro Trp Asp Pro Pro Gln Val Pro His Ile Gly Ile
    1160            1165                1170

Asp Val Asn Ser Ile Arg Ser Ile Lys Thr Gln Pro Phe Gln Leu
    1175            1180                1185

Asp Asn Gly Gln Val Ala Asn Val Val Ile Lys Tyr Asp Ala Ser
    1190            1195                1200

Ser Lys Ile Leu Leu Ala Val Leu Val Tyr Pro Ser Ser Gly Ala
    1205            1210                1215

Ile Tyr Thr Ile Ala Glu Ile Val Asp Val Lys Gln Val Leu Pro
    1220            1225                1230

Glu Trp Val Asp Val Gly Leu Ser Gly Ala Thr Gly Ala Gln Arg
    1235            1240                1245

Asp Ala Ala Glu Thr His Asp Val Tyr Ser Trp Ser Phe His Ala
    1250            1255                1260

Ser Leu Pro Glu Thr Asn Asp Lys Leu
    1265            1270
```

<210> SEQ ID NO 22
<211> LENGTH: 4554
<212> TYPE: DNA
<213> ORGANISM: Artificial sequence
<220> FEATURE:
<223> OTHER INFORMATION: DNA sequence of ORF from pMAL-LC/A-Hn/C-GSspacer-ECL

<400> SEQUENCE: 22

```
atgaaaatcg aagaaggtaa actggtaatc tggattaacg gcgataaagg ctataacggt      60
ctcgctgaag tcggtaagaa attcgagaaa gataccggaa ttaaagtcac cgttgagcat     120
ccggataaac tggaagagaa attcccacag gttgcggcac tggcgatgg ccctgacatt     180 atcttctggg cacacgaccg ctttggtggc tacgctcaat ctggcctgtt ggctgaaatc     240
accccggaca aagcgttcca ggacaagctg tatccgttta cctgggatgc cgtacgttac     300
aacggcaagc tgattgctta cccgatcgct gttgaagcgt atcgctgat ttataacaaa     360 gatctgctgc cgaacccgcc aaaaacctgg aagagatcc cggcgctgga taagaactg     420 aaagcgaaag gtaagagcgc gctgatgttc aacctgcaag aaccgtactt cacctggccg     480
ctgattgctg ctgacggggg ttatgcgttc aagtatgaaa acggcaagta cgacattaaa     540
gacgtgggcg tggataacgc tggcgcgaaa gcgggtctga ccttcctggt tgacctgatt     600
aaaaacaaac acatgaatgc agacaccgat tactccatcg cagaagctgc ctttaataaa     660
ggcgaaacag cgatgaccat caacggcccg tgggcatggt ccaacatcga caccagcaaa     720
gtgaattatg gtgtaacggt actgccgacc ttcaagggtc aaccatccaa accgttcgtt     780
ggcgtgctga gcgcaggtat taacgccgcc agtccgaaca aagagctggc aaaagagttc     840
ctcgaaaact atctgctgac tgatgaaggt ctggaagcgg ttaataaga caaaccgctg     900 ggtgccgtag cgctgaagtc ttacgaggaa gagttggcga agatccacg tattgccgcc     960 actatggaaa acgcccagaa aggtgaaatc atgccgaaca tcccgcagat gtccgctttc    1020
tggtatgccg tgcgtactgc ggtgatcaac gccgccagcg gtcgtcagac tgtcgatgaa    1080
gccctgaaag acgcgcagac taattcgagc tcaacaaca caacaataa caataacaac    1140 aacctcggga tcgagggaag gatttcagaa ttcggatcca tggagttcgt taacaaacag    1200
ttcaactata agacccagt taacggtgtt gacattgctt acatcaaaat cccgaacgct    1260
ggccagatgc agccggtaaa ggcattcaaa atccacaaca aatctgggt tatcccggaa    1320
```

```
cgtgatacct ttactaaccc ggaagaaggt gacctgaacc cgccaccgga agcgaaacag    1380
gtgccggtat cttactatga ctccacctac ctgtctaccg ataacgaaaa ggacaactac    1440
ctgaaaggtg ttactaaact gttcgagcgt atttactcca ccgacctggg ccgtatgctg    1500
ctgactagca tcgttcgcgg tatcccgttc tggggcggtt ctaccatcga taccgaactg    1560
aaagtaatcg acactaactg catcaacgtt attcagccgg acggttccta tcgttccgaa    1620
gaactgaacc tggtgatcat cggcccgtct gctgatatca tccagttcga gtgtaagagc    1680
tttggtcacg aagttctgaa cctcacccgt aacggctacg gttccactca gtacatccgt    1740
ttctctccgg acttcacctt cggttttgaa gaatccctgg aagtagacac gaacccactg    1800
ctgggcgctg gtaaattcgc aactgatcct gcggttaccc tggctcacga actgattcat    1860
gcaggccacc gcctgtacgg tatcgccatc aatccgaacc gtgtcttcaa agttaacacc    1920
aacgcgtatt acgagatgtc cggtctggaa gttagcttcg aagaactgcg tacttttggc    1980
ggtcacgacg ctaaattcat cgactctctg caagaaaacg agttccgtct gtactactat    2040
aacaagttca agatatcgc atccaccctg aacaaagcga atccatcgt gggtaccact    2100 gcttctctcc agtacatgaa gaacgttttt aagaaaaat acctgctcag cgaagacacc    2160
tccggcaaat tctctgtaga caagttgaaa ttcgataaac tttacaaaat gctgactgaa    2220
atttacaccg aagacaactt cgttaagttc tttaaagttc tgaaccgcaa aacctatctg    2280
aacttcgaca aggcagtatt caaaatcaac atcgtgccga agttaacta cactatctac    2340 gatggtttca acctgcgtaa caccaacctg gctgctaatt ttaacggcca gaacacggaa    2400
atcaacaaca tgaacttcac aaaactgaaa aacttcactg gtctgttcga gttttacaag    2460
ctgctgtgcg tcgacggcat cattacctcc aaaactaaat ctctgataga aggtagaaac    2520
aaagcgctga acctgcagtg tcgtgaactg ctggtgaaaa acaccgatct gccgtttatt    2580
ggcgatatca gcgatgtgaa aaccgatatc ttcctgcgca aagatatcaa cgaagaaacc    2640
gaagtgatct actacccgga taacgtgagc gttgatcagg tgatcctgag caaaaacacc    2700
agcgaacatg gtcagctgga tctgctgtat ccgagcattg atagcgaaag cgaaattctg    2760
ccgggcgaaa accaggtgtt ttacgataac cgtacccaga acgtggatta cctgaacagc    2820
tattactacc tggaaagcca gaaactgagc gataacgtgg aagattttac ctttacccgc    2880
agcattgaag aagcgctgga taacagcgcg aaagtttaca cctatttttcc gaccctggcg    2940 aacaaagtta atgcgggtgt tcagggcggt ctgtttctga tgtgggcgaa cgatgtggtg    3000
gaagatttca ccaccaacat cctgcgtaaa gatacccctgg ataaaatcag cgatgttagc    3060
gcgattattc cgtatattgg tccggcgctg aacattagca atagcgtgcg tcgtggcaat    3120
tttaccgaag cgtttgcggt taccggtgtg accattctgc tggaagcgtt tccggaattt    3180
accattccgg cgctgggtgc gtttgtgatc tatagcaaag tgcaggaacg caacgaaatc    3240
atcaaaacca tcgataactg cctggaacag cgtattaaac gctggaaaga tagctatgaa    3300
tggatgatgg gcacctggct gagccgtatt atcacccagt tcaacaacat cagctaccag    3360
atgtacgata gcctgaacta tcaggcgggt gcgattaaag cgaaaatcga tctggaatac    3420
aaaaaataca gcggcagcga taaagaaaac atcaaaagcc aggttgaaaa cctgaaaaac    3480
agcctggatg tgaaaattag cgaagcgatg aataacatca caaattcat ccgcgaatgc    3540 agcgtgacct acctgttcaa aaacatgctg ccgaaagtga tcgatgaact gaacgaattt    3600
gatcgcaaca ccaaagcgaa actgatcaac ctgatcgata gccacaacat tattctggtg    3660
ggcgaagtgg ataaaactgaa agcgaaagtt aacaacagct tccagaacac catcccgttt    3720
```

-continued

```
aacatcttca gctataccaa caacagcctg ctgaaagata tcatcaacga atacttcaat    3780
ctagaaggtg gcggtgggtc cggtggcggt ggctcagtgg aaaccatatc gtttagcttc    3840
agtgagtttg aaccgggtaa caacgatttg accttgcaag gtgcagccat tattacacaa    3900
tctgggtttt tacaactcac caagattaat caaaatggca tgccggcttg ggactcaacg    3960
ggccgaactc tatatactaa acctgtgcac atttgggata tgaccacagg cactgtggcc    4020
agctttgaaa ctagattctc cttttccatt gaacaaccct atacacgccc actccccgct    4080
gatggtttag tattctttat gggaccaaca aagtccaagc cagctcaagg ttatggatac    4140
ctcggagtat tcaacaactc aaaacaggat aactcatacc aaacacttgc tgttgagttt    4200
gacactttca gtaacccatg ggaccctccc caggttccac acattggaat cgatgtcaac    4260
tccattcgat ccatcaaaac ccaaccttt caattggaca atggccaagt tgccaatgtt    4320
gtcataaaat atgatgcttc ctccaaaatc ttacttgccg tgttggttta cccttccagt    4380
ggagccattt acaccatcgc tgaaattgtg gatgtgaagc aagttcttcc tgagtgggtc    4440
gacgttggtc tctcgggtgc aaccggtgca cagcgagacg ccgctgagac acacgacgtt    4500
tattcttggt cattccatgc ctcgttgcca gaaacaaacg attaatgaaa gctt          4554
```

<210> SEQ ID NO 23
<211> LENGTH: 1516
<212> TYPE: PRT
<213> ORGANISM: Artificial sequence
<220> FEATURE:
<223> OTHER INFORMATION: Protein sequence of ORF from pMAL-LC/A-Hn/C-GSspacer-ECL

<400> SEQUENCE: 23

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205
```

-continued

```
Thr Asp Tyr Ser Ile Ala Glu Ala Ala Phe Asn Lys Gly Glu Thr Ala
    210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
            260                 265                 270
Asn Lys Glu Leu Ala Lys Glu Phe Leu Glu Asn Tyr Leu Leu Thr Asp
        275                 280                 285
Glu Gly Leu Glu Ala Val Asn Lys Asp Lys Pro Leu Gly Ala Val Ala
290                 295                 300
Leu Lys Ser Tyr Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
            340                 345                 350
Ser Gly Arg Gln Thr Val Asp Glu Ala Leu Lys Asp Ala Gln Thr Asn
        355                 360                 365
Ser Ser Ser Asn Asn Asn Asn Asn Asn Asn Asn Leu Gly Ile
370                 375                 380
Glu Gly Arg Ile Ser Glu Phe Gly Ser Met Glu Phe Val Asn Lys Gln
385                 390                 395                 400
Phe Asn Tyr Lys Asp Pro Val Asn Gly Val Asp Ile Ala Tyr Ile Lys
                405                 410                 415
Ile Pro Asn Ala Gly Gln Met Gln Pro Val Lys Ala Phe Lys Ile His
            420                 425                 430
Asn Lys Ile Trp Val Ile Pro Glu Arg Asp Thr Phe Thr Asn Pro Glu
        435                 440                 445
Glu Gly Asp Leu Asn Pro Pro Glu Ala Lys Gln Val Pro Val Ser
450                 455                 460
Tyr Tyr Asp Ser Thr Tyr Leu Ser Thr Asp Asn Glu Lys Asp Asn Tyr
465                 470                 475                 480
Leu Lys Gly Val Thr Lys Leu Phe Glu Arg Ile Tyr Ser Thr Asp Leu
                485                 490                 495
Gly Arg Met Leu Leu Thr Ser Ile Val Arg Gly Ile Pro Phe Trp Gly
            500                 505                 510
Gly Ser Thr Ile Asp Thr Glu Leu Lys Val Ile Asp Thr Asn Cys Ile
        515                 520                 525
Asn Val Ile Gln Pro Asp Gly Ser Tyr Arg Ser Glu Glu Leu Asn Leu
530                 535                 540
Val Ile Ile Gly Pro Ser Ala Asp Ile Ile Gln Phe Glu Cys Lys Ser
545                 550                 555                 560
Phe Gly His Glu Val Leu Asn Leu Thr Arg Asn Gly Tyr Gly Ser Thr
                565                 570                 575
Gln Tyr Ile Arg Phe Ser Pro Asp Phe Thr Phe Gly Phe Glu Glu Ser
            580                 585                 590
Leu Glu Val Asp Thr Asn Pro Leu Leu Gly Ala Gly Lys Phe Ala Thr
        595                 600                 605
Asp Pro Ala Val Thr Leu Ala His Glu Leu Ile His Ala Gly His Arg
610                 615                 620
Leu Tyr Gly Ile Ala Ile Asn Pro Asn Arg Val Phe Lys Val Asn Thr
```

-continued

```
            625                 630                 635                 640
Asn Ala Tyr Tyr Glu Met Ser Gly Leu Glu Val Ser Phe Glu Glu Leu
                    645                 650                 655
Arg Thr Phe Gly Gly His Asp Ala Lys Phe Ile Asp Ser Leu Gln Glu
                    660                 665                 670
Asn Glu Phe Arg Leu Tyr Tyr Asn Lys Phe Lys Asp Ile Ala Ser
                    675                 680                 685
Thr Leu Asn Lys Ala Lys Ser Ile Val Gly Thr Thr Ala Ser Leu Gln
                    690                 695                 700
Tyr Met Lys Asn Val Phe Lys Glu Lys Tyr Leu Leu Ser Glu Asp Thr
705                 710                 715                 720
Ser Gly Lys Phe Ser Val Asp Lys Leu Lys Phe Asp Lys Leu Tyr Lys
                    725                 730                 735
Met Leu Thr Glu Ile Tyr Thr Glu Asp Asn Phe Val Lys Phe Phe Lys
                    740                 745                 750
Val Leu Asn Arg Lys Thr Tyr Leu Asn Phe Asp Lys Ala Val Phe Lys
                    755                 760                 765
Ile Asn Ile Val Pro Lys Val Asn Tyr Thr Ile Tyr Asp Gly Phe Asn
                    770                 775                 780
Leu Arg Asn Thr Asn Leu Ala Ala Asn Phe Asn Gly Gln Asn Thr Glu
785                 790                 795                 800
Ile Asn Asn Met Asn Phe Thr Lys Leu Lys Asn Phe Thr Gly Leu Phe
                    805                 810                 815
Glu Phe Tyr Lys Leu Leu Cys Val Asp Gly Ile Ile Thr Ser Lys Thr
                    820                 825                 830
Lys Ser Leu Ile Glu Gly Arg Asn Lys Ala Leu Asn Leu Gln Cys Arg
                    835                 840                 845
Glu Leu Leu Val Lys Asn Thr Asp Leu Pro Phe Ile Gly Asp Ile Ser
850                 855                 860
Asp Val Lys Thr Asp Ile Phe Leu Arg Lys Asp Ile Asn Glu Glu Thr
865                 870                 875                 880
Glu Val Ile Tyr Tyr Pro Asp Asn Val Ser Val Asp Gln Val Ile Leu
                    885                 890                 895
Ser Lys Asn Thr Ser Glu His Gly Gln Leu Asp Leu Leu Tyr Pro Ser
                    900                 905                 910
Ile Asp Ser Glu Ser Glu Ile Leu Pro Gly Glu Asn Gln Val Phe Tyr
                    915                 920                 925
Asp Asn Arg Thr Gln Asn Val Asp Tyr Leu Asn Ser Tyr Tyr Leu
                    930                 935                 940
Glu Ser Gln Lys Leu Ser Asp Asn Val Glu Asp Phe Thr Phe Thr Arg
945                 950                 955                 960
Ser Ile Glu Glu Ala Leu Asp Asn Ser Ala Lys Val Tyr Thr Tyr Phe
                    965                 970                 975
Pro Thr Leu Ala Asn Lys Val Asn Ala Gly Val Gln Gly Gly Leu Phe
                    980                 985                 990
Leu Met Trp Ala Asn Asp Val Val  Glu Asp Phe Thr Thr  Asn Ile Leu
                    995                1000                1005
Arg Lys  Asp Thr Leu Asp Lys  Ile Ser Asp Val Ser  Ala Ile Ile
         1010                1015                1020
Pro Tyr  Ile Gly Pro Ala Leu  Asn Ile Ser Asn Ser  Val Arg Arg
         1025                1030                1035
Gly Asn  Phe Thr Glu Ala Phe  Ala Val Thr Gly Val  Thr Ile Leu
         1040                1045                1050
```

-continued

```
Leu Glu Ala Phe Pro Glu Phe Thr Ile Pro Ala Leu Gly Ala Phe
    1055                1060                1065

Val Ile Tyr Ser Lys Val Gln Glu Arg Asn Glu Ile Ile Lys Thr
    1070                1075                1080

Ile Asp Asn Cys Leu Glu Gln Arg Ile Lys Arg Trp Lys Asp Ser
    1085                1090                1095

Tyr Glu Trp Met Met Gly Thr Trp Leu Ser Arg Ile Ile Thr Gln
    1100                1105                1110

Phe Asn Asn Ile Ser Tyr Gln Met Tyr Asp Ser Leu Asn Tyr Gln
    1115                1120                1125

Ala Gly Ala Ile Lys Ala Lys Ile Asp Leu Glu Tyr Lys Lys Tyr
    1130                1135                1140

Ser Gly Ser Asp Lys Glu Asn Ile Lys Ser Gln Val Glu Asn Leu
    1145                1150                1155

Lys Asn Ser Leu Asp Val Lys Ile Ser Glu Ala Met Asn Asn Ile
    1160                1165                1170

Asn Lys Phe Ile Arg Glu Cys Ser Val Thr Tyr Leu Phe Lys Asn
    1175                1180                1185

Met Leu Pro Lys Val Ile Asp Glu Leu Asn Glu Phe Asp Arg Asn
    1190                1195                1200

Thr Lys Ala Lys Leu Ile Asn Leu Ile Asp Ser His Asn Ile Ile
    1205                1210                1215

Leu Val Gly Glu Val Asp Lys Leu Lys Ala Lys Val Asn Asn Ser
    1220                1225                1230

Phe Gln Asn Thr Ile Pro Phe Asn Ile Phe Ser Tyr Thr Asn Asn
    1235                1240                1245

Ser Leu Leu Lys Asp Ile Ile Asn Glu Tyr Phe Asn Leu Glu Gly
    1250                1255                1260

Gly Gly Gly Ser Gly Gly Gly Ser Val Glu Thr Ile Ser Phe
    1265                1270                1275

Ser Phe Ser Glu Phe Glu Pro Gly Asn Asn Asp Leu Thr Leu Gln
    1280                1285                1290

Gly Ala Ala Ile Ile Thr Gln Ser Gly Val Leu Gln Leu Thr Lys
    1295                1300                1305

Ile Asn Gln Asn Gly Met Pro Ala Trp Asp Ser Thr Gly Arg Thr
    1310                1315                1320

Leu Tyr Thr Lys Pro Val His Ile Trp Asp Met Thr Thr Gly Thr
    1325                1330                1335

Val Ala Ser Phe Glu Thr Arg Phe Ser Phe Ser Ile Glu Gln Pro
    1340                1345                1350

Tyr Thr Arg Pro Leu Pro Ala Asp Gly Leu Val Phe Phe Met Gly
    1355                1360                1365

Pro Thr Lys Ser Lys Pro Ala Gln Gly Tyr Gly Tyr Leu Gly Val
    1370                1375                1380

Phe Asn Asn Ser Lys Gln Asp Asn Ser Tyr Gln Thr Leu Ala Val
    1385                1390                1395

Glu Phe Asp Thr Phe Ser Asn Pro Trp Asp Pro Gln Val Pro
    1400                1405                1410

His Ile Gly Ile Asp Val Asn Ser Ile Arg Ser Ile Lys Thr Gln
    1415                1420                1425

Pro Phe Gln Leu Asp Asn Gly Gln Val Ala Asn Val Val Ile Lys
    1430                1435                1440
```

| Tyr | Asp | Ala | Ser | Ser | Lys | Ile | Leu | Leu | Ala | Val | Leu | Val | Tyr | Pro |
| --- | --- | --- | --- | --- | --- | --- | --- | --- | --- | --- | --- | --- | --- | --- |
| 1445 | | | | | 1450 | | | | | 1455 | | | | |

| Ser | Ser | Gly | Ala | Ile | Tyr | Thr | Ile | Ala | Glu | Ile | Val | Asp | Val | Lys |
| --- | --- | --- | --- | --- | --- | --- | --- | --- | --- | --- | --- | --- | --- | --- |
| 1460 | | | | | 1465 | | | | | 1470 | | | | |

| Gln | Val | Leu | Pro | Glu | Trp | Val | Asp | Val | Gly | Leu | Ser | Gly | Ala | Thr |
| --- | --- | --- | --- | --- | --- | --- | --- | --- | --- | --- | --- | --- | --- | --- |
| 1475 | | | | | 1480 | | | | | 1485 | | | | |

| Gly | Ala | Gln | Arg | Asp | Ala | Ala | Glu | Thr | His | Asp | Val | Tyr | Ser | Trp |
| --- | --- | --- | --- | --- | --- | --- | --- | --- | --- | --- | --- | --- | --- | --- |
| 1490 | | | | | 1495 | | | | | 1500 | | | | |

| Ser | Phe | His | Ala | Ser | Leu | Pro | Glu | Thr | Asn | Asp | Lys | Leu |
| --- | --- | --- | --- | --- | --- | --- | --- | --- | --- | --- | --- | --- |
| 1505 | | | | | 1510 | | | | | 1515 | | |

<210> SEQ ID NO 24
<211> LENGTH: 4227
<212> TYPE: DNA
<213> ORGANISM: artificial sequence
<220> FEATURE:
<223> OTHER INFORMATION: Synthesised DNA sequence of IgA-Hn/A with
      Factor Xa activation
      site

<400> SEQUENCE: 24

| | |
| --- | --- |
| ggatccttgg tacgagatga cgttgactat caaattttcc gcgactttgc ggaaaataaa | 60 |
| ggtaagtttt tcgtcggcgc cacagacctg tccgtcaaaa ataagagagg ccagaacatc | 120 |
| ggtaacgcac tgagcaacgt ccctatgatt gattttagtg tagcggacgt taataaacgg | 180 |
| attgcaaccg tcgttgatcc gcagtatgct gtcagcgtca acatgctaa agcggaagtt | 240 |
| catacgttct attacgggca atataacggc ataacgatg tggctgataa agaaaatgaa | 300 |
| tatcgcgtgg tcgagcagaa caattacgaa ccgcacaaag cgtggggcgc gagtaattta | 360 |
| ggccgcctgg aggactataa catggcccgt ttcaataaat tcgtgaccga ggtagcaccg | 420 |
| atcgccccca cagatgctgg tggggcctg gatacctaca agataaaaa ccgcttctct | 480 |
| agcttcgtgc gcattggcgc cggtcgtcag ctcgtgtacg agaagggtgt ctatcaccag | 540 |
| gaaggtaatg aaaaggggta cgacctccgt gatttgtccc aggcgtatcg ctacgctatt | 600 |
| gccggaaccc cgtataaaga tattaatatc gatcaaacca tgaataccga aggcctaatt | 660 |
| ggtttcggga atcataataa gcaatatagc gcagaagagc taaagcaggc cctcagccaa | 720 |
| gatgcgttaa ccaattacgg agtgttaggc gatagcggca gtccgctgtt tgccttcgat | 780 |
| aaacagaaaa atcaatgggt gtttctgggc acttatgatt attgggccgg atatggtaaa | 840 |
| aagagctggc aggaatggaa tatttataaa aaggaattcg cagacaaaat caagcagcat | 900 |
| gacaacgcag gtacggtgaa ggggaacggc gaacatcact ggaagacgac cggcacgaat | 960 |
| agtcatatcg atcgacggc cgttcgcctg gcgaacaatg agggcgatgc aaacaatggg | 1020 |
| caaaacgtga cctttgagga caacggtacc ctggtcctta ccagaacat aaatcagggc | 1080 |
| gcgggaggct tgttctttaa aggcgactat actgttaagg gagcaaacaa tgacatcacc | 1140 |
| tggttagggg ccggtattga cgttgcggat ggaaaaaagg tggtttggca ggttaaaaac | 1200 |
| cctaacgggg accggctggc aaaaatcggc aaagggacat ggaaattaa tggtaccggt | 1260 |
| gtgaatcagg gtcagctgaa agtgggagat gggaccgtga ttctgaacca gaaagcagac | 1320 |
| gctgacaaaa aggtgcaagc ctttagccaa gtaggaattg ttagtggtcg tggcacactc | 1380 |
| gtcttgaact caagcaacca aataaatccg gataacctgt actttggatt tcgtggcgga | 1440 |
| cgcctggatg ctaacgggaa tgatctgacc tttgaacata tccgtaacgt tgacgagggt | 1500 |
| gcgcgcatag ttaatcataa tactgaccat gcatcaacta tcacccttga cgggaaaagt | 1560 |

```
ctgattacaa acccaaactc tctgtcagta cattccatcc agaatgatta tgatgaagac   1620
gattactcat actattaccg gccgcgtaga ccaattccac aaggtaaaga tctttattac   1680
aaaaattacc gttattacgc attaaaatcc ggagggcggc tgaatgcacc tatgccggaa   1740
aatggcgtgg ccgaaaacaa tgactggatt tttatgggtt atactcaaga agaggctcgc   1800
aaaaatgcaa tgaaccataa aaataaccga aggatcggtg atttcggcgg attttttcgat   1860 gaggaaaatg gtaaaggtca caatggtgcg ctgaatctaa attttaacgg caaaagtgcc   1920
cagaaacgtt tccttctgac tggtggcgct aatctgaatg gtaaaatcag tgtgacgcag   1980
ggtaacgtgc tgctttctgg ccggccaact ccgcatgcac gtgattttgt aaataaatcg   2040
agcgctcgta aagatgcgca ttttctaaa aataacgagg tcgtgtttga agatgactgg   2100
ataaatcgca ccttaaagc ggcagaaatc gcggttaatc agagtgcgag cttttcatcg   2160
ggtaggaatg tatctgatat tacagcaaac attacagcca ctgataatgc gaaggtcaac   2220
ctgggttata aaaacggtga tgaagtttgt gttcgatcgg attacacggg ctatgttacc   2280
tgcaacactg gcaatctgtc tgataaagcg cttaactctt ttgacgccac gcgcattaac   2340
gggaatgtga acctgaacca aaacgctgcc ttggtacttg gtaaggccgc gttgtggggt   2400 aaaaattcagg gccagggcaa ctcccgtgtg tctctgaacc agcactcgaa gtggcacctg   2460 acggggggact cgcaggtgca caacttgtcc ctggccgata gccatattca ccttaacaat   2520
gcgtccgatg cccagtcagc taataaatat catacgatca aaatcaatca cctctctggc   2580
aacggtcact ttcactactt aacggattta gcaaaaaact tagggataaa agtcctggta   2640
aaagaatcag cgagcggaca ttatcagtta catgtacaga acaaaacagg cgagccaaat   2700
caggaaggcc ttgacttatt tgatgcttca tcggtacaag atcgttccag actgttcgtt   2760
tcactcgcga atcactacgt tgatctgggt gcgctgcgct atactataaa gacggaaaat   2820
ggcataacac gcctctataa tccctatgcc ggtaacggcc gtccggtgaa acctgctccc   2880
tgcgtcgacg gcatcattac ctccaaaact aaatctctga tagaaggtag aaacaaagcg   2940
ctgaacctgc agtgtatcaa ggttaacaac tgggatttat tcttcagccc gagtgaagac   3000
aacttcacca acgacctgaa caaaggtgaa gaaatcacct cagatactaa catcgaagca   3060
gccgaagaaa acatctcgct ggacctgatc cagcagtact acctgacctt taatttcgac   3120
aacgagccgg aaaacatttc tatcgaaaac ctgagctctg atatcatcgg ccagctggaa   3180
ctgatgccga acatcgaacg tttcccaaac ggtaaaaagt acgagctgga caaatatacc   3240
atgttccact acctgcgcgc gcaggaattt gaacacggca atcccgtat cgcactgact   3300 aactccgtta acgaagctct gctcaacccg tcccgtgtat acaccttctt ctctagcgac   3360
tacgtgaaaa aggtcaacaa agcgactgaa gctgcaatgt tcttgggttg ggttgaacag   3420
cttgtttatg attttaccga cgagacgtcc gaagtatcta ctaccgacaa aattgcggat   3480
atcactatca tcatcccgta catcggtccg gctctgaaca ttggcaacat gctgtacaaa   3540
gacgacttcg ttggcgcact gatcttctcc ggtgcggtga tcctgctgga gttcatcccg   3600
gaaatcgcca tcccggtact gggcaccttt gctctggttt cttacattgc aaacaaggtt   3660
ctgactgtac aaaccatcga caacgcgctg agcaaacgta acgaaaaatg ggatgaagtt   3720
tacaaatata tcgtgaccaa ctggctggct aaggttaata ctcagatcga cctcatccgc   3780
aaaaaaatga agaagcact ggaaaaccag gcggaagcta ccaaggcaat cattaactac   3840
cagtacaacc agtacaccga ggaagaaaaa aacaacatca acttcaacat cgacgatctg   3900
tcctctaaac tgaacgaatc catcaacaaa gctatgatca acatcaacaa gttcctgaac   3960
```

```
cagtgctctg taagctatct gatgaactcc atgatcccgt acggtgttaa acgtctggag    4020
gacttcgatg cgtctctgaa agacgccctg ctgaaataca tttacgacaa ccgtggcact    4080
ctgatcggtc aggttgatcg tctgaaggac aaagtgaaca ataccttatc gaccgacatc    4140
ccttttcagc tcagtaaata tgtcgataac caacgccttt tgtccacttt caccgaatac    4200
atcaaaggtc tagactgata gaagctt                                         4227

<210> SEQ ID NO 25
<211> LENGTH: 6156
<212> TYPE: DNA
<213> ORGANISM: Artificial sequence
<220> FEATURE:
<223> OTHER INFORMATION: DNA sequence of ORF from pMAL-IgA-Hn/A-
      GSspacer-ECL

<400> SEQUENCE: 25
atgaaaatcg aagaaggtaa actggtaatc tggattaacg gcgataaagg ctataacggt      60
ctcgctgaag tcggtaagaa attcgagaaa gataccggaa ttaaagtcac cgttgagcat     120
ccggataaac tggaagagaa attcccacag gttgcggcaa ctggcgatgg ccctgacatt     180
atcttctggg cacacgaccg ctttggtggc tacgctcaat ctggcctgtt ggctgaaatc     240
accccggaca aagcgttcca ggacaagctg tatccgttta cctgggatgc cgtacgttac     300
aacggcaagc tgattgctta cccgatcgct gttgaagcgt tatcgctgat ttataacaaa     360
gatctgctgc cgaacccgcc aaaaacctgg gaagagatcc cggcgctgga taagaaactg     420
aaagcgaaag gtaagagcgc gctgatgttc aacctgcaag aaccgtactt cacctggccg     480
ctgattgctg ctgacggggg ttatgcgttc aagtatgaaa acggcaagta cgacattaaa     540
gacgtgggcg tggataacgc tggcgcgaaa gcgggtctga ccttcctggt tgacctgatt     600
aaaaacaaac acatgaatgc agacaccgat tactccatcg cagaagctgc ctttaataaa     660
ggcgaaacag cgatgaccat caacggcccg tgggcatggt ccaacatcga caccagcaaa     720
gtgaattatg gtgtaacggt actgccgacc ttcaagggtc aaccatccaa accgttcgtt     780
ggcgtgctga gcgcaggtat taacgccgcc agtccgaaca aagagctggc aaaagagttc     840
ctcgaaaact atctgctgac tgatgaaggt ctggaagcgg ttaataaaga caaaccgctg     900
ggtgccgtag cgctgaagtc ttacgaggaa gagttggcga agatccacg tattgccgcc     960 actatggaaa acgcccagaa aggtgaaatc atgccgaaca tcccgcagat gtccgctttc    1020
tggtatgccg tgcgtactgc ggtgatcaac gccgccagcg gtcgtcagac tgtcgatgaa    1080
gccctgaaag acgcgcagac taattcgagc tcaacaaca caacaataa caataacaac    1140 aacctcggga tcgagggaag gatttcagaa ttcggatcct ggtacgaga tgacgttgac    1200 tatcaaattt ccgcgactt tgcggaaaat aaaggtaagt ttttcgtcgg cgccacagac    1260
ctgtccgtca aaataagag aggccagaac atcggtaacg cactgagcaa cgtccctatg    1320
attgatttta gtgtagcgga cgttaataaa cggattgcaa ccgtcgttga tccgcagtat    1380
gctgtcagcg tcaaacatgc taagcggaa gttcatacgt ctattacggg caatataac    1440 ggccataacg atgtggctga taagaaat gaatatcgcg tggtcgagca gaacaattac    1500
gaaccgcaca aagcgtgggg gcgagtaat ttaggccgcc tggaggacta taacatggcc    1560
cgtttcaata attcgtgac cgaggtagca ccgatcgccc ccacagatgc tggtggggc    1620 ctggatacct acaaagataa aaaccgcttc tctagcttcg tgcgcattgg cgccggtcgt    1680
cagctcgtgt acgagaaggg tgtctatcac caggaaggta atgaaaaggg gtacgacctc    1740
```

-continued

```
cgtgatttgt cccaggcgta tcgctacgct attgccggaa ccccgtataa agatattaat    1800
atcgatcaaa ccatgaatac cgaaggccta attggtttcg ggaatcataa taagcaatat    1860
agcgcagaag agctaaagca ggccctcagc caagatgcgt taaccaatta cggagtgtta    1920
ggcgatagcg gcagtccgct gtttgccttc gataaacaga aaaatcaatg ggtgtttctg    1980
ggcacttatg attattgggc cggatatggt aaaaagagct ggcaggaatg gaatatttat    2040
aaaaaggaat tcgcagacaa aatcaagcag catgacaacg caggtacggt gaaggggaac    2100
ggcgaacatc actggaagac gaccggcacg aatagtcata tcggatcgac ggccgttcgc    2160
ctggcgaaca atgagggcga tgcaaacaat gggcaaaacg tgacctttga ggacaacggt    2220
accctggtcc ttaaccagaa cataaatcag ggcgcgggag gcttgttctt taaaggcgac    2280
tatactgtta agggagcaaa caatgacatc acctggttag gggccggtat tgacgttgcg    2340
gatgaaaaaa aggtggtttg gcaggttaaa aaccctaacg gggaccggct ggcaaaaatc    2400
ggcaaaggga cattggaaat taatggtacc ggtgtgaatc agggtcagct gaaagtggga    2460
gatgggaccg tgattctgaa ccagaaagca gacgctgaca aaaaggtgca agcctttagc    2520
caagtaggaa ttgttagtgg tcgtggcaca ctcgtcttga actcaagcaa ccaaataaat    2580
ccggataacc tgtactttgg atttcgtggc ggacgcctgg atgctaacgg gaatgatctg    2640
acctttgaac atatccgtaa cgttgacgag ggtgcgcgca tagttaatca taatactgac    2700
catgcatcaa ctatcacctt gaccgggaaa agtctgatta caaacccaaa ctctctgtca    2760
gtacattcca tccagaatga ttatgatgaa gacgattact catactatta ccggccgcgt    2820
agaccaattc cacaaggtaa agatctttat tacaaaaatt accgttatta cgcattaaaa    2880
tccggagggc ggctgaatgc acctatgccg gaaaatggcg tggccgaaaa caatgactgg    2940
attttatgg gttatactca agaagaggct cgcaaaaatg caatgaacca taaaaataac    3000
cgaaggatcg gtgatttcgg cggatttttc gatgaggaaa atggtaaagg tcacaatggt    3060
gcgctgaatc taaattttaa cggcaaaagt gcccagaaac gtttccttct gactggtggc    3120
gctaatctga atggtaaaat cagtgtgacg cagggtaacg tgctgctttc tggccggcca    3180
actccgcatg cacgtgattt tgtaaataaa tcgagcgctc gtaaagatgc gcattttttct   3240
aaaaataacg aggtcgtgtt tgaagatgac tggataaatc gcacctttaa agcggcagaa    3300
atcgcggtta atcagagtgc gagcttttca tcgggtagga atgtatctga tattacagca    3360
aacattacag ccactgataa tgcgaaggtc aacctgggtt ataaaaacgg tgatgaagtt    3420
tgtgttcgat cggattacac gggctatgtt acctgcaaca ctggcaatct gtctgataaa    3480
gcgcttaact cttttgacgc cacgcgcatt aacgggaatg tgaacctgaa ccaaaacgct    3540
gccttggtac ttggtaaggc cgcgttgtgg ggtaaaattc agggccaggg caactcccgt    3600
gtgtctctga accagcactc gaagtggcac ctgacgggg actcgcaggt gcacaacttg    3660
tccctggccg atagccatat tcaccttaac aatgcgtccg atgcccagtc agctaataaa    3720
tatcatacga tcaaaatcaa tcacctctct ggcaacggtc actttcacta cttaacggat    3780
ttagcaaaaa acttaggggga taaagtcctg gtaaaagaat cagcgagcgg acattatcag    3840
ttacatgtac agaacaaaac aggcgagcca atcaggaag gccttgactt atttgatgct    3900
tcatcggtac aagatcgttc cagactgttc gtttcactcg cgaatcacta cgttgatctg    3960
ggtgcgctgc gctatactat aaagacgaaa aatggcataa cacgcctcta taatccctat    4020
gccggtaacg gccgtccggt gaaacctgct ccctgcgtcg acggcatcat tacctccaaa    4080
```

```
actaaatctc tgatagaagg tagaaacaaa gcgctgaacc tgcagtgtat caaggttaac    4140
aactgggatt tattcttcag cccgagtgaa gacaacttca ccaacgacct gaacaaaggt    4200
gaagaaatca cctcagatac taacatcgaa gcagccgaag aaaacatctc gctggacctg    4260
atccagcagt actacctgac ctttaatttc gacaacgagc cggaaaacat ttctatcgaa    4320
aacctgagct ctgatatcat cggccagctg gaactgatgc cgaacatcga acgtttccca    4380
aacggtaaaa agtacgagct ggacaaatat accatgttcc actacctgcg cgcgcaggaa    4440
tttgaacacg gcaaatcccg tatcgcactg actaactccg ttaacgaagc tctgctcaac    4500
ccgtcccgtg tatacacctt cttctctagc gactacgtga aaaaggtcaa caaagcgact    4560
gaagctgcaa tgttcttggg ttgggttgaa cagcttgttt atgattttac cgacgagacg    4620
tccgaagtat ctactaccga caaaattgcg atatcacta tcatcatccc gtacatcggt    4680
ccggctctga acattggcaa catgctgtac aaagacgact cgttggcgc actgatcttc    4740 tccggtgcgg tgatcctgct ggagttcatc ccggaaatcg ccatcccggt actgggcacc    4800
tttgctctgg tttcttacat tgcaaacaag gttctgactg tacaaaccat cgacaacgcg    4860
ctgagcaaac gtaacgaaaa atgggatgaa gtttacaaat atatcgtgac caactggctg    4920
gctaaggtta atactcagat cgacctcatc cgcaaaaaaa tgaaagaagc actggaaaac    4980
caggcggaag ctaccaaggc aatcattaac taccagtaca accagtacac cgaggaagaa    5040
aaaaacaaca tcaacttcaa catcgacgat ctgtcctcta aactgaacga atccatcaac    5100
aaagctatga tcaacatcaa caagttcctg aaccagtgct ctgtaagcta tctgatgaac    5160
tccatgatcc cgtacggtgt taaacgtctg gaggacttcg atgcgtctct gaaagacgcc    5220
ctgctgaaat acatttacga caaccgtggc actctgatcg gtcaggttga tcgtctgaag    5280
gacaaagtga acaataccct atcgaccgac atcccttttc agctcagtaa atatgtcgat    5340
aaccaacgcc ttttgtccac tttcaccgaa tacatcaaag gtctagaagg tggcggtggg    5400
tccggtggcg gtggctcagt ggaaaccata tcgtttagct tcagtgagtt tgaaccgggt    5460
aacaacgatt tgaccttgca aggtgcagcc attattacac aatctggggt tttacaactc    5520
accaagatta atcaaaatgg catgccggct tgggactcaa cgggccgaac tctatatact    5580
aaacctgtgc acatttggga tatgaccaca ggcactgtgg ccagctttga aactagattc    5640
tccttttcca ttgaacaacc ctatacacgc ccactccccg ctgatggttt agtattcttt    5700
atgggaccaa caaagtccaa gccagctcaa ggttatggat acctcggagt attcaacaac    5760
tcaaaacagg ataactcata ccaaacactt gctgttgagt ttgacacttt cagtaaccca    5820
tgggaccctc cccaggttcc acacattgga atcgatgtca actccattcg atccatcaaa    5880
acccaacctt tcaattgga caatggccaa gttgccaatg ttgtcataaa atatgatgct    5940
tcctccaaaa tcttacttgc cgtgttggtt tacccttcca gtggagccat ttacaccatc    6000
gctgaaattg tggatgtgaa gcaagttctt cctgagtggg tcgacgttgg tctctcgggt    6060
gcaaccggtg cacagcgaga cgccgctgag acacacgacg tttattcttg gtcattccat    6120
gcctcgttgc cagaaacaaa cgattaatga aagctt                             6156
```

<210> SEQ ID NO 26
<211> LENGTH: 2050
<212> TYPE: PRT
<213> ORGANISM: Artificial Sequence
<220> FEATURE:
<223> OTHER INFORMATION: Protein sequence of ORF from pMAL-IgA-Hn/A-GSspacer-ECL

```
<400> SEQUENCE: 26

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
        370                 375                 380

Glu Gly Arg Ile Ser Glu Phe Gly Ser Leu Val Arg Asp Asp Val Asp
385                 390                 395                 400

Tyr Gln Ile Phe Arg Asp Phe Ala Glu Asn Lys Gly Lys Phe Phe Val
                405                 410                 415
```

-continued

Gly Ala Thr Asp Leu Ser Val Lys Asn Lys Arg Gly Gln Asn Ile Gly
            420                 425                 430

Asn Ala Leu Ser Asn Val Pro Met Ile Asp Phe Ser Val Ala Asp Val
            435                 440                 445

Asn Lys Arg Ile Ala Thr Val Val Asp Pro Gln Tyr Ala Val Ser Val
450                 455                 460

Lys His Ala Lys Ala Glu Val His Thr Phe Tyr Tyr Gly Gln Tyr Asn
465                 470                 475                 480

Gly His Asn Asp Val Ala Asp Lys Glu Asn Glu Tyr Arg Val Val Glu
            485                 490                 495

Gln Asn Asn Tyr Glu Pro His Lys Ala Trp Gly Ala Ser Asn Leu Gly
            500                 505                 510

Arg Leu Glu Asp Tyr Asn Met Ala Arg Phe Asn Lys Phe Val Thr Glu
            515                 520                 525

Val Ala Pro Ile Ala Pro Thr Asp Ala Gly Gly Leu Asp Thr Tyr
            530                 535                 540

Lys Asp Lys Asn Arg Phe Ser Ser Phe Val Arg Ile Gly Ala Gly Arg
545                 550                 555                 560

Gln Leu Val Tyr Glu Lys Gly Val Tyr His Gln Gly Asn Glu Lys
            565                 570                 575

Gly Tyr Asp Leu Arg Asp Leu Ser Gln Ala Tyr Arg Tyr Ala Ile Ala
            580                 585                 590

Gly Thr Pro Tyr Lys Asp Ile Asn Ile Asp Gln Thr Met Asn Thr Glu
            595                 600                 605

Gly Leu Ile Gly Phe Gly Asn His Asn Lys Gln Tyr Ser Ala Glu Glu
            610                 615                 620

Leu Lys Gln Ala Leu Ser Gln Asp Ala Leu Thr Asn Tyr Gly Val Leu
625                 630                 635                 640

Gly Asp Ser Gly Ser Pro Leu Phe Ala Phe Asp Lys Gln Lys Asn Gln
            645                 650                 655

Trp Val Phe Leu Gly Thr Tyr Asp Tyr Trp Ala Gly Tyr Gly Lys Lys
            660                 665                 670

Ser Trp Gln Glu Trp Asn Ile Tyr Lys Lys Glu Phe Ala Asp Lys Ile
            675                 680                 685

Lys Gln His Asp Asn Ala Gly Thr Val Lys Gly Asn Gly Glu His His
            690                 695                 700

Trp Lys Thr Thr Gly Thr Asn Ser His Ile Gly Ser Thr Ala Val Arg
705                 710                 715                 720

Leu Ala Asn Asn Glu Gly Asp Ala Asn Asn Gly Gln Asn Val Thr Phe
            725                 730                 735

Glu Asp Asn Gly Thr Leu Val Leu Asn Gln Asn Ile Asn Gln Gly Ala
            740                 745                 750

Gly Gly Leu Phe Phe Lys Gly Asp Tyr Thr Val Lys Gly Ala Asn Asn
            755                 760                 765

Asp Ile Thr Trp Leu Gly Ala Gly Ile Asp Val Ala Asp Gly Lys Lys
770                 775                 780

Val Val Trp Gln Val Lys Asn Pro Asn Gly Asp Arg Leu Ala Lys Ile
785                 790                 795                 800

Gly Lys Gly Thr Leu Glu Ile Asn Gly Thr Val Asn Gln Gly Gln
            805                 810                 815

Leu Lys Val Gly Asp Gly Thr Val Ile Leu Asn Gln Lys Ala Asp Ala
            820                 825                 830

-continued

Asp Lys Lys Val Gln Ala Phe Ser Gln Val Gly Ile Val Ser Gly Arg
        835                 840                 845

Gly Thr Leu Val Leu Asn Ser Ser Asn Gln Ile Asn Pro Asp Asn Leu
850                 855                 860

Tyr Phe Gly Phe Arg Gly Gly Arg Leu Asp Ala Asn Gly Asn Asp Leu
865                 870                 875                 880

Thr Phe Glu His Ile Arg Asn Val Asp Glu Gly Ala Arg Ile Val Asn
            885                 890                 895

His Asn Thr Asp His Ala Ser Thr Ile Thr Leu Thr Gly Lys Ser Leu
            900                 905                 910

Ile Thr Asn Pro Asn Ser Leu Ser Val His Ser Ile Gln Asn Asp Tyr
            915                 920                 925

Asp Glu Asp Asp Tyr Ser Tyr Tyr Tyr Arg Pro Arg Arg Pro Ile Pro
930                 935                 940

Gln Gly Lys Asp Leu Tyr Tyr Lys Asn Tyr Arg Tyr Tyr Ala Leu Lys
945                 950                 955                 960

Ser Gly Gly Arg Leu Asn Ala Pro Met Pro Glu Asn Gly Val Ala Glu
            965                 970                 975

Asn Asn Asp Trp Ile Phe Met Gly Tyr Thr Gln Glu Glu Ala Arg Lys
            980                 985                 990

Asn Ala Met Asn His Lys Asn Asn Arg Arg Ile Gly Asp Phe Gly Gly
            995                 1000                1005

Phe Phe Asp Glu Glu Asn Gly Lys Gly His Asn Gly Ala Leu Asn
    1010                1015                1020

Leu Asn Phe Asn Gly Lys Ser Ala Gln Lys Arg Phe Leu Leu Thr
    1025                1030                1035

Gly Gly Ala Asn Leu Asn Gly Lys Ile Ser Val Thr Gln Gly Asn
    1040                1045                1050

Val Leu Leu Ser Gly Arg Pro Thr Pro His Ala Arg Asp Phe Val
    1055                1060                1065

Asn Lys Ser Ser Ala Arg Lys Asp Ala His Phe Ser Lys Asn Asn
    1070                1075                1080

Glu Val Val Phe Glu Asp Asp Trp Ile Asn Arg Thr Phe Lys Ala
    1085                1090                1095

Ala Glu Ile Ala Val Asn Gln Ser Ala Ser Phe Ser Ser Gly Arg
    1100                1105                1110

Asn Val Ser Asp Ile Thr Ala Asn Ile Thr Ala Thr Asp Asn Ala
    1115                1120                1125

Lys Val Asn Leu Gly Tyr Lys Asn Gly Asp Glu Val Cys Val Arg
    1130                1135                1140

Ser Asp Tyr Thr Gly Tyr Val Thr Cys Asn Thr Gly Asn Leu Ser
    1145                1150                1155

Asp Lys Ala Leu Asn Ser Phe Asp Ala Thr Arg Ile Asn Gly Asn
    1160                1165                1170

Val Asn Leu Asn Gln Asn Ala Ala Leu Val Leu Gly Lys Ala Ala
    1175                1180                1185

Leu Trp Gly Lys Ile Gln Gly Gln Gly Asn Ser Arg Val Ser Leu
    1190                1195                1200

Asn Gln His Ser Lys Trp His Leu Thr Gly Asp Ser Gln Val His
    1205                1210                1215

Asn Leu Ser Leu Ala Asp Ser His Ile His Leu Asn Asn Ala Ser
    1220                1225                1230

Asp Ala Gln Ser Ala Asn Lys Tyr His Thr Ile Lys Ile Asn His

-continued

```
          1235              1240              1245
Leu Ser Gly Asn Gly His Phe His Tyr Leu Thr Asp Leu Ala Lys
    1250              1255              1260
Asn Leu Gly Asp Lys Val Leu Val Lys Glu Ser Ala Ser Gly His
    1265              1270              1275
Tyr Gln Leu His Val Gln Asn Lys Thr Gly Glu Pro Asn Gln Glu
    1280              1285              1290
Gly Leu Asp Leu Phe Asp Ala Ser Ser Val Gln Asp Arg Ser Arg
    1295              1300              1305
Leu Phe Val Ser Leu Ala Asn His Tyr Val Asp Leu Gly Ala Leu
    1310              1315              1320
Arg Tyr Thr Ile Lys Thr Glu Asn Gly Ile Thr Arg Leu Tyr Asn
    1325              1330              1335
Pro Tyr Ala Gly Asn Gly Arg Pro Val Lys Pro Ala Pro Cys Val
    1340              1345              1350
Asp Gly Ile Ile Thr Ser Lys Thr Lys Ser Leu Ile Glu Gly Arg
    1355              1360              1365
Asn Lys Ala Leu Asn Leu Gln Cys Ile Lys Val Asn Asn Trp Asp
    1370              1375              1380
Leu Phe Phe Ser Pro Ser Glu Asp Asn Phe Thr Asn Asp Leu Asn
    1385              1390              1395
Lys Gly Glu Glu Ile Thr Ser Asp Thr Asn Ile Glu Ala Ala Glu
    1400              1405              1410
Glu Asn Ile Ser Leu Asp Leu Ile Gln Gln Tyr Tyr Leu Thr Phe
    1415              1420              1425
Asn Phe Asp Asn Glu Pro Glu Asn Ile Ser Ile Glu Asn Leu Ser
    1430              1435              1440
Ser Asp Ile Ile Gly Gln Leu Glu Leu Met Pro Asn Ile Glu Arg
    1445              1450              1455
Phe Pro Asn Gly Lys Lys Tyr Glu Leu Asp Lys Tyr Thr Met Phe
    1460              1465              1470
His Tyr Leu Arg Ala Gln Glu Phe Glu His Gly Lys Ser Arg Ile
    1475              1480              1485
Ala Leu Thr Asn Ser Val Asn Glu Ala Leu Leu Asn Pro Ser Arg
    1490              1495              1500
Val Tyr Thr Phe Phe Ser Ser Asp Tyr Val Lys Lys Val Asn Lys
    1505              1510              1515
Ala Thr Glu Ala Ala Met Phe Leu Gly Trp Val Glu Gln Leu Val
    1520              1525              1530
Tyr Asp Phe Thr Asp Glu Thr Ser Glu Val Ser Thr Thr Asp Lys
    1535              1540              1545
Ile Ala Asp Ile Thr Ile Ile Pro Tyr Ile Gly Pro Ala Leu
    1550              1555              1560
Asn Ile Gly Asn Met Leu Tyr Lys Asp Asp Phe Val Gly Ala Leu
    1565              1570              1575
Ile Phe Ser Gly Ala Val Ile Leu Leu Glu Phe Ile Pro Glu Ile
    1580              1585              1590
Ala Ile Pro Val Leu Gly Thr Phe Ala Leu Val Ser Tyr Ile Ala
    1595              1600              1605
Asn Lys Val Leu Thr Val Gln Thr Ile Asp Asn Ala Leu Ser Lys
    1610              1615              1620
Arg Asn Glu Lys Trp Asp Glu Val Tyr Lys Tyr Ile Val Thr Asn
    1625              1630              1635
```

-continued

```
Trp Leu Ala Lys Val Asn Thr Gln Ile Asp Leu Ile Arg Lys Lys
1640                1645                1650

Met Lys Glu Ala Leu Glu Asn Gln Ala Glu Ala Thr Lys Ala Ile
    1655                1660                1665

Ile Asn Tyr Gln Tyr Asn Gln Tyr Thr Glu Glu Glu Lys Asn Asn
    1670                1675                1680

Ile Asn Phe Asn Ile Asp Asp Leu Ser Ser Lys Leu Asn Glu Ser
    1685                1690                1695

Ile Asn Lys Ala Met Ile Asn Ile Asn Lys Phe Leu Asn Gln Cys
    1700                1705                1710

Ser Val Ser Tyr Leu Met Asn Ser Met Ile Pro Tyr Gly Val Lys
    1715                1720                1725

Arg Leu Glu Asp Phe Asp Ala Ser Leu Lys Asp Ala Leu Leu Lys
    1730                1735                1740

Tyr Ile Tyr Asp Asn Arg Gly Thr Leu Ile Gly Gln Val Asp Arg
    1745                1750                1755

Leu Lys Asp Lys Val Asn Asn Thr Leu Ser Thr Asp Ile Pro Phe
    1760                1765                1770

Gln Leu Ser Lys Tyr Val Asp Asn Gln Arg Leu Leu Ser Thr Phe
    1775                1780                1785

Thr Glu Tyr Ile Lys Gly Leu Glu Gly Gly Gly Ser Gly Gly
    1790                1795                1800

Gly Gly Ser Val Glu Thr Ile Ser Phe Ser Phe Ser Glu Phe Glu
    1805                1810                1815

Pro Gly Asn Asn Asp Leu Thr Leu Gln Gly Ala Ala Ile Ile Thr
    1820                1825                1830

Gln Ser Gly Val Leu Gln Leu Thr Lys Ile Asn Gln Asn Gly Met
    1835                1840                1845

Pro Ala Trp Asp Ser Thr Gly Arg Thr Leu Tyr Thr Lys Pro Val
    1850                1855                1860

His Ile Trp Asp Met Thr Thr Gly Thr Val Ala Ser Phe Glu Thr
    1865                1870                1875

Arg Phe Ser Phe Ser Ile Glu Gln Pro Tyr Thr Arg Pro Leu Pro
    1880                1885                1890

Ala Asp Gly Leu Val Phe Phe Met Gly Pro Thr Lys Ser Lys Pro
    1895                1900                1905

Ala Gln Gly Tyr Gly Tyr Leu Gly Val Phe Asn Asn Ser Lys Gln
    1910                1915                1920

Asp Asn Ser Tyr Gln Thr Leu Ala Val Glu Phe Asp Thr Phe Ser
    1925                1930                1935

Asn Pro Trp Asp Pro Pro Gln Val Pro His Ile Gly Ile Asp Val
    1940                1945                1950

Asn Ser Ile Arg Ser Ile Lys Thr Gln Pro Phe Gln Leu Asp Asn
    1955                1960                1965

Gly Gln Val Ala Asn Val Val Ile Lys Tyr Asp Ala Ser Ser Lys
    1970                1975                1980

Ile Leu Leu Ala Val Leu Val Tyr Pro Ser Ser Gly Ala Ile Tyr
    1985                1990                1995

Thr Ile Ala Glu Ile Val Asp Val Lys Gln Val Leu Pro Glu Trp
    2000                2005                2010

Val Asp Val Gly Leu Ser Gly Ala Thr Gly Ala Gln Arg Asp Ala
    2015                2020                2025
```

```
Ala Glu Thr His Asp Val Tyr Ser Trp Ser Phe His Ala Ser Leu
    2030            2035            2040

Pro Glu Thr Asn Asp Lys Leu
    2045            2050

<210> SEQ ID NO 27
<211> LENGTH: 2055
<212> TYPE: DNA
<213> ORGANISM: Artificial sequence
<220> FEATURE:
<223> OTHER INFORMATION: Synthesised DNA sequence of LC/A-HA with
      Factor Xa activation site

<400> SEQUENCE: 27
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gatacctttaa ctaacccgga agaaggtgac    180
ctgaacccgc caccggaagc gaaacaggtg ccggtatctt actatgactc cacctacctg    240
tctaccgata cgaaaagga caactacctg aaaggtgtta ctaaactgtt cgagcgtatt      300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg ttcctatcg ttccgaagaa ctgaacctgg tgatcatcgg cccgtctgct      480
gatatcatcc agttcgagtg taagagcttt ggtcacgaag ttctgaacct cacccgtaac    540
ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaagcgaaat ccatcgtggg taccactgct ctctctccagt acatgaagaa cgtttttaaa    960
gaaaaatacc tgctcagcga agacaccctcc ggcaaattct ctgtagacaa gttgaaattc    1020
gataaacttt acaaaatgct gactgaaatt tacaccgaag acaacttcgt taagttctt    1080 aaagttctga accgcaaaac ctatctgaac ttcgacaagg cagtattcaa aatcaacatc     1140
gtgccgaaag ttaactacac tatctacgat ggtttcaacc tgcgtaacac caacctggct    1200 gctaattta acggccagaa cacggaaatc aacaacatga cttcacaaa actgaaaaac       1260 ttcactggtc tgttcgagtt ttacaagctg ctgtgcgtcg acggcatcat tacctccaaa    1320
actaaatctc tgatagaagg tagaaacaaa gcgctgaacc tgcagtgtgg cctgtttggt    1380
gctatcgccg gatttataga gggcggttgg acagggatga ttgacgggtg gtacggatat    1440
caccatcaga atgaacaggg ttctggttat gccgcggatc aaaagtccac gcagaacgcg    1500
atcaacggca tcaccaataa agtcaattcg gtaatcgaaa aaatgaacat tcaatttacc    1560
gctgtgggca agaatttaa taaactggag aagcgtatgg aaaatctgaa caaaaaggta    1620
gatgacggct tcctggacat ttggacttat aatgccgaat tactggtcct ctctgagaat    1680
gaacgtaccc tggacttcca tgattcgaac gtcaagaact atatgaaaa agttaaaagt    1740 caactgaaaa ataacgcaaa ggagattgg aacggatgtt ttgaattcta tcacaaatgc    1800
gataacgaat gcatggaatc agttcgcaat ggcacttacg attacccgaa atattccgag    1860
```

| | |
|---|---|
| gaaagcaaat tgaaccgcga aaaagttgat ggggtgaaat tggagtcaat gggtatctac | 1920 |
| cagatcctcg caatttattc tacggtggca tctagcctgg tgcttctggt tagtctaggc | 1980 |
| gcgataagtt tctggatgtg tagcaatggt agcttacagt gccggatttg tattggtcta | 2040 |
| gactgataga agctt | 2055 |

<210> SEQ ID NO 28
<211> LENGTH: 4017
<212> TYPE: DNA
<213> ORGANISM: Artificial sequence
<220> FEATURE:
<223> OTHER INFORMATION: DNA sequence of ORF from pMAL-LC/A-HA-
      GSspacer-SBA

<400> SEQUENCE: 28

| | |
|---|---|
| atgaaaatcg aagaaggtaa actggtaatc tggattaacg gcgataaagg ctataacggt | 60 |
| ctcgctgaag tcggtaagaa attcgagaaa gataccggaa ttaaagtcac cgttgagcat | 120 |
| ccggataaac tggaagagaa attcccacag gttgcggcaa ctggcgatgg ccctgacatt | 180 |
| atcttctggg cacacgaccg ctttggtggc tacgctcaat ctggcctgtt ggctgaaatc | 240 |
| accccggaca aagcgttcca ggacaagctg tatccgttta cctgggatgc cgtacgttac | 300 |
| aacggcaagc tgattgctta cccgatcgct gttgaagcgt atcgctgat ttataacaaa | 360 |
| gatctgctgc cgaacccgcc aaaaacctgg aagagatcc cggcgctgga taagaactg | 420 |
| aaagcgaaag gtaagagcgc gctgatgttc aacctgcaag aaccgtactt cacctggccg | 480 |
| ctgattgctg ctgacggggg ttatgcgttc aagtatgaaa acggcaagta cgacattaaa | 540 |
| gacgtgggcg tggataacgc tggcgcgaaa gcgggtctga ccttcctggt tgacctgatt | 600 |
| aaaaacaaac acatgaatgc agacaccgat tactccatcg cagaagctgc ctttaataaa | 660 |
| ggcgaaacag cgatgaccat caacggcccg tgggcatggt ccaacatcga caccagcaaa | 720 |
| gtgaattatg gtgtaacggt actgccgacc ttcaagggtc aaccatccaa accgttcgtt | 780 |
| ggcgtgctga gcgcaggtat taacgccgcc agtccgaaca agagctggc aaaagagttc | 840 |
| ctcgaaaact atctgctgac tgatgaaggt ctggaagcgg ttaataaga caaaccgctg | 900 |
| ggtgccgtag cgctgaagtc ttacgaggaa gagttggcga agatccacg tattgccgcc | 960 |
| actatggaaa acgcccagaa aggtgaaatc atgccgaaca tcccgcagat gtccgctttc | 1020 |
| tggtatgccg tgcgtactgc ggtgatcaac gccgccagcg gtcgtcagac tgtcgatgaa | 1080 |
| gccctgaaag acgcgcagac taattcgagc tcgaacaaca caacaataa caataacaac | 1140 |
| aacctcggga tcgagggaag gatttcagaa ttcggatcca tggagttcgt taacaaacag | 1200 |
| ttcaactata aagacccagt taacggtgtt gacattgctt acatcaaaat cccgaacgct | 1260 |
| ggccagatgc agccggtaaa ggcattcaaa atccacaaca aaatctgggt tatcccggaa | 1320 |
| cgtgatacct ttactaaccc ggaagaaggt gacctgaacc cgccaccgga agcgaaacag | 1380 |
| gtgccggtat cttactatga ctccacctac ctgtctaccg ataacgaaaa ggacaactac | 1440 |
| ctgaaaggtg ttactaaact gttcgagcgt atttactcca ccgacctggg ccgtatgctg | 1500 |
| ctgactagca tcgttcgcgg tatcccgttc tggggcggtt ctaccatcga taccgaactg | 1560 |
| aaagtaatcg acactaactg catcaacgtt attcagccgg acggttccta tcgttccgaa | 1620 |
| gaactgaacc tggtgatcat cggcccgtct gctgatatca tccagttcga gtgtaagagc | 1680 |
| tttggtcacg aagttctgaa cctcacccgt aacggctacg gttccactca gtacatccgt | 1740 |
| ttctctccgg acttcacctt cggttttgaa gaatccctgg aagtagacac gaacccactg | 1800 |

```
ctgggcgctg gtaaattcgc aactgatcct gcggttaccc tggctcacga actgattcat    1860
gcaggccacc gcctgtacgg tatcgccatc aatccgaacc gtgtcttcaa agttaacacc    1920
aacgcgtatt acgagatgtc cggtctggaa gttagcttcg aagaactgcg tacttttggc    1980
ggtcacgacg ctaaattcat cgactctctg caagaaaacg agttccgtct gtactactat    2040
aacaagttca agatatcgc atccaccctg aacaaagcga atccatcgt gggtaccact    2100 gcttctctcc agtacatgaa gaacgttttt aaagaaaaat acctgctcag cgaagacacc    2160
tccggcaaat tctctgtaga caagttgaaa ttcgataaac tttacaaaat gctgactgaa    2220 atttacaccaa agacaactt cgttaagttc tttaaagttc tgaaccgcaa acctatctg     2280 aacttcgaca aggcagtatt caaaatcaac atcgtgccga agttaacta cactatctac    2340 gatggtttca acctgcgtaa caccaacctg gctgctaatt ttaacggcca gaacacggaa    2400
atcaacaaca tgaacttcac aaaactgaaa aacttcactg gtctgttcga gttttacaag    2460
ctgctgtgcg tcgacggcat cattacctcc aaaactaaat ctctgataga aggtagaaac    2520
aaagcgctga acctgcagtg tggcctgttt ggtgctatcg ccggatttat agagggcggt    2580
tggacaggga tgattgacgg gtggtacgga tatcaccatc agaatgaaca gggttctggt    2640
tatgccgcgg atcaaaagtc cacgcagaac gcgatcaacg gcatcaccaa taaagtcaat    2700
tcggtaatcg aaaaaatgaa cattcaattt accgctgtgg gcaaagaatt taataaactg    2760
gagaagcgta tggaaaatct gaacaaaaag gtagatgacg gcttcctgga catttggact    2820
tataatgccg aattactggt ccttctcgag aatgaacgta ccctggactt ccatgattcg    2880
aacgtcaaga acttatatga aaaagttaaa agtcaactga aaaataacgc aaaggagatt    2940
ggtaacggat gttttgaatt ctatcacaaa tgcgataacg aatgcatgga atcagttcgc    3000
aatggcactt acgattaccc gaaatattcc gaggaaagca aattgaaccg cgaaaaagtt    3060
gatggggtga aattggagtc aatgggtatc taccagatcc tcgcaattta ttctacggtg    3120
gcatctagcc tggtgcttct ggttagtcta ggcgcgataa gtttctggat gtgtagcaat    3180
ggtagcttac agtgccggat ttgtattggt ctagaaggtg gcggtgggtc cggtggcggt    3240
ggctcagctg aaacggtctc atttagttgg aataagtttg tacctaaaca gccgaacatg    3300
atcttgcaag gcgacgccat cgtgaccagc tcgggcaaat tacagctcaa taaagtggac    3360
gaaaatggca ctccaaaacc gagctctctc gggcgcgccc tttacagtac tccgattcat    3420
atatgggata aagagactgg ttcggtggca tccttcgcag cgtctttcaa ttttacccttt   3480 tatgcaccgg atacgaaacg gctggccgac ggtctggcgt ttttcctggc cccaatcgat    3540
actaagcctc aaacccatgc gggctatctg ggtctgttta cgaaaacga agtgggat       3600 caggttgtag cggtggagtt tgataccttc cgtaattcat gggaccccgcc caacccgcat    3660 attggcatta atgtaaactc tatccgctct attaagacga cctcctggga tttagctaac    3720
aataaagtgg ccaaagtcct gatcacctat gatgcttcca catcacttct ggtcgcatcg    3780
ttggtgtacc cgagccagcg tacaagcaac atactgtcgg acgttgtcga tctgaaaacg    3840
tctttaccag aatgggttag aattggattt tcagcagcga ccggtctgga catccccgga    3900
gaaagtcacg atgttctgtc ctggagcttc gcgagcaatc tacctcacgc tagcagtaac    3960
attgatccgt tagatcttac atcattcgtt ttgcatgagg ccatttaatg aaagctt       4017
```

<210> SEQ ID NO 29
<211> LENGTH: 1337
<212> TYPE: PRT
<213> ORGANISM: Artificial sequence

```
<220> FEATURE:
<223> OTHER INFORMATION: Protein sequence of ORF from pMAL-LC/A-HA-
      GSspacer-SBA

<400> SEQUENCE: 29

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Asn Leu Gly Ile
    370                 375                 380

Glu Gly Arg Ile Ser Glu Phe Gly Ser Met Glu Phe Val Asn Lys Gln
```

```
385                 390                 395                 400
Phe Asn Tyr Lys Asp Pro Val Asn Gly Val Asp Ile Ala Tyr Ile Lys
                405                 410                 415
Ile Pro Asn Ala Gly Gln Met Gln Pro Val Lys Ala Phe Lys Ile His
            420                 425                 430
Asn Lys Ile Trp Val Ile Pro Glu Arg Asp Thr Phe Thr Asn Pro Glu
            435                 440                 445
Glu Gly Asp Leu Asn Pro Pro Glu Ala Lys Gln Val Pro Val Ser
        450                 455                 460
Tyr Tyr Asp Ser Thr Tyr Leu Ser Thr Asp Asn Glu Lys Asp Asn Tyr
465                 470                 475                 480
Leu Lys Gly Val Thr Lys Leu Phe Glu Arg Ile Tyr Ser Thr Asp Leu
                485                 490                 495
Gly Arg Met Leu Leu Thr Ser Ile Val Arg Gly Ile Pro Phe Trp Gly
            500                 505                 510
Gly Ser Thr Ile Asp Thr Glu Leu Lys Val Ile Asp Thr Asn Cys Ile
            515                 520                 525
Asn Val Ile Gln Pro Asp Gly Ser Tyr Arg Ser Glu Glu Leu Asn Leu
530                 535                 540
Val Ile Ile Gly Pro Ser Ala Asp Ile Ile Gln Phe Glu Cys Lys Ser
545                 550                 555                 560
Phe Gly His Glu Val Leu Asn Leu Thr Arg Asn Gly Tyr Gly Ser Thr
                565                 570                 575
Gln Tyr Ile Arg Phe Ser Pro Asp Phe Thr Phe Gly Phe Glu Glu Ser
            580                 585                 590
Leu Glu Val Asp Thr Asn Pro Leu Leu Gly Ala Gly Lys Phe Ala Thr
            595                 600                 605
Asp Pro Ala Val Thr Leu Ala His Glu Leu Ile His Ala Gly His Arg
    610                 615                 620
Leu Tyr Gly Ile Ala Ile Asn Pro Asn Arg Val Phe Lys Val Asn Thr
625                 630                 635                 640
Asn Ala Tyr Tyr Glu Met Ser Gly Leu Glu Val Ser Phe Glu Glu Leu
                645                 650                 655
Arg Thr Phe Gly Gly His Asp Ala Lys Phe Ile Asp Ser Leu Gln Glu
            660                 665                 670
Asn Glu Phe Arg Leu Tyr Tyr Tyr Asn Lys Phe Lys Asp Ile Ala Ser
            675                 680                 685
Thr Leu Asn Lys Ala Lys Ser Ile Val Gly Thr Thr Ala Ser Leu Gln
    690                 695                 700
Tyr Met Lys Asn Val Phe Lys Glu Lys Tyr Leu Leu Ser Glu Asp Thr
705                 710                 715                 720
Ser Gly Lys Phe Ser Val Asp Lys Leu Lys Phe Asp Lys Leu Tyr Lys
                725                 730                 735
Met Leu Thr Glu Ile Tyr Thr Glu Asp Asn Phe Val Lys Phe Phe Lys
            740                 745                 750
Val Leu Asn Arg Lys Thr Tyr Leu Asn Phe Asp Lys Ala Val Phe Lys
            755                 760                 765
Ile Asn Ile Val Pro Lys Val Asn Tyr Thr Ile Tyr Asp Gly Phe Asn
    770                 775                 780
Leu Arg Asn Thr Asn Leu Ala Ala Asn Phe Asn Gly Gln Asn Thr Glu
785                 790                 795                 800
Ile Asn Asn Met Asn Phe Thr Lys Leu Lys Asn Phe Thr Gly Leu Phe
                805                 810                 815
```

-continued

```
Glu Phe Tyr Lys Leu Leu Cys Val Asp Gly Ile Ile Thr Ser Lys Thr
            820                 825                 830
Lys Ser Leu Ile Glu Gly Arg Asn Lys Ala Leu Asn Leu Gln Cys Gly
        835                 840                 845
Leu Phe Gly Ala Ile Ala Gly Phe Ile Glu Gly Gly Trp Thr Gly Met
    850                 855                 860
Ile Asp Gly Trp Tyr Gly Tyr His His Gln Asn Glu Gln Gly Ser Gly
865                 870                 875                 880
Tyr Ala Ala Asp Gln Lys Ser Thr Gln Asn Ala Ile Asn Gly Ile Thr
                885                 890                 895
Asn Lys Val Asn Ser Val Ile Glu Lys Met Asn Ile Gln Phe Thr Ala
            900                 905                 910
Val Gly Lys Glu Phe Asn Lys Leu Glu Lys Arg Met Glu Asn Leu Asn
        915                 920                 925
Lys Lys Val Asp Asp Gly Phe Leu Asp Ile Trp Thr Tyr Asn Ala Glu
    930                 935                 940
Leu Leu Val Leu Leu Glu Asn Glu Arg Thr Leu Asp Phe His Asp Ser
945                 950                 955                 960
Asn Val Lys Asn Leu Tyr Glu Lys Val Lys Ser Gln Leu Lys Asn Asn
                965                 970                 975
Ala Lys Glu Ile Gly Asn Gly Cys Phe Glu Phe Tyr His Lys Cys Asp
            980                 985                 990
Asn Glu Cys Met Glu Ser Val Arg  Asn Gly Thr Tyr Asp  Tyr Pro Lys
        995                 1000                 1005
Tyr Ser  Glu Glu Ser Lys Leu  Asn Arg Glu Lys Val  Asp Gly Val
    1010                1015                 1020
Lys Leu  Glu Ser Met Gly Ile  Tyr Gln Ile Leu Ala  Ile Tyr Ser
    1025                1030                 1035
Thr Val  Ala Ser Ser Leu Val  Leu Leu Val Ser Leu  Gly Ala Ile
    1040                1045                 1050
Ser Phe  Trp Met Cys Ser Asn  Gly Ser Leu Gln Cys  Arg Ile Cys
    1055                1060                 1065
Ile Gly  Leu Glu Gly Gly Gly  Gly Ser Gly Gly Gly  Gly Ser Ala
    1070                1075                 1080
Glu Thr  Val Ser Phe Ser Trp  Asn Lys Phe Val Pro  Lys Gln Pro
    1085                1090                 1095
Asn Met  Ile Leu Gln Gly Asp  Ala Ile Val Thr Ser  Ser Gly Lys
    1100                1105                 1110
Leu Gln  Leu Asn Lys Val Asp  Glu Asn Gly Thr Pro  Lys Pro Ser
    1115                1120                 1125
Ser Leu  Gly Arg Ala Leu Tyr  Ser Thr Pro Ile His  Ile Trp Asp
    1130                1135                 1140
Lys Glu  Thr Gly Ser Val Ala  Ser Phe Ala Ala Ser  Phe Asn Phe
    1145                1150                 1155
Thr Phe  Tyr Ala Pro Asp Thr  Lys Arg Leu Ala Asp  Gly Leu Ala
    1160                1165                 1170
Phe Phe  Leu Ala Pro Ile Asp  Thr Lys Pro Gln Thr  His Ala Gly
    1175                1180                 1185
Tyr Leu  Gly Leu Phe Asn Glu  Asn Glu Ser Gly Asp  Gln Val Val
    1190                1195                 1200
Ala Val  Glu Phe Asp Thr Phe  Arg Asn Ser Trp Asp  Pro Pro Asn
    1205                1210                 1215
```

| | | | | | | | | | | |
|---|---|---|---|---|---|---|---|---|---|---|
| Pro | His | Ile | Gly | Ile | Asn | Val | Asn | Ser | Ile | Arg | Ser | Ile | Lys | Thr |
| | 1220 | | | | 1225 | | | | 1230 | |
| Thr | Ser | Trp | Asp | Leu | Ala | Asn | Asn | Lys | Val | Ala | Lys | Val | Leu | Ile |
| 1235 | | | | | 1240 | | | | | 1245 | |
| Thr | Tyr | Asp | Ala | Ser | Thr | Ser | Leu | Leu | Val | Ala | Ser | Leu | Val | Tyr |
| 1250 | | | | | 1255 | | | | | 1260 | |
| Pro | Ser | Gln | Arg | Thr | Ser | Asn | Ile | Leu | Ser | Asp | Val | Val | Asp | Leu |
| 1265 | | | | | 1270 | | | | | 1275 | |
| Lys | Thr | Ser | Leu | Pro | Glu | Trp | Val | Arg | Ile | Gly | Phe | Ser | Ala | Ala |
| 1280 | | | | | 1285 | | | | | 1290 | |
| Thr | Gly | Leu | Asp | Ile | Pro | Gly | Glu | Ser | His | Asp | Val | Leu | Ser | Trp |
| 1295 | | | | | 1300 | | | | | 1305 | |
| Ser | Phe | Ala | Ser | Asn | Leu | Pro | His | Ala | Ser | Ser | Asn | Ile | Asp | Pro |
| 1310 | | | | | 1315 | | | | | 1320 | |
| Leu | Asp | Leu | Thr | Ser | Phe | Val | Leu | His | Glu | Ala | Ile | Lys | Leu |
| 1325 | | | | | 1330 | | | | | 1335 | |

<210> SEQ ID NO 30
<211> LENGTH: 2634
<212> TYPE: DNA
<213> ORGANISM: artificial sequence
<220> FEATURE:
<223> OTHER INFORMATION: Synthesised DNA sequence of LHn/B with Enterokinase activation site

<400> SEQUENCE: 30

```
ggatccatgc cggttaccat caacaacttc aactacaacg acccgatcga caacaacaac      60
atcattatga tggaaccgcc gttcgcacgt ggtaccggac gttactacaa ggcttttaag     120
atcaccgacc gtatctggat catcccggaa cgttacacct cggttacaa acctgaggac      180
ttcaacaaga gtagcgggat tttcaatcgt gacgtctgcg agtactatga tccagattat     240
ctgaatacca acgataagaa gaacatattc cttcagacta tgattaaact cttcaaccgt     300
atcaaaagca aaccgctcgg tgaaaaactc ctcgaaatga ttatcaacgg tatcccgtac     360
ctcggtgacc gtcgtgtccc gcttgaagag ttcaacacca catcgcaag cgtcaccgtc       420
aacaaactca tcagcaaccc aggtgaagtc gaacgtaaaa aaggtatctt cgcaaacctc     480
atcatcttcg gtccgggtcc ggtcctcaac gaaaacgaaa ccatcgacat cggtatccag     540
aaccacttcg caagccgtga aggtttcggt ggtatcatgc agatgaaatt ctgcccggaa     600
tacgtcagtg tcttcaacaa cgtccaggaa aacaaaggtg caagcatctt caaccgtcgt     660
ggttacttca gcgacccggc actcatcctc atgcatgaac tcatccacgt cctccacggt     720
ctctacggta tcaaagttga cgacctcccg atcgtcccga cgagaagaa attcttcatg      780
cagagcaccg acgcaatcca ggctgaggaa ctctacacct tcggtggcca agacccaagt     840
atcataaccc cgtccaccga caaaagcatc tacgacaaag tcctccagaa cttcagggt      900
atcgtggaca gactcaacaa agtcctcgtc tgcatcagcg acccgaacat caatatcaac     960
atatacaaga caagttcaa agacaagtac aaattcgtcg aggacagcga aggcaaatac    1020
agcatcgacg tagaaagttt cgacaagctc tacaaaagcc tcatgttcgg tttcaccgaa    1080
accaacatcg ccgagaacta caagatcaag caagggcaa gttacttcag cgacagcctc    1140
ccgcctgtca aaatcaagaa cctcttagac aacgagattt acacaattga gagggcttc    1200
aacatcagtg acaagacat ggagaaggaa tacagaggtc agaacaaggc tatcaacaaa    1260
caggcatacg aggagatcag caaagaacac ctcgcagtct acaagatcca gatgtgcgtc    1320
```

```
gacgaagaaa agctgtacga cgacgacgac aaagaccgtt ggggttcttc gctgcagtgc   1380
atcgacgttg acaacgaaga cctgttcttc atcgctgaca aaaacagctt cagtgacgac   1440
ctgagcaaaa acgaacgtat cgaatacaac acccagagca actacatcga aaacgacttc   1500
ccgatcaacg aactgatcct ggacaccgac ctgataagta aaatcgaact gccgagcgaa   1560
aacaccgaaa gtctgaccga cttcaacgtt gacgttccgg tttacgaaaa acagccggct   1620
atcaagaaaa tcttcaccga cgaaaacacc atcttccagt acctgtacag ccagaccttc   1680
ccgctggaca tccgtgacat cagtctgacc agcagtttcg acgacgctct gctgttcagc   1740
aacaaagttt acagtttctt cagcatggac tacatcaaaa ccgctaacaa agttgttgaa   1800
gcagggctgt cgctggttg ggttaaacag atcgttaacg acttcgttat cgaagctaac   1860
aaaagcaaca ctatggacaa aatcgctgac atcagtctga tcgttccgta catcggtctg   1920
gctctgaacg ttggtaacga aaccgctaaa ggtaactttg aaaacgcttt cgagatcgct   1980
ggtgcaagca tcctgctgga gttcatcccg gaactgctga tcccggttgt tggtgctttc   2040
ctgctggaaa gttacatcga caacaaaaac aagatcatca aaaccatcga caacgctctg   2100
accaaacgta cgaaaaatg gagtgatatg tacggtctga tcgttgctca gtggctgagc   2160
accgtcaaca cccagttcta ccaccatcaaa gaaggtatgt acaaagctct gaactaccag   2220
gctcaggctc tggaagagat catcaaatac cgttacaaca tctacagtga aaggaaaag   2280 agtaacatca acatcgactt caacgacatc aacagcaaac tgaacgaagg tatcaaccag   2340
gctatcgaca catcaacaa cttcatcaac ggttgcagtg ttagctacct gatgaagaag   2400
atgatcccgc tggctgttga aaaactgctg gacttcgaca cacccctgaa aaagaacctg   2460
ctgaactaca tcgacgaaaa caagctgtac ctgatcggta gtgctgaata cgaaaaaagt   2520
aaagtgaaca aataccggaa gaccatcatg ccgttcgacc tgagtatcta caccaacgac   2580
accatcctga tcgaaatgtt caacaaatac aactctctag actgatagaa gctt         2634
```

<210> SEQ ID NO 31  
<211> LENGTH: 4563  
<212> TYPE: DNA  
<213> ORGANISM: Artificial sequence  
<220> FEATURE:  
<223> OTHER INFORMATION: DNA sequence of ORF from pMAL-LHn/B-GSspacer-ECL

<400> SEQUENCE: 31

```
atgaaaatcg aagaaggtaa actggtaatc tggattaacg gcgataaagg ctataacggt    60
ctcgctgaag tcggtaagaa attcgagaaa gataccggaa ttaaagtcac cgttgagcat   120
ccggataaac tggaagagaa attcccacag gttgcggcaa ctggcgatgg ccctgacatt   180
atcttctggg cacacgaccg ctttggtggc tacgctcaat ctggcctgtt ggctgaaatc   240
accccggaca aagcgttcca ggacaagctg tatccgttta cctgggatgc cgtacgttac   300
aacggcaagc tgattgctta cccgatcgct gttgaagcgt tatcgctgat ttataacaaa   360
gatctgctgc cgaacccgcc aaaaacctgg gaagagatcc cggcgctgga taagaactg    420 aaagcgaaag gtaagagcgc gctgatgttc aacctgcaag aaccgtactt cacctggccg   480
ctgattgctg ctgacggggg ttatgcgttc aagtatgaaa acggcaagta cgacattaaa   540
gacgtgggcg tggataacgc tggcgcgaaa gcgggtctga cctcctggt tgacctgatt   600 aaaaacaaac acatgaatgc agacaccgat tactccatcg cagaagctgc ctttaataaa   660
ggcgaaacag cgatgaccat caacggcccg tgggcatggt ccaacatcga caccagcaaa   720
```

-continued

```
gtgaattatg gtgtaacggt actgccgacc ttcaagggtc aaccatccaa accgttcgtt      780
ggcgtgctga gcgcaggtat taacgccgcc agtccgaaca aagagctggc aaaagagttc      840
ctcgaaaact atctgctgac tgatgaaggt ctggaagcgg ttaataaaga caaaccgctg      900
ggtgccgtag cgctgaagtc ttacgaggaa gagttggcga agatccacg tattgccgcc       960
actatggaaa acgcccagaa aggtgaaatc atgccgaaca tcccgcagat gtccgctttc     1020
tggtatgccg tgcgtactgc ggtgatcaac gccgccagcg tcgtcagac tgtcgatgaa      1080
gccctgaaag acgcgcagac taattcgagc tcgaacaaca caacaataa caataacaac      1140
aacctcggga tcgagggaag gatttcagaa ttcggatcca tgccggttac catcaacaac     1200
ttcaactaca acgacccgat cgacaacaac aacatcatta tgatggaacc gccgttcgca     1260
cgtggtaccg gacgttacta caaggctttt aagatcaccg accgtatctg gatcatcccg     1320
gaacgttaca ccttcggtta caaacctgag gacttcaaca agagtagcgg gattttcaat     1380
cgtgacgtct gcgagtacta tgatccagat tatctgaata ccaacgataa gaagaacata     1440
ttccttcaga ctatgattaa actcttcaac cgtatcaaaa gcaaaccgct cggtgaaaaa     1500
ctcctcgaaa tgattatcaa cggtatcccg tacctcggtg accgtcgtgt cccgcttgaa     1560
gagttcaaca ccaacatcgc aagcgtcacc gtcaacaaac tcatcagcaa cccaggtgaa     1620
gtcgaacgta aaaaaggtat cttcgcaaac ctcatcatct tcggtccggg tccggtcctc     1680
aacgaaaacg aaaccatcga catcggtatc cagaaccact tcgcaagccg tgaaggtttc     1740
ggtggtatca tgcagatgaa attctgcccg gaatacgtca gtgtcttcaa caacgtccag     1800
gaaaacaaag gtgcaagcat cttcaaccgt cgtggttact tcagcgaccc ggcactcatc     1860
ctcatgcatg aactcatcca cgtcctccac ggtctctacg gtatcaaagt tgacgacctc     1920
ccgatcgtcc cgaacgagaa gaaattcttc atgcagagca ccgacgcaat ccaggctgag     1980
gaactctaca ccttcggtgg ccaagaccca agtatcataa ccccgtccac cgacaaaagc     2040
atctacgaca aagtcctcca gaacttcagg ggtatcgtgg acagactcaa caaagtcctc     2100
gtctgcatca gcgaccccgaa catcaatatc aacatataca agaacaagtt caaagacaag     2160
tacaaattcg tcgaggacag cgaaggcaaa tacagcatcg acgtagaaag tttcgacaag     2220
ctctacaaaa gcctcatgtt cggtttcacc gaaaccaaca tcgccgagaa ctacaagatc     2280
aagacaaggg caagttactt cagcgacagc ctcccgcctg tcaaaatcaa gaacctctta     2340
gacaacgaga tttacacaat tgaagagggc ttcaacatca gtgacaaaga catggagaag     2400
gaatacagag gtcagaacaa ggctatcaac aaacaggcat acgaggagat cagcaaagaa     2460
cacctcgcag tctacaagat ccagatgtgc gtcgacgaag aaaagctgta cgacgacgac     2520
gacaaagacc gttgggggttc ttcgctgcag tgcatcgacg ttgacaacga agacctgttc     2580
ttcatcgctg acaaaaacag cttcagtgac gacctgagca aaaacgaacg tatcgaatac     2640
aacacccaga gcaactacat cgaaaacgac ttcccgatca cgaactgat cctggacacc      2700
gacctgataa gtaaaatcga actgccgagc gaaaacaccg aaagtctgac cgacttcaac     2760
gttgacgttc cggtttacga aaaacagccg gctatcaaga aatcttcac cgacgaaaac      2820
accatcttcc agtacctgta cagccagacc ttcccgctgg acatccgtga catcagtctg     2880
accagcagtt tcgacgacgc tctgctgttc agcaacaaag tttacagttt cttcagcatg     2940
gactacatca aaccgctaa caaagttgtt gaagcagggc tgttcgctgg ttgggttaaa      3000
cagatcgtta acgacttcgt tatcgaagct aacaaaagca cactatgga caaaatcgct      3060
gacatcagtc tgatcgttcc gtacatcggt ctggctctga acgttggtaa cgaaaccgct     3120
```

```
aaaggtaact tgaaaacgc tttcgagatc gctggtgcaa gcatcctgct ggagttcatc    3180
ccggaactgc tgatcccggt tgttggtgct ttcctgctgg aaagttacat cgacaacaaa    3240
aacaagatca tcaaaaccat cgacaacgct ctgaccaaac gtaacgaaaa atggagtgat    3300
atgtacggtc tgatcgttgc tcagtggctg agcaccgtca acacccagtt ctacaccatc    3360
aaagaaggta tgtacaaagc tctgaactac caggctcagg ctctggaaga gatcatcaaa    3420
taccgttaca acatctacag tgagaaggaa aagagtaaca tcaacatcga cttcaacgac    3480
atcaacagca aactgaacga aggtatcaac caggctatcg acaacatcaa caacttcatc    3540
aacggttgca gtgttagcta cctgatgaag aagatgatcc cgctggctgt tgaaaaactg    3600
ctggacttcg acaacaccct gaaaaagaac ctgctgaact acatcgacga aaacaagctg    3660
tacctgatcg gtagtgctga atacgaaaaa agtaaagtga acaaatacct gaagaccatc    3720
atgccgttcg acctgagtat ctacaccaac gacaccatcc tgatcgaaat gttcaacaaa    3780
tacaactctc tagaaggtgg cggtgggtcc ggtggcggtg gctcagtgga aaccatatcg    3840
tttagcttca gtgagtttga accgggtaac aacgatttga ccttgcaagg tgcagccatt    3900
attacacaat ctggggtttt acaactcacc aagattaatc aaaatggcat gccggcttgg    3960
gactcaacgg gccgaactct atatactaaa cctgtgcaca tttgggatat gaccacaggc    4020
actgtggcca gctttgaaac tagattctcc ttttccattg aacaacccta tacacgccca    4080
ctccccgctg atggtttagt attctttatg ggaccaacaa gtccaagcc agctcaaggt    4140 tatggatacc tcggagtatt caacaactca aacaggata actcatacca aacacttgct    4200
gttgagtttg acactttcag taacccatgg gaccctcccc aggttccaca cattggaatc    4260
gatgtcaact ccattcgatc catcaaaacc caaccttttc aattggacaa tggccaagtt    4320
gccaatgttg tcataaaata tgatgcttcc tccaaaatct tacttgccgt gttggtttac    4380
ccttccagtg gagccattta caccatcgct gaaattgtgg atgtgaagca agttcttcct    4440
gagtgggtcg acgttggtct ctcgggtgca accggtgcac agcgagacgc cgctgagaca    4500
cacgacgttt attcttggtc attccatgcc tcgttgccag aaacaaacga ttaatgaaag    4560
ctt                                                                    4563
```

<210> SEQ ID NO 32
<211> LENGTH: 1519
<212> TYPE: PRT
<213> ORGANISM: Artificial sequence
<220> FEATURE:
<223> OTHER INFORMATION: Protein sequence of ORF from pMAL-LHn/B-GSspacer-ECL

<400> SEQUENCE: 32

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95
```

```
Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
            130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
            210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
            290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
            325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Asn Leu Gly Ile
            370                 375                 380

Glu Gly Arg Ile Ser Glu Phe Gly Ser Met Pro Val Thr Ile Asn Asn
385                 390                 395                 400

Phe Asn Tyr Asn Asp Pro Ile Asp Asn Asn Ile Ile Met Met Glu
            405                 410                 415

Pro Pro Phe Ala Arg Gly Thr Gly Arg Tyr Tyr Lys Ala Phe Lys Ile
            420                 425                 430

Thr Asp Arg Ile Trp Ile Ile Pro Glu Arg Tyr Thr Phe Gly Tyr Lys
            435                 440                 445

Pro Glu Asp Phe Asn Lys Ser Ser Gly Ile Phe Asn Arg Asp Val Cys
            450                 455                 460

Glu Tyr Tyr Asp Pro Asp Tyr Leu Asn Thr Asn Asp Lys Lys Asn Ile
465                 470                 475                 480

Phe Leu Gln Thr Met Ile Lys Leu Phe Asn Arg Ile Lys Ser Lys Pro
            485                 490                 495

Leu Gly Glu Lys Leu Leu Glu Met Ile Ile Asn Gly Ile Pro Tyr Leu
            500                 505                 510
```

```
Gly Asp Arg Arg Val Pro Leu Glu Glu Phe Asn Thr Asn Ile Ala Ser
        515                 520                 525

Val Thr Val Asn Lys Leu Ile Ser Asn Pro Gly Glu Val Glu Arg Lys
    530                 535                 540

Lys Gly Ile Phe Ala Asn Leu Ile Ile Phe Gly Pro Gly Pro Val Leu
545                 550                 555                 560

Asn Glu Asn Glu Thr Ile Asp Ile Gly Ile Gln Asn His Phe Ala Ser
                565                 570                 575

Arg Glu Gly Phe Gly Gly Ile Met Gln Met Lys Phe Cys Pro Glu Tyr
            580                 585                 590

Val Ser Val Phe Asn Asn Val Gln Glu Asn Lys Gly Ala Ser Ile Phe
        595                 600                 605

Asn Arg Arg Gly Tyr Phe Ser Asp Pro Ala Leu Ile Leu Met His Glu
    610                 615                 620

Leu Ile His Val Leu His Gly Leu Tyr Gly Ile Lys Val Asp Asp Leu
625                 630                 635                 640

Pro Ile Val Pro Asn Glu Lys Lys Phe Phe Met Gln Ser Thr Asp Ala
                645                 650                 655

Ile Gln Ala Glu Glu Leu Tyr Thr Phe Gly Gly Gln Asp Pro Ser Ile
            660                 665                 670

Ile Thr Pro Ser Thr Asp Lys Ser Ile Tyr Asp Lys Val Leu Gln Asn
        675                 680                 685

Phe Arg Gly Ile Val Asp Arg Leu Asn Lys Val Leu Val Cys Ile Ser
    690                 695                 700

Asp Pro Asn Ile Asn Ile Asn Ile Tyr Lys Asn Lys Phe Lys Asp Lys
705                 710                 715                 720

Tyr Lys Phe Val Glu Asp Ser Glu Gly Lys Tyr Ser Ile Asp Val Glu
                725                 730                 735

Ser Phe Asp Lys Leu Tyr Lys Ser Leu Met Phe Gly Phe Thr Glu Thr
            740                 745                 750

Asn Ile Ala Glu Asn Tyr Lys Ile Lys Thr Arg Ala Ser Tyr Phe Ser
        755                 760                 765

Asp Ser Leu Pro Pro Val Lys Ile Lys Asn Leu Leu Asp Asn Glu Ile
    770                 775                 780

Tyr Thr Ile Glu Glu Gly Phe Asn Ile Ser Asp Lys Asp Met Glu Lys
785                 790                 795                 800

Glu Tyr Arg Gly Gln Asn Lys Ala Ile Asn Lys Gln Ala Tyr Glu Glu
                805                 810                 815

Ile Ser Lys Glu His Leu Ala Val Tyr Lys Ile Gln Met Cys Val Asp
            820                 825                 830

Glu Glu Lys Leu Tyr Asp Asp Asp Lys Asp Arg Trp Gly Ser Ser
        835                 840                 845

Leu Gln Cys Ile Asp Val Asp Asn Glu Asp Leu Phe Phe Ile Ala Asp
    850                 855                 860

Lys Asn Ser Phe Ser Asp Asp Leu Ser Lys Asn Glu Arg Ile Glu Tyr
865                 870                 875                 880

Asn Thr Gln Ser Asn Tyr Ile Glu Asn Asp Phe Pro Ile Asn Glu Leu
                885                 890                 895

Ile Leu Asp Thr Asp Leu Ile Ser Lys Ile Glu Leu Pro Ser Glu Asn
            900                 905                 910

Thr Glu Ser Leu Thr Asp Phe Asn Val Asp Val Pro Val Tyr Glu Lys
        915                 920                 925

Gln Pro Ala Ile Lys Lys Ile Phe Thr Asp Glu Asn Thr Ile Phe Gln
```

```
                930             935             940
Tyr Leu Tyr Ser Gln Thr Phe Pro Leu Asp Ile Arg Asp Ile Ser Leu
945                 950                 955                 960

Thr Ser Ser Phe Asp Asp Ala Leu Leu Phe Ser Asn Lys Val Tyr Ser
                965                 970                 975

Phe Phe Ser Met Asp Tyr Ile Lys Thr Ala Asn Lys Val Val Glu Ala
            980                 985                 990

Gly Leu Phe Ala Gly Trp Val Lys Gln Ile Val Asn Asp Phe Val Ile
            995                 1000                1005

Glu Ala Asn Lys Ser Asn Thr Met Asp Lys Ile Ala Asp Ile Ser
    1010                1015                1020

Leu Ile Val Pro Tyr Ile Gly Leu Ala Leu Asn Val Gly Asn Glu
    1025                1030                1035

Thr Ala Lys Gly Asn Phe Glu Asn Ala Phe Glu Ile Ala Gly Ala
    1040                1045                1050

Ser Ile Leu Leu Glu Phe Ile Pro Glu Leu Leu Ile Pro Val Val
    1055                1060                1065

Gly Ala Phe Leu Leu Glu Ser Tyr Ile Asp Asn Lys Asn Lys Ile
    1070                1075                1080

Ile Lys Thr Ile Asp Asn Ala Leu Thr Lys Arg Asn Glu Lys Trp
    1085                1090                1095

Ser Asp Met Tyr Gly Leu Ile Val Ala Gln Trp Leu Ser Thr Val
    1100                1105                1110

Asn Thr Gln Phe Tyr Thr Ile Lys Glu Gly Met Tyr Lys Ala Leu
    1115                1120                1125

Asn Tyr Gln Ala Gln Ala Leu Glu Glu Ile Ile Lys Tyr Arg Tyr
    1130                1135                1140

Asn Ile Tyr Ser Glu Lys Glu Lys Ser Asn Ile Asn Ile Asp Phe
    1145                1150                1155

Asn Asp Ile Asn Ser Lys Leu Asn Glu Gly Ile Asn Gln Ala Ile
    1160                1165                1170

Asp Asn Ile Asn Asn Phe Ile Asn Gly Cys Ser Val Ser Tyr Leu
    1175                1180                1185

Met Lys Lys Met Ile Pro Leu Ala Val Glu Lys Leu Leu Asp Phe
    1190                1195                1200

Asp Asn Thr Leu Lys Lys Asn Leu Leu Asn Tyr Ile Asp Glu Asn
    1205                1210                1215

Lys Leu Tyr Leu Ile Gly Ser Ala Glu Tyr Glu Lys Ser Lys Val
    1220                1225                1230

Asn Lys Tyr Leu Lys Thr Ile Met Pro Phe Asp Leu Ser Ile Tyr
    1235                1240                1245

Thr Asn Asp Thr Ile Leu Ile Glu Met Phe Asn Lys Tyr Asn Ser
    1250                1255                1260

Leu Glu Gly Gly Gly Gly Ser Gly Gly Gly Gly Ser Val Glu Thr
    1265                1270                1275

Ile Ser Phe Ser Phe Ser Glu Phe Glu Pro Gly Asn Asn Asp Leu
    1280                1285                1290

Thr Leu Gln Gly Ala Ala Ile Ile Thr Gln Ser Gly Val Leu Gln
    1295                1300                1305

Leu Thr Lys Ile Asn Gln Asn Gly Met Pro Ala Trp Asp Ser Thr
    1310                1315                1320

Gly Arg Thr Leu Tyr Thr Lys Pro Val His Ile Trp Asp Met Thr
    1325                1330                1335
```

-continued

```
Thr Gly Thr Val Ala Ser Phe Glu Thr Arg Phe Ser Phe Ser Ile
    1340            1345            1350

Glu Gln Pro Tyr Thr Arg Pro Leu Pro Ala Asp Gly Leu Val Phe
    1355            1360            1365

Phe Met Gly Pro Thr Lys Ser Lys Pro Ala Gln Gly Tyr Gly Tyr
    1370            1375            1380

Leu Gly Val Phe Asn Asn Ser Lys Gln Asp Asn Ser Tyr Gln Thr
    1385            1390            1395

Leu Ala Val Glu Phe Asp Thr Phe Ser Asn Pro Trp Asp Pro Pro
    1400            1405            1410

Gln Val Pro His Ile Gly Ile Asp Val Asn Ser Ile Arg Ser Ile
    1415            1420            1425

Lys Thr Gln Pro Phe Gln Leu Asp Asn Gly Gln Val Ala Asn Val
    1430            1435            1440

Val Ile Lys Tyr Asp Ala Ser Ser Lys Ile Leu Leu Ala Val Leu
    1445            1450            1455

Val Tyr Pro Ser Ser Gly Ala Ile Tyr Thr Ile Ala Glu Ile Val
    1460            1465            1470

Asp Val Lys Gln Val Leu Pro Glu Trp Val Asp Val Gly Leu Ser
    1475            1480            1485

Gly Ala Thr Gly Ala Gln Arg Asp Ala Ala Glu Thr His Asp Val
    1490            1495            1500

Tyr Ser Trp Ser Phe His Ala Ser Leu Pro Glu Thr Asn Asp Lys
    1505            1510            1515

Leu
```

CONJUGATES OF GALACTOSE-BINDING LECTINS AND CLOSTRIDIAL NEUROTOXINS AS ANALGESICS

This application is a continuation in part of U.S. application Ser. No. 09/529,130, filed on Jun. 22, 2000, now U.S. Pat. No. 7,052,702, which is a 371 of PCT/GB98/03001, filed Oct. 7, 1998, which claims the foreign priority of United Kingdom 9721189.0, filed Oct. 8, 1997.

TECHNICAL FIELD

This invention relates to a class of novel agents that are able to modify nociceptive afferent function. The agents may inhibit the release of neurotransmitters from discrete populations of neurones and thereby reduce or preferably prevent the transmission of afferent pain signals from peripheral to central pain fibers. The agent may be used in or as a pharmaceutical for the treatment of pain, particularly chronic pain.

BACKGROUND

The sensation of pain due to injury or disease is carried from the periphery to the brain by a multi-neuronal pathway. The first part of this system comprises the primary nociceptive afferents that form synapses with secondary neurones in the dorsal horn of the spinal cord, or the nuclei of the cranial nerves. These synapses pass on the incoming information by the release of neurotransmitters and neuromodulators such as glutamate and substance P. These synapses are, therefore, possible sites for intervention to alleviate pain, indeed one of the modes of action of the opiate analgesics is to down-modulate neurotransmitter release at these synapses.

Unfortunately, the opiates have a number of limitations as drugs. Firstly, there are a number of chronic pain conditions for which the opiates are not effective. Secondly, the opiates have a number of side effects that are mediated both peripherally (constipation) and centrally (respiratory depression and euphoria) which present problems for long term use.

There is, therefore, a need for the development of new pharmaceuticals for the treatment of pain, particularly chronic pain.

One approach to this problem is the use of new agents containing fragments of clostridial neurotoxins (WO96/33273).

The clostridial neurotoxins are proteins with molecular masses of the order of 150 kDa. They are produced by various species of bacterium of the genus *Clostridium*, most importantly *C. tetani* and several strains of *C. botulinum*. There are at present eight different classes of the neurotoxins known: tetanus toxin, and botulinum neurotoxin in its serotypes A, B, $C_1$, D, E, F and G, and they all share similar structures and modes of action. The clostridial neurotoxins are synthesised by the host bacterium as single polypeptides that are modified post-translationally to form two polypeptide chains joined together by a disulphide bond. The two chains are termed the heavy chain (H), which has a molecular mass of approximately 100 kDa, and the light chain (L), which has a molecular mass of approximately 50 kDa. Two distinct functions can be identified within the H-chain; binding and translocation. The carboxy-terminal half ($H_C$) is involved in the high affinity, neurospecific binding of the toxin to cell surface acceptors, whilst the amino-terminal half ($H_N$) is central to the translocation of the toxin into the neuronal cell. For botulinum neurotoxin type A these domains are considered to reside within amino acid residues 872-1296 for the $H_C$, amino acid residues 449-871 for the $H_N$ and residues 1-448 for the LC. The minimal domains necessary for the activity of the light chain of clostridial toxins are described in J. Biol. Chem. Vol. 267, No. 21, July 1992, pages 14721-14729. The eight distinct neurotoxin light chains (L) are highly specific zinc-dependent endopeptidases which each hydrolyse different but specific peptide bonds in one of three substrate proteins, synaptobrevin, syntaxin or SNAP-25. These substrates are important components of the neurosecretory machinery. The hydrolytic activity of the clostridial toxins results in a prolonged muscular paralysis. The functions of all three identified domains are necessary for the toxic activity of the clostridial endopeptidases.

Some of the clostridial endopeptidases, most notably botulinum neurotoxin type A, have been used as pharmaceutical agents for the treatment of a range of muscle dystonias. The flaccid paralyzing action of the native botulinum toxins makes them appropriate for this use.

The use of fragments of clostridial neurotoxins for the desired purpose of analgesia is dependent on the invention of conjugates, or derivatives of these molecules, with a specific binding activity that will deliver the L-chain endopeptidase to the nociceptive afferent neurons in preference to other neurones in the relevant anatomical locus. Delivery of these conjugates includes binding to the cell surface, internalization via an endosomal compartment and translocation of the clostridial endopeptidase activity into the cytosol.

Targeting of extracellular species to specific intracellular locations following endocytosis involves an appreciation of a number of possible targeting strategies. It is understood that early endosomes are part of the key sorting mechanisms of the cell, routing species to late endosome (and onto lysosomes for degradation), recycling to the cell surface or to the Trans-Golgi Network. Intracellular routing determinants have been suggested that determine the pathway and final destination of particular species (Mellman, 1996, Annu. Rev. Cell Biol., 12, 575-625).

Current data suggests that translocation of native clostridial neurotoxins occurs from an acidic intracellular compartment, though the exact location and nature of the compartment is unknown (Montecucco & Schiavo, 1994, Mol. Micro. 13, 1-8). In patent WO96/33273 it is proposed that for an agent to be effective, the agent must target to an appropriate compartment for translocation of the toxin. As an example of specific intracellular targeting, internalization of the NGF-receptor is by specific endocytosis and retrograde routing (initiated by receptor-ligand complex), via acidic endosomes to the cell body, and an agent incorporating NGF is given in support of WO96/33273.

STATEMENT OF INVENTION

The present invention relates to an agent that can reduce and preferably prevent the transmission of pain signals from the periphery to the central nervous system, thereby alleviating the sensation of pain. Specifically, the invention can provide an agent that can reduce and preferably prevent the transmission of pain signals from nociceptive afferents to projection neurones. More specifically, the invention can provide an agent that can inhibit the exocytosis of at least one neurotransmitter or neuromodulator substance from at least one category of nociceptive afferents.

In one aspect of the invention, an agent is provided which can be administered to the spinal cord, and which can inhibit the release of at least one neurotransmitter or neuromodulator from the synaptic terminals of nociceptive afferents terminating in that region of the spinal cord.

In a second aspect of the invention, there is provided an agent which can specifically target defined populations of afferent neurones, so that the effect of the agent is limited to that cell type.

In a third aspect of the invention, there is provided a method of treatment of pain that comprises administering an effective dose of the agent according to the invention.

In a fourth aspect of the invention, the agent can be expressed recombinantly as a fusion protein that includes the required components of the agent.

Definitions

Without wishing to be limited by the definitions set down, it is intended in this description that the following terms have the following meanings:

Light chain means the smaller of the two polypeptide components of any of the clostridial neurotoxins. It is commonly referred to as the L-chain or simply L. An L-chain has a molecular mass of approximately 50 kDa, and it is a metalloprotease exhibiting high substrate specificity for vesicle and/or plasma membrane associated proteins involved in the exocytotic process.

Heavy chain means the larger of the two polypeptide components of any of the clostridial neurotoxins. It is commonly referred to as H-chain or simply H and has a molecular mass of approximately 100 kDa.

$H_C$ fragment means a peptide derived from the H-chain of a clostridial neurotoxin which is responsible for binding of the native holotoxin to cell surface acceptor(s) involved in the intoxicating action of clostridial toxin prior to internalization of the toxin into the cell. It may be approximately equivalent to the carboxy-terminal half of the H-chain, or the domain corresponding to that fragment in the intact H-chain.

$H_N$ fragment means a fragment derived from the H-chain of a clostridial neurotoxin approximately equivalent to the amino-terminal half of the H-chain, or the domain corresponding to that fragment in the intact H-chain. It is characterized as:

A portion of the H-chain which enables translocation of that portion of the neurotoxin molecule such that a functional expression of light chain activity occurs within a target cell.

The domain responsible for translocation of the endopeptidase activity, following binding of neurotoxin to its specific cell surface receptor via the binding domain, into the target cell.

The domain responsible for formation of ion-permeable pores in lipid membranes under conditions of low pH.

The domain responsible for increasing the solubility of the entire polypeptide compared to the solubility of light chain alone.

$LH_N$ means a fragment derived from a clostridial neurotoxin that contains the L-chain, or a functional fragment thereof, coupled to a $H_N$ fragment.

BoNT/A means botulinum neurotoxin serotype A, and is a neurotoxin produced by *Clostridium botulinum*; it has a molecular mass of approximately 150 kDa.

$LH_N$/A is $LH_N$ that is derived from *Clostridium botulinum* neurotoxin type A.

Targeting Moiety (TM) means any chemical structure of an agent which functionally interacts with a binding site causing a physical association between the agent and the surface of a primary sensory afferent.

Primary sensory afferent is a nerve cell that can carry sensory information from the periphery towards the central nervous system.

Primary nociceptive afferent is a nerve cell that can carry sensory information from the periphery towards the central nervous system, where that information can result in a sensation of pain.

Lectin is any protein that binds to oligosaccharide structures.

Galactose-binding lectin is a lectin that binds to oligosaccharide structures in which the terminal residue is derived from galactose or N-acetylgalactosamine.

DETAILED DESCRIPTION OF THE INVENTION

It can be seen from this disclosure that an agent for reducing or preventing the transmission of pain signals from peripheral, nociceptive afferent neurones to projection neurones has many potential applications in the reduction of the sensation of pain, particularly of severe chronic pain.

Lectins are a class of proteins, often glycoproteins, that bind to carbohydrate structures. Lectins are found across the whole range of life forms from viruses to mammals. The most commonly exploited sources are the abundant lectins found in the seeds of plants. Lectins have previously been labeled and used as cell surface markers.

According to the invention, there is provided an agent that can inhibit the release of at least one neurotransmitter or neuromodulator or both from the synaptic terminals of nociceptive afferents.

It is known that such an agent can be produced based on the use of fragments of clostridial neurotoxin conjugated to a targeting ligand (WO96/33273). Given the known complexity of intracellular transport and the constraints on construct requirements, it is surprising that conjugates between toxin fragments and a specific sub-class of lectins that bind only to galactosyl residues form agents to produce analgesics that are particularly potent and selective. Inventions incorporating such lectins are the subject of this disclosure and several examples are provided.

One example of a class of plant-derived, galactose-binding lectins are those that can be purified from the seeds of the genus *Erythrina*. These lectins have been characterized to exist predominantly as non-covalent dimeric proteins with total molecular weights of approximately 60 kDa. Lectins have been isolated from several *Erythrina* species including: *E. corallodendron* (Gilboa-Garber and Mizrahi, 1981, Can. J. Biochem. 59, 315-320), *E. cristagalli* (Iglesias et al., 1982, Eur. J. Biochem. 123, 247-252), *E. indica* (Horejsi et al., 1980, Biochim. Biophys. Acta 623, 439-448), *E. arborescens, E. suberosa, E. lithosperma* (Bhattacharyya et al., 1981, Archiv. Biochem. Biophys. 211, 459-470) *E. caffra, E. flabelliformis, E. latissima, E. lysistemon, E. humeana, E. perrieri, E. stricta*, and *E. zeyheri* (Lis et al., 1985, Phytochem. 24, 2803-2809).

These lectins have been analyzed for their selectivity for saccharide binding (see e.g. Kaladas et al., 1982, Archiv. Biochem. Biophys. 217, 624-637). They have been found to bind preferentially to oligosaccharides with a terminal β-D-galactosyl residue.

A second example of a plant-derived, galactose-binding lectin with the desired binding specificity can be obtained from *Glycine max* (soy) beans. This lectin (soya bean agglutinin, SBA) is a tetrameric protein with a total molecular weight of approximately 110 kDa. It binds to oligosaccharides containing galactose or N-acetylgalactosamine residues.

An example of a galactose-binding lectin from bacteria is PA-I, obtained from *Pseudomonas aeruginosa*. PA-I is a D-galactosephilic lectin with a molecular weight of about 13 kDa and it binds to galactose-containing oligosaccharides (Gilboa-Garber and Mizrahi, 1981, Can. J. Biochem. 59, 315-320).

These and other lectins of the sub-class of galactose-binding lectins can be used as targeting moieties (TM) for conjugates of the type described in WO96/33273. The requirements for TMs in these agents are that they show specificity for the primary sensory afferents over other spinal nerves and that they lead to the internalization of the agents into an appropriate intracellular compartment. The lectins of this invention fulfil these criteria. Surprisingly, in comparison to other lectins of WO96/33273, they can fulfil these criteria more efficiently and can provide agents with enhanced selectivity for nociceptive afferent neurosecretion.

Thus, in one embodiment of the invention a galactose-binding lectin is conjugated, using linkages that may include one or more spacer regions, to a derivative of the clostridial neurotoxins.

In another embodiment of the invention the agent is expressed in a recombinant form as a fusion protein. The fusion protein may be derived from nucleic acid encoding an appropriate fragment of a galactose-binding lectin, in addition to any desired spacer domains, with nucleic acid encoding all or part of a polypeptide of one serotype of neurotoxin. Such a nucleic acid may be a chimera derived from the nucleic acid encoding polypeptides from more than one serotype.

In this embodiment, a genetic construct is employed which encodes the non-cytotoxic protease (or fragment thereof), the translocating domain, and the TM.

The coding sequences of the TM, translocating domain and protease/protease fragment are preferably arranged in a single genetic construct. These coding sequences are preferably arranged in-frame so that subsequent transcription/translation is continuous through both coding sequences and results in a fusion protein.

Alternatively, the coding sequences of the TM, translocation domain and protease/protease fragment may be arranged on separate genetic constructs and, following translation, the corresponding proteins associate with each other to form the agent. Association of the TM, translocation domain and protease/protease fragment translation products may be encouraged by ensuring that each translation product has one or more mutually compatible amino acids at an exposed surface. An example of such an amino acid is cysteine, or other sulphur-containing amino acids. The presence of a sulphur group on these amino acids allows the formation of disulphide bridges between the TM, translocation domain and protease/protease translation products.

The fusion protein aspect of the present invention may employ any variation of any TM—translocation domain—protease sequence identified in the present specification. For example:

N and C-terminal protein fusions (ie. either 5' or 3' genetic construct fusions) may be employed. Different combinations of TM-protease-translocation domain, protease-translocation domain-TM and protease-TM-translocation domain may be more suitable than others;

should a protease-TM-translocation domain fusion be employed then it may be preferable to insert a specific cleavage sequence between the protease/protease fragment and the TM, to enable the TM to have freedom to bind to the target receptor. According to this embodiment it may be preferable to engineer into the genetic construct means (eg. a disulphide bridge) to keep the fusion complex together;

The genetic construct preferably incorporates a nucleic acid sequence encoding a spacer peptide at the fusion junction between the TM and the protease/translocation domain. However, a spacer is not essential. Examples of spacer peptides include:

PPPIEGR [Kim, J. S., Raines, R. T. (1993). Ribonuclease S-peptide as a carrier in fusion proteins. Protein Sci 2(3):348-56];

collagen-like spacer [Rock, F., Everett, M., Klein, M. (1992). Over-expression and structure-function analysis of a bioengineered IL-2/IL-6 chimeric lymphokine. Protein Eng 5(6):583-91]; and trypsin sensitive diphtheria toxin peptide [O'Hare, M., Brown, A. N., Hussain, K., Gebhardt, A., Watson, G., Roberts, L. M., Vitetta, E. S., Thorpe, P. E., Lord, J. M. (1990). Cytotoxicity of a recombinant ricin-A-chain fusion protein containing a proteolytically-cleavable spacer sequence. FEBS Lett Oct 29;273(1-2):200-4].

Turning to the protease (pr protease fragment) component of the agent, all protease variants described in the present application and in the present Applicant's co-pending application U.S. Ser. No. 09/255,829 may be employed. The content of U.S. Ser. No. 09/255,829 is herein incorporated by reference thereto.

All constructs have a 5' ATG codon to encode an N-terminal methionine and a C-terminal translational stop codon if these codons are not already present. Expression of a number of fusion proteins is well-known in the art and was so at the priority date of the present application (ie. 8 Oct. 1997). Methods for the construction and expression of the constructs of the present invention may employ information from the following references and others:

Lorberboum-Galski, H., FitzGerald, D., Chaudhary, V., Adhya, S., Pastan, I. (1988). Cytotoxic activity of an interleukin 2-*Pseudomonas* exotoxin chimeric protein produced in *Escherichia coli*. Proc Natl Acad Sci USA 85(6): 1922-6;

Murphy, J. R. (1988) Diphtheria-related peptide hormone gene fusions: a molecular genetic approach to chimeric toxin development. Cancer Treat Res; 37:123-40;

Williams, D. P., Parker, K., Bacha, P., Bishai, W., Borowski, M., Genbauffe, F., Strom, T. B., Murphy, J. R. (1987). Diphtheria toxin receptor binding domain substitution with interleukin-2: genetic construction and properties of a diphtheria toxin-related interleukin-2 fusion protein. Protein Eng; 1(6):493-8;

Arora, N., Williamson, L. C., Leppla, S. H., Halpern, J. L. (1994). Cytotoxic effects of a chimeric protein consisting of tetanus toxin light chain and anthrax toxin lethal factor in non-neuronal cells J Biol Chem; 269(42):26165-71;

Brinkmann, U., Reiter, Y., Jung, S. H., Lee, B., Pastan, I. (1993). A recombinant immunotoxin containing a disulphide-stabilized Fv fragment. Proc Natl Acad Sci USA; 90(16):7538-42; and O'Hare, M., Brown, A. N., Hussain, K., Gebhardt, A., Watson, G., Roberts, L. M., Vitetta, E. S., Thorpe, P. E., Lord, J. M. (1990). Cytotoxicity of a recombinant ricin-A-chain fusion protein containing a proteolytically-cleavable spacer sequence. FEBS Lett October 29;273(1-2):200-4.

The method of preparing a fusion protein according to the present invention requires nucleic acid sequence data relating to the selected TM and the protease/protease fragment. These sequence data were readily available at the priority date of the present application as evidenced by the data/publications of several preferred TMs which have been listed in the present specification. Alternatively, any necessary sequence data may be obtained by techniques well-known to the skilled person.

In one embodiment, DNA encoding the TM sequences may be cloned from a source organism by screening a cDNA library for the correct coding region (for example by using specific oligonucleotides based on the known sequence information to probe the library), isolating the TM DNA, sequencing this DNA for confirmation purposes, and then placing the isolated DNA in an appropriate expression vector for expression in the chosen host.

As an alternative to isolation of the sequence from a library, the available sequence information may be employed to prepare specific primers for use in PCR, whereby the coding sequence is then amplified directly from the source material and, by suitable use of primers, may be cloned directly into an expression vector.

Another alternative method for isolation of the coding sequence is to use the existing sequence information and synthesise a copy, possibly incorporating alterations, using DNA synthesis technology.

Another alternative method is to use existing protein sequence information and synthesise a version of the coding sequence that can give rise to that protein sequence. Using DNA synthesis technology to do this (and the alternative described above) enables the codon bias of the coding sequence to be modified to be optimal for the chosen expression host. This may give rise to superior expression levels of the fusion protein.

All of the above methods may be employed to obtain sequence information on the selected protease component of the agent.

Ideally, optimization of the codon bias for the expression host would be applied to the TM, the spacer (if there is one), the translocation domain and the protease. Optimization of the codon bias is possible by application of the protein sequence into freely available DNA/protein database software, eg. programs available from Genetics Computer Group, Inc.

By way of example, the following TM protein sequences were readily available by the priority date of the present application (ie. 8 Oct. 1997):

```
Pseudomonas aeruginosa PA-I lectin (ACCESSION
X65933) (SEQ ID 33)
MAWKGEVLANNEAGQVTSIIYNPGDVITIVAAGWASYGPTQKWGPQGDRE
HPDQGLICHDAFCGALVMKIGNSGTIPVNTGLFRWVAPNNVQGAITLIYN
DVPGTYGNNSGSFSVNIGKDQS Soybean agglutinin (SBA) [ACCESSION P05046]
(modified to remove the signal sequence)
(SEQ ID 34)
aetvsfswnkfvpkqpnmilqgdaivtssgklqlnkvdengtpksslgra
lystpihiwdketgsvasfaasfnftfyapdtkrladglafflapidtkp
qthagylglfnenesgdqvvavefdtfrnswdppnphiginvnsirsitt
swdlannkvakvlitydastsllvaslvypsqrtsnilsdvvdlktslpe
wvrigfsaatgldipgshdvlswsfasnlphassnidpldltsfvlheai Erythrina corallodendron lectin (ECorL)
[ACCESSION CAA36986] (modified to remove the
signal sequence) (SEQ ID 35)
vetisfsfsefepgndnltlqgaalitqsgvlqlkinqngmpawdstgrt
lyakpvhiwdmttgtvasfetrfsfsieqpytrplpadglvffmgptksk
paqgygylgifnnskqdnsyqtlgvefdtfsnqwdppqvphigidvnsir
siktqpfqldngqvanvvikydasskilhavlvypssgaiytiaeivdvk
qvlpewvdvglsgatgaqrdaaethdvyswsfqaslpetnd
```

In another embodiment of the invention the required $LH_N$, which may be a hybrid of an L and $H_N$ from different clostridial toxin serotypes, is expressed as a recombinant fusion protein with the galactose-binding lectin, and may also include one or more spacer regions.

In a further embodiment of the invention the required TM, L or $LH_N$ and translocation domain components may be separately expressed in a recombinant form and subsequently linked, covalently or non-covalently, to provide the desired agent.

In a further embodiment of the invention the required translocation domain may be of a non-clostridial origin, comprising instead a peptide or other entity capable of similar or enhanced function. Examples would include, but not be restricted to, the translocation domain of diphtheria toxin (O'Keefe et al., Proc. Natl. Acad. Sci. USA (1992) 89, 6202-6206; Silverman et al., J. Biol. Chem. (1993) 269, 22524-22532), the translocation domain of *Pseudomonas* exotoxin type A (Prior et al., Biochemistry (1992) 31, 3555-3559), the translocation domains of anthrax toxin (Blanke et al., Proc. Natl. Acad. Sci. USA (1996) 93, 8437-8442) and a variety of fusogenic or hydrophobic peptides of translocating function (Plank et al., J. Biol. Chem (1994) 269, 12918-12924).

The translocating domain may be obtained from a microbial protein source, in particular from a bacterial or viral protein source. It is well documented that certain domains of bacterial toxin molecules are capable of forming such pores. It is also known that certain translocation domains of virally expressed membrane fusion proteins are capable of forming such pores. Such domains may be employed in the present invention.

Hence, in one embodiment, the translocating domain is a translocating domain of an enzyme, such as a bacterial or viral toxin. One such molecule is the heavy chain of a clostridial neurotoxin, for example botulinum neurotoxin type A. Other sources of bacterial toxin translocating domains include diphtheria toxin and domain II of pseudomonas exotoxin.

Other sources of translocating domains include certain translocating domains of virally expressed membrane fusion proteins. For example, Wagner et al. (1992) and Murata et al. (1992) describe the translocation (ie. membrane fusion and vesiculation) function of a number of fusogenic and amphiphilic peptides derived from the N-terminal region of influenza virus haemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translocating domain of Foamy virus envelope glycoprotein. Virally encoded "spike proteins" have particular application in the context of the present invention, for example, the E1 protein of SFV and the G protein of the G protein of VSV.

Preferably it has been found to use only those portions of the protein molecule capable of pore-formation within the endosomal membrane.

Methodology to enable assessment of membrane fusion and thus identification of translocation domains suitable for use in the present invention are provided by Methods in Enzymology Vol 220 and 221, Membrane Fusion Techniques, Parts A and B, Academic Press 1993.

Examples of preferred translocating domains for use in the present invention are listed in the table below. The below-listed citations are all herein incorporated by reference.

| Translocation domain source | Amino acid residues | References |
|---|---|---|
| Diphtheria toxin | 194-380 | Silverman et al., 1994, J. Biol. Chem. 269, 22524-22532<br>London E., 1992, Biochem. Biophys. Acta., 1113, 25-51 |
| Domain II of *pseudomonas* exotoxin | 405-613 | Prior et al., 1992, Biochemistry 31, 3555-3559<br>Kihara & Pastan, 1994, Bioconj Chem. 5, 532-538 |
| Influenza virus haemagglutinin | GLFGAIAGFIENGWEGMIDGWYG, and variants thereof | Plank et al., 1994, J. Biol. Chem. 269, 12918-12924<br>Wagner et al., 1992, PNAS, 89, 7934-7938<br>Murata et al., 1992, Biochemistry 31, 1986-1992 |
| Semliki Forest virus fusogenic protein | Translocation domain | Kielian et al., 1996, J Cell Biol. 134(4), 863-872 |
| Vesicular Stomatitis virus glycoprotein G | 118-139 | Yao et al., 2003, Virology 310(2), 319-332 |
| SER virus F protein | Translocation domain | Seth et al., 2003, J Virol 77(11) 6520-6527 |
| Foamy virus envelope glyoprotein | Translocation domain | Picard-Maureau et al., 2003, J Virol. 77(8), 4722-4730 |

Use of the translocating domains listed in the above table includes use of sequence variants thereof. A variant may comprise one or more conservative nucleic acid substitutions and/or nucleic acid deletions or insertions, with the proviso that the variant possesses the requisite translocating function. A variant may also comprise one or more amino acid substitutions and/or amino acid deletions or insertions, so long as the variant possesses the requisite translocating function.

The only functional requirement of the translocating domain is that it is capable of forming appropriate pores in the endosomal membrane. A number of routine methods are available for confirming that a particular translocating domain has the requisite translocating activity, and thus to determine the presence of a translocating domain. Shone et al. (1987), and Blaustein et al. (1987) provide details of two very simple assays to confirm that any particular bacterial translocating domain has the requisite translocating activity. Shone (1987) describes a simple in vitro assay employing liposomes, which are challenged with a test molecule. The presence of a molecule having the requisite translocating function is confirmed by release from the liposomes of $K^+$ and/or labeled NAD. Blaustein (1987) describes a simple in vitro assay employing planar phospholipid bilayer membranes, which are challenged with a test molecule. The presence of a molecule having the requisite translocation function is confirmed by an increase in conductance across the phospholipid membrane.

Exploitation in Industry

The agent described in this invention can be used in vivo, either directly or as a pharmaceutically acceptable salt, for treatment of pain.

For example, an agent according to the invention can be administered by spinal injection (epidural or intrathecal) at the level of the spinal segment involved in the innervation of an affected organ for the treatment of pain. This is, for example, applicable in the treatment of deep tissue pain, such as chronic malignant pain.

BRIEF DESCRIPTION OF THE DRAWINGS

The present invention will now be described by reference to the following examples together with the Figures that show the following:

FIGS. 8A and 8B. Activity of WGA-$LH_N$/A on release of neurotransmitter from eDRG and eSC neurons.

FIGS. 9A-9D. Activity of ExL-$LH_N$/A in an in vivo electrophysiology model of analgesia.

FIG. 11: Expression, purification and activation of an $LH_N$/C-ECL fusion protein.

FIG. 12: Expression, purification and activation of an $LH_N$/A-ECL fusion protein.

FIG. 13: Purification and activation of an $LH_N$/B-ECL fusion protein.

EXAMPLE 1

Figure 1:
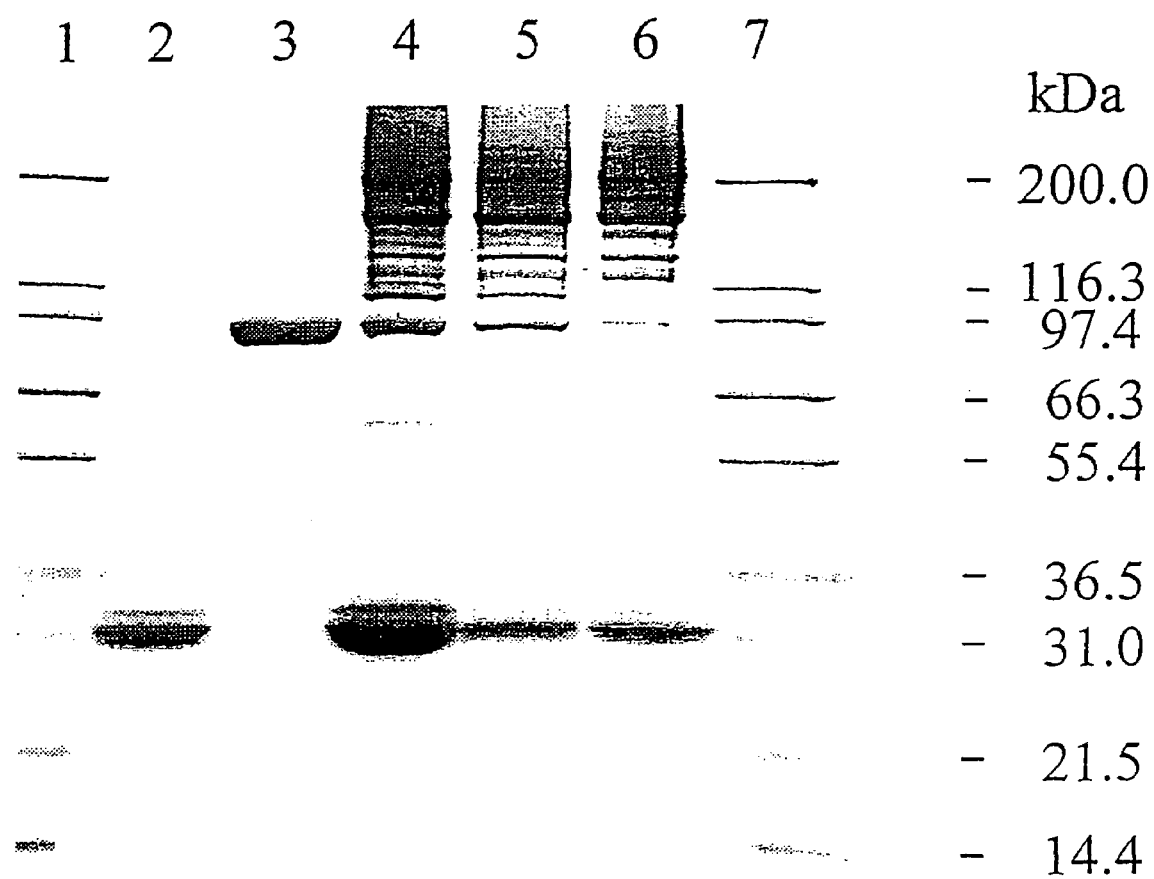
FIG. 1. SDS-PAGE analysis of fractions from ExL-$LH_N$/A purification scheme.

The Production of a Conjugate Between a Lectin from *Erythrina cristagalli* and $LH_N$/A Materials Lectin from *E. cristagalli* (ExL) was obtained from Sigma Ltd.

$LH_N$/A was prepared essentially by the method of Shone C. C., Hambleton, P., and Melling, J. 1987, *Eur. J. Biochem.* 167, 175-180.

SPDP was from Pierce Chemical Co.

PD-10 desalting columns were from Pharmacia.

Dimethylsulphoxide (DMSO) was kept anhydrous by storage over a molecular sieve.

Denaturing sodium dodecylsulphate polyacrylamide gel electrophoresis (SDS-PAGE) was performed using gels and reagents from Novex Immobilized lactose-agarose was obtained from Sigma Ltd.

Additional reagents were obtained from Sigma Ltd.

Methods

The lyophilized lectin was rehydrated in phosphate buffered saline (PBS) to a final concentration of 10 mg/ml. Aliquots of this solution were stored at −20° C. until use.

The ExL was reacted with an equal concentration of SPDP by the addition of a 10 mM stock solution of SPDP in DMSO with mixing. After one hour at room temperature the reaction was terminated by desalting into PBS over a PD-10 column.

The thiopyridone leaving group was removed from the product by reduction with dithiothreitol (DTT, 5 mM, 30 min). The product of this reaction was analyzed spectrophotometrically at 280 nm and 343 nm to determine the degree of derivatisation achieved. The degree of derivatisation achieved was 0.8±0.06 mol/mol. The thiopyridone and DTT were removed by once again desalting into PBS over a PD-10 column.

The $LH_N/A$ was desalted into PBSE (PBS containing 1 mM EDTA). The resulting solution (0.5-1.0 mg/ml) was reacted with a four- or five-fold molar excess of SPDP by addition of a 10 mM stock solution of SPDP in DMSO. After 3 h at room temperature the reaction was terminated by desalting over a PD-10 column into PBS.

A portion of the derivatised $LH_N/A$ was removed from the solution and reduced with DTT (5 mM, 30 min). This sample was analyzed spectrophotometrically at 280 mm and 343 nm to determine the degree of derivatisation. The degree of derivatisation achieved was 2.26±0.10 mol/mol.

The bulk of the derivatised $LH_N/A$ and the derivatised ExL were mixed in proportions such that the ExL was in greater than three-fold molar excess. The conjugation reaction was allowed to proceed for >16 h at 4° C.

The product mixture was centrifuged to clear any precipitate that had developed. The supernatant was concentrated by centrifugation through concentrators (with 10000-50000 molecular weight exclusion limit) prior to a two step purification strategy. As the first step, the concentrated material was applied to a Superose 12 column on an FPLC chromatography system (Pharmacia). The column was eluted with PBS and the elution profile followed at 280 nm.

Fractions were analyzed by SDS-PAGE on 4-20% polyacrylamide gradient gels, followed by staining with Coomassie Blue. The major band of conjugate has an apparent molecular mass of between 130-160 kDa; this is separated from the bulk of the remaining unconjugated $LH_N/A$ and more completely from the unconjugated ExL. Fractions containing conjugate were pooled prior to the second chromatography step; immobilized lactose-agarose. Selected post-Superose-12 fractions were applied to PBS-washed lactose-agarose and incubated for 2 hours at 4° C. to facilitate binding. Lectin-containing proteins (i.e. $ExL-LH_N/A$ conjugate) remained bound to the agarose during subsequent washing with PBS to remove contaminants (predominantly unconjugated $LH_N/A$). $ExL-LH_N/A$ conjugate was eluted from the column by the addition of 0.3M lactose (in PBS) and the elution profile followed at 280 nm. The fractions containing conjugate were pooled, dialyzed against PBS, and stored at 4° C. until use.

In FIG. 1 is illustrated the SDS-PAGE profile during different stages in the conjugate purification scheme. Lanes 2 and 3 indicate ExL lectin and $LH_N/A$ respectively prior to conjugation. Lanes 4, 5 & 6 represent conjugation mixture, post-Superose-12 and post-lactose affinity chromatography samples respectively. Lane 6 is therefore indicative of the profile of the final conjugate material. Molecular weight markers are represented in lanes 1 & 7 with sizes indicated on the figure.

Figure 5:
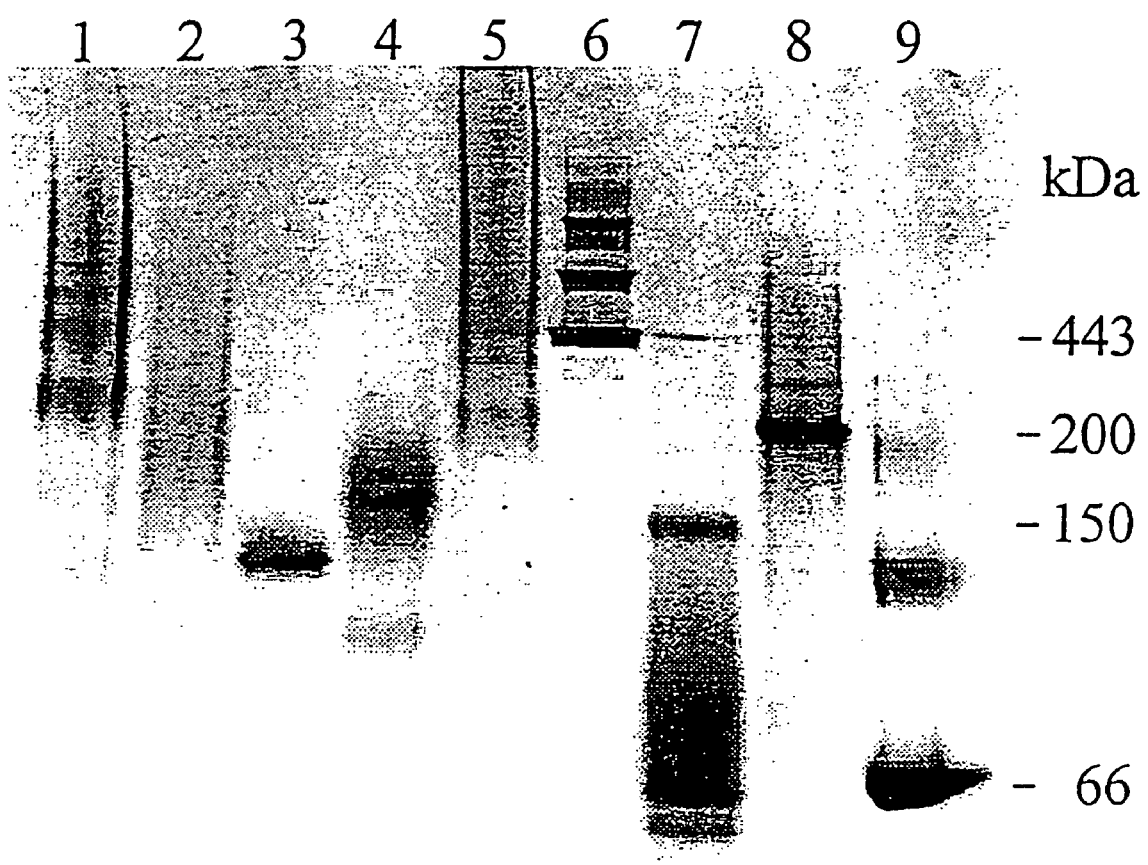
FIG. 5. Native gel analysis of ExL- and SBA-$LH_N$/A.

On the SDS-PAGE gel there are bands due to lectin alone in fractions containing the conjugate, this material is probably due to the non-covalent homo-dimeric nature of the ExL; where only one monomer of ExL is covalently attached to the $LH_N/A$ the other is dissociated from the complex by the SDS in the electrophoretic procedure giving rise to these bands. The absence of free lectin monomers was confirmed by native PAGE analysis and is illustrated in FIG. 5. $ExL-LH_N/A$ (lane 5) was analyzed by non-denaturing PAGE. Samples were separated using 4-20% polyacrylamide gel for 6.75 hours, 125V, 4° C. The electrophoresis profile was compared to those of $LH_N/A$ (lane 3) and ExL lectin only (lane 4). A range of marker proteins were analyzed alongside; apoferritin (lane 6), β-amylase (lane 8), alcohol dehydrogenase (lane 7) and albumin (lane 9). Approximate molecular sizes are indicated.

EXAMPLE 2

The Production of a Conjugate Between a Lectin from *Erythrina corallodendron* and $LH_N/A$ The procedure for production of a conjugate between a lectin from *Erythrina corallodendron* and $LH_N/A$ is essentially as described in Example 1 but with the following differences:

Materials

Lectin from *E. corallodendron* (EcL) was obtained from Sigma Ltd.

Figure 3:
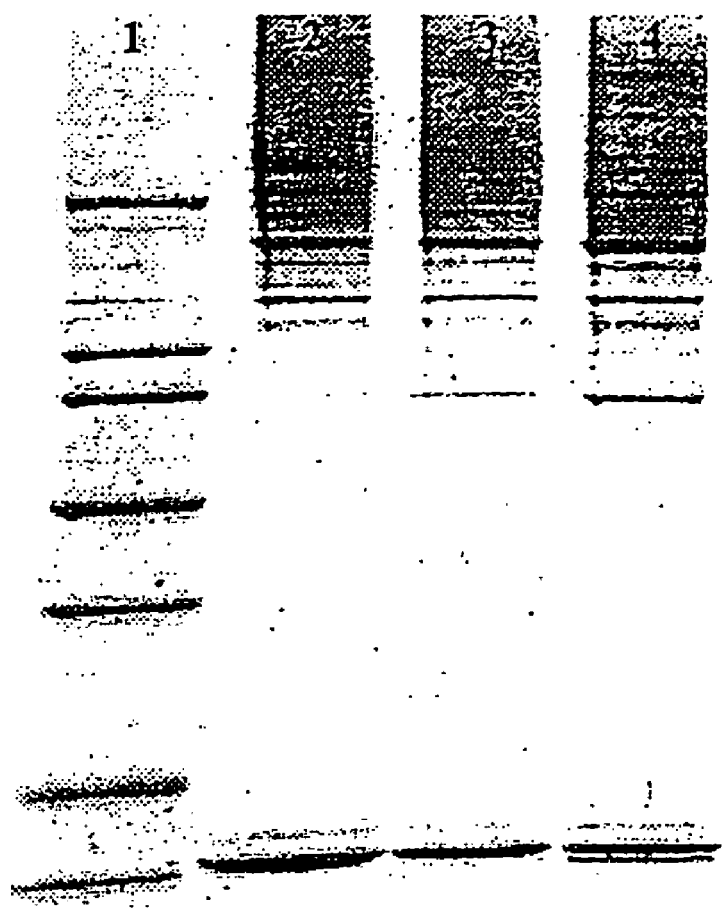
FIG. 3. SDS-PAGE analysis of fractions from EcL-$LH_N$/A purification scheme.

FIG. 3 illustrates the purification scheme for the $EcL-LH_N/A$ conjugate. Samples were applied to 4-20% polyacrylamide gradient gels and subjected to electrophoresis prior to staining with Coomassie blue. Lane 1=molecular weight markers. Lane 2 represents the post-lactose affinity purified sample of $EcL-LH_N/A$. Lane 3 is a sample of pre-lactose affinity purified (size-exclusion chromatography only) $EcL-LH_N/A$. Lane 4 is a sample of pre-lactose affinity purified $ExL-LH_N/A$.

EXAMPLE 3

The Production of a Conjugate between a Lectin from *Glycine max* and $LH_N/A$

The procedure for production of a conjugate between a lectin from *Glycine max* and $LH_N/A$ is essentially as described in Example 1 but with the following differences:

Materials

Lectin from *G. max* (SBA) was obtained from Sigma Ltd.

Method

Figure 4:
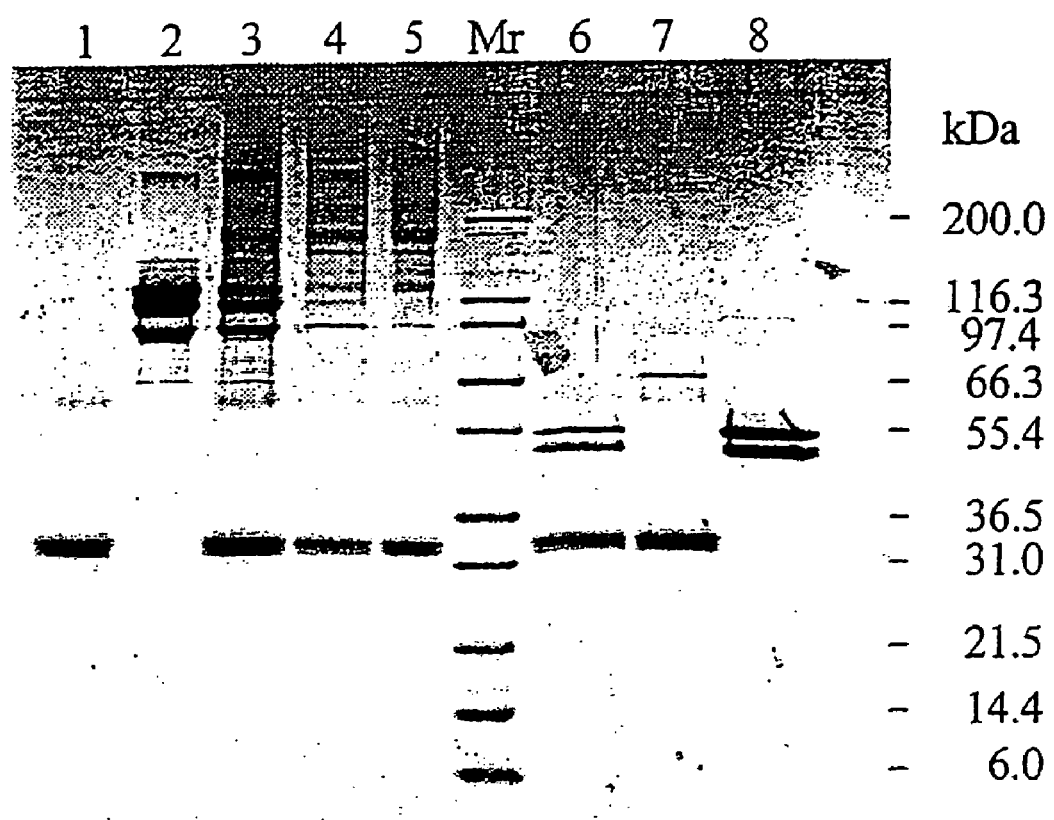
FIG. 4. SDS-PAGE analysis of fractions from SBA-$LH_N$/A purification scheme.

For the affinity chromatography step an immobilized N-acetylgalactosamine (GalNAc) column was used and specific $SBA-LH_N/A$ was eluted by the addition of 0.3M lactose. FIG. 4 illustrates SDS-PAGE profile changes during the purification scheme for $SBA-LH_N/A$. $SBA-LH_N/A$ was purified from crude conjugate mixture by Superose-12 size-exclusion chromatography and immobilized N-acetylgalactosamine affinity chromatography. Samples were subjected to SDS-PAGE on 4-20% polyacrylamide gels. Lanes 6-8 were run in the presence of 0.1M DTT. Lanes 1 (& 7) and 2 (&8) indicate SBA and SPDP-derivatised $LH_N/A$ respectively, prior to conjugation. Lanes 3, 4 & 5 (& 6) represent conjugation mixture, post-Superose-12 and post-affinity chromatography samples respectively. Lane 5 is therefore indicative of the profile of the final conjugate material. Molecular weight markers are represented in lanes Mr with sizes indicated on the figure.

The absence of free lectin monomers was confirmed by native non-denaturing PAGE analysis as illustrated in FIG. 5. Samples were separated using 4-20% polyacrylamide gel for 6.75 hours, 125V, 4° C. The electrophoresis profile of $SBA-LH_N/A$ (lane 1) was compared to those of SBA lectin only (lane 2) and $LH_N/A$ (lane 3). A range of marker proteins were analyzed alongside; apoferritin (lane 6), β-amylase (lane 8), alcohol dehydrogenase (lane 7) and albumin (lane 9). Approximate molecular sizes are indicated.

EXAMPLE 4

Activity of ExL-LH$_N$/A in Primary Neuronal Cultures

The dorsal root ganglia contain the cell bodies of primary nociceptive afferent neurons. It is well established that in primary in vitro cultures of this tissue the neurons retain many of the characteristics of the nociceptive afferent. These characteristics include the ability to release neuropeptides such as substance P in response to chemical stimuli known to cause pain in vivo (e.g. capsaicin). Neurons anatomically adjacent to those of the DRG include those of the spinal cord. Cultures of SC neurons prepared from embryonic rats can be established in vitro and the release of neurotransmitter ($^3$H-glycine) under potassium stimulation can be assessed. As such, the eSC neurons represent a model cell for testing the selectivity of the agents described.

Figure 6:
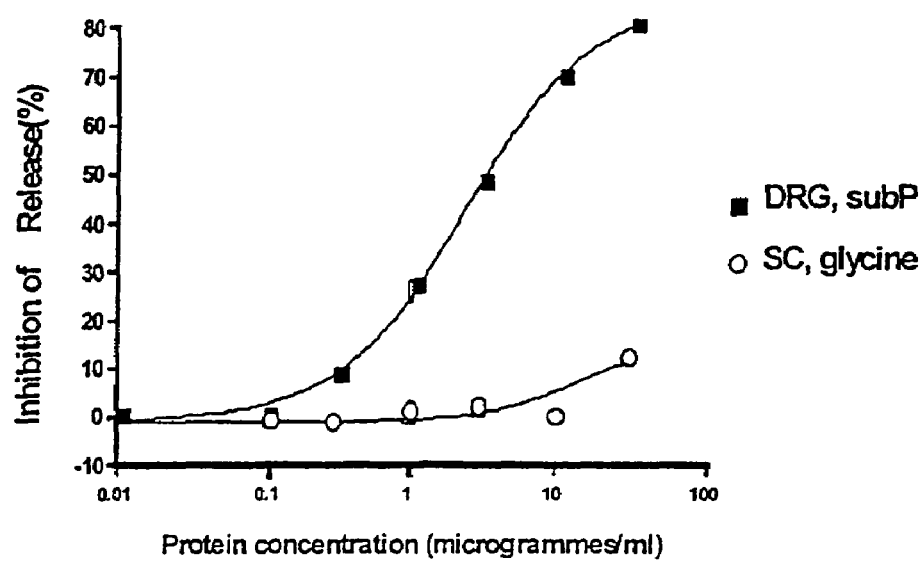
FIG. 6. Activity of ExL-$LH_N$/A on release of neurotransmitter from eDRG and eSC neurons FIG. 7. Activity of SBA-$LH_N$/A on release of neurotransmitter from eDRG and eSC neurons.

The selectivity of the EXL-LH$_N$/A agent for eDRG over eSC neurons is clearly illustrated in FIG. 6. The dose curves document the effectiveness of ExL-LH$_N$/A in an in vitro cell culture model by comparing inhibition of neurotransmission in eDRG with eSC neurons.

Materials

Substance P enzyme linked immunosorbent assay kits were from Cayman Chemical Company.

Western blot reagents were obtained from Novex

Monoclonal antibody SMI-81 was from Sternberger Monoclonals Inc.

Methods

Primary cultures of dorsal root ganglion and embryonic spinal cord neurons were established following dissociation of the ganglia dissected from rat embryos (embryological age 12-15 days). For the preparation of eDRG neurons, the cells were plated into 12 well plates at an initial density of $3 \times 10^5$ cells/well in a medium containing NGF (100 ng/ml). After one day in culture, fresh medium containing cytosine arabinoside ($10 \times 10^{-6}$ M) was added to kill non-neuronal cells. After 2-4 days the cytosine arabinoside was removed. After several more days in culture the medium was replaced with fresh medium containing conjugate or LH$_N$.

For the preparation of eSC neurons, Cells were plated onto poly-D-lysine coated 12 well plates (Costar) at a density of $2 \times 10^6$ cells per well (1 ml/well). 'Plating' medium was MEM with Earles Salts (Sigma), containing 5% foetal bovine serum (FBS), 5% heat inactivated horse serum (HS), 0.6% dextrose, 1.5 g/l NaHCO$_3$ and 2 mM L-glutamine. Cultures are incubated at 37° C. with 10% CO$_2$. The medium was changed to 'feeding' medium (plating medium minus the FBS with N1 (Sigma) 1/50 supplement) after one day. When glial cells became almost confluent anti-mitotic agents (15 microgrammes/ml 5-fluoro-2'-deoxyuridine (FdU) and 35 microgrammes/ml uridine (U)) were added for a further 2-3 days. Cells were cultured for at least 3 weeks prior to use.

The cells were incubated with these agents for varying times and then tested for their ability to release the neurotransmitters glutamate and substance P (eDRG) or glycine (eSC). After the release assays were performed the cells were lysed and the hydrophobic proteins were extracted by phase partitioning with Triton-X-114 following the method outlined in Boyd, Duggan, Shone and Foster (J. Biol. Chem. 270, 18216-18218, 1995).

Substance P Release Assay

The release of endogenous substance P was effected by collecting cell supernatants after treating the cells for 5 min with either a physiological balanced salt solution or a balanced salt solution in which the potassium ion concentration had been raised to 100 mM with consequent reduction in the sodium ion concentration to maintain isotonicity. Total substance P was measured after extraction in 2 M acetic acid, 0.1% trifluoroacetic acid and subsequent dehydration. Substance P immunoreactivity was measured using an enzyme immunoassay kit (Cayman Chemical Company).

[$^3$H] Glutamate Release Assay

The release of glutamate was measured after loading the cells with [$^3$H]glutamine as a radiotracer. The [$^3$H]glutamine is converted to [$^3$H]glutamate in the cell, and it is this [$^3$H] glutamate that is taken up by synaptic vesicles and released upon depolarization of the neuron. The cells are loaded with the [$^3$H]glutamine ($5 \times 10^{-6}$ Ci/ml in HEPES-buffered MEM) for 2 h, then washed twice with HEPES-buffered MEM and thrice with balanced salt solution (BSS). Basal release was assessed with a 3 min incubation with BSS. Stimulated release was determined by a 3 min incubation with BSS in which the potassium concentration had been elevated to 80-100 mM with a consequent reduction in the sodium concentration to maintain isotonicity. All manipulations were performed at 37° C. The cells were lysed by the addition of Triton-X-100 (0.1%, v/v). For the basal and stimulated release superfusates the glutamate was separated from the glutamine by ion-exchange chromatography over Dowex-1 resin. The relevant fractions were analyzed for $^3$H content by liquid scintillation counting.

[$^3$H] Glycine Release Assay

The release of glycine was measured after loading the cells with [$^3$H]glycine as a radiotracer. The [$^3$H]glycine is taken up by synaptic vesicles and released upon depolarization of the neuron. The cells are loaded with the [$^3$H]glycine ($2 \times 10^{-6}$ Ci/ml in HEPES-buffered MEM) for 2 h, then washed once with HEPES-buffered MEM and thrice with balanced salt solution (BSS). Basal release was assessed with a 5 min incubation with BSS. Stimulated release was determined by a 5 min incubation with BSS in which the potassium concentration had been elevated to 56 mM with a consequent reduction in the sodium concentration to maintain isotonicity. All manipulations were performed at 37° C. The cells were lysed by the addition of 2 M acetic acid, 0.1% trifluoroacetic acid. Fractions were analyzed for their $^3$H content by liquid scintillation counting and inhibition of release determined.

FIG. 6 illustrates the activity of ExL-LH$_N$/A on release of neurotransmitter from eDRG and eSC neurons. Both eDRG and eSC cultures were exposed to a range of ExL-LH$_N$/A concentrations (1 ml volumes) for three days. The percentage inhibition of eDRG substance P (n) and eSC [$^3$H]-glycine (?) release is in comparison to untreated controls. The data shown is representative of =3 determinations. IC$_{50}$ for eDRG was determined to be 3.66±0.92 µg/ml. An inhibition of 50% was not obtained for eSC using the concentration range employed.

Western Blotting

ExL-LH$_N$/A was applied to eDRG for 16 hours. After the determination of neurotransmitter release the cells were lysed by the addition of 2 M acetic acid, 0.1% trifluoroacetic acid and subsequently dehydrated. To extract the membrane proteins from these mixtures Triton-X-114 (10%, v/v) was added and incubated at 4° C. for 60 min, the insoluble material was removed by centrifugation and the supernatants were then warmed to 37° C. for 30 min. The resulting two phases were separated by centrifugation and the upper phase discarded. The proteins in the lower phase were precipitated with chloroform/methanol for analysis by Western blotting.

Figure 2:
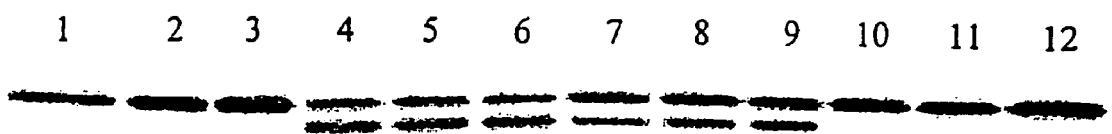
FIG. 2. Cleavage of SNAP-25 by ExL-$LH_N$/A

The extracted protein samples were applied to 4-20% polyacrylamide gradient gels and subjected to electrophoresis prior to transfer to nitrocellulose. Proteolysis of SNAP-25, a crucial component of the neurosecretory process and the substrate for the zinc-dependent endopeptidase activity of BoNT/A, was then detected by probing with an antibody (SMI-81) that recognizes both the intact and cleaved forms of SNAP-25 (FIG. 2). Proteins blotted onto nitrocellulose were probed with antibody SMI-81. Lanes 1-3, 4-6, 7-9 and 10-12 represent cells treated with medium, 40 microgrammes/ml ExL, 20 microgrammes/ml ExL and 40 microgrammes/ml $LH_N/A$ respectively. Densitometric analysis of these data determined the % SNAP-25 cleavage to be 52.7% and 37.0% for 40 and 20 microgrammes/ml respectively.

EXAMPLE 5

Activity of SBA-$LH_N$/A in Primary Neuronal Cultures

Figure 7:
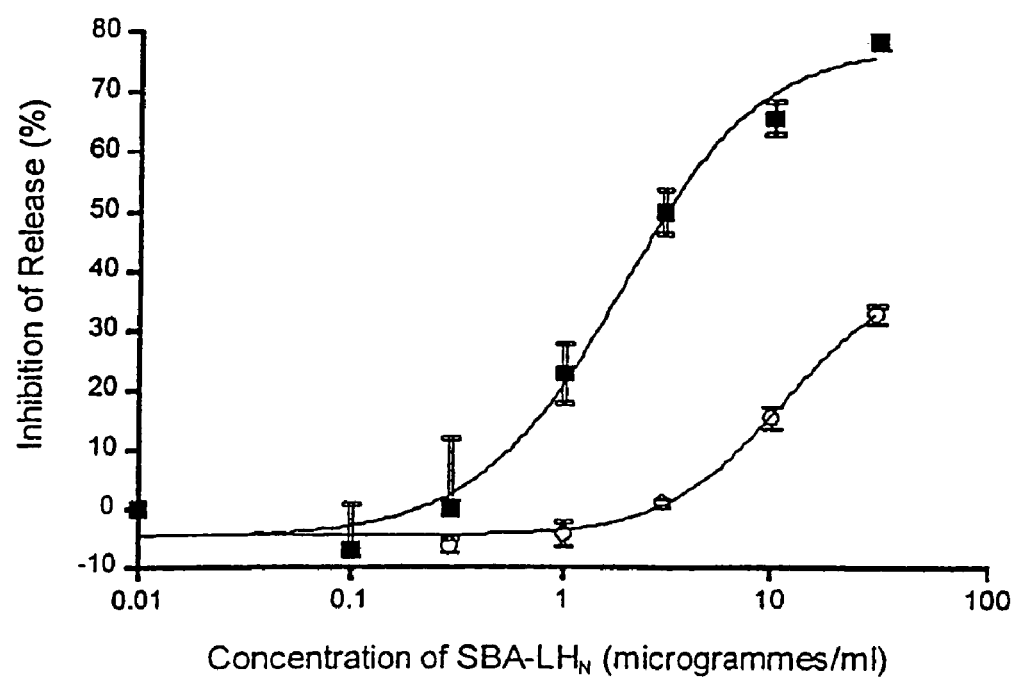

Using methodology described in Example 4, the activity of SBA-$LH_N$/A in primary neuronal cultures was assessed. The selectivity of the SBA-$LH_N$/A conjugate for eDRG over eSC neurons is illustrated in FIG. 7. Both eDRG and eSC cultures were exposed to a range of SBA-$LH_N$/A concentrations (1 ml volumes) for three days. The percentage inhibition of eDRG substance P (n) and eSC ($^3$H)-glycine (O) release is in comparison to untreated controls. The data is the mean of three determinations±SE. The curves shown are representative of two experiments. $IC_{50}$ values for eDRG neurons were determined to be 1.84 and 7.6 microgrammes/ml. It is observed that SBA-$LH_N$/A exhibits a clear selectivity of the inhibition of neurotransmitter release from eDRG relative to eSC neurons. These data therefore confirm observations described for ExL-$LH_N$/A above and highlight the properties of galactose-specific lectins.

EXAMPLE 6

Activity of WGA-$LH_N$/A in Primary Neuronal Cultures

Using methodology described in Example 4, the activity of WGA-$LH_N$/A in primary neuronal cultures was assessed. WGA represents an example of a non-galactosyl targeted lectin and therefore serves as an indicator of the properties of conjugate that do not recognize galactosyl moieties. The lack of selectivity of the WGA-$LH_N$/A conjugate for eDRG over eSC neurons is illustrated in FIG. 8. eDRG and eSC neurons were exposed to a range of concentrations of WGA-$LH_N$/A for 3 days prior to assay of stimulated release of neurotransmitter (substance P and glycine respectively). Each conjugate concentration was assessed in triplicate and results are expressed as percentage inhibition compared to untreated controls. Panels A and B represent dose response curves from one experiment representative of ≧3 for eDRG and eSC neurons respectively. Each point shown is the mean of three determinations±SE of the mean. $IC_{50}$ data for the effects of WGA-$LH_N$/A was calculated to be 0.34±0.06 microgrammes/ml (eDRG) and 0.06±0.09 microgrammes/ml (eSC), indicating the lack of C-fiber selectivity.

EXAMPLE 7

Activity of ExL-$LH_N$/A in an Electrophysiological Model of Pain

A dose of 45 microgrammes of ExL-$LH_N$/A in a 10 microliters volume of vehicle was given by intrathecal injection to rats between lumbar sections L4-L5, 24 hours prior to electrophysiological analysis of neuronal activity. Animals were allowed to recover and movement was not restricted prior to sacrifice and analysis. The results from a group of 3 animals with 10 neurons recorded per animal, show that there was a 73% reduction in the C-fiber responses of the neurones (FIG. 9A) although the stimulus threshold is only slightly elevated (FIG. 9B). Inhibition of C-fiber responses would lead to a decrease in the transmission of pain signals and these data are indicative of the analgesic effect of conjugate ExL-$LH_N$/A. There was also a significant decrease in the $A_\delta$ response (FIG. 9C). These fibers are also implicated in the transmission of noxious stimuli and this result emphasizes the analgesic effect of ExL-$LH_N$/A. $A_\beta$ neurons, a cell type that is not involved in transmission of noxious stimuli, were essentially unaltered in their responses to this stimulus (FIG. 9D). The lack of affect on the $A_\beta$-fiber neurons is indicative of the selectivity of ExL-$LH_N$/A for the neurons central to the transmission of pain signals.

EXAMPLE 8

Activity of ExL-$LH_N$/A in Behavioral Models of Pain

Figure 10:
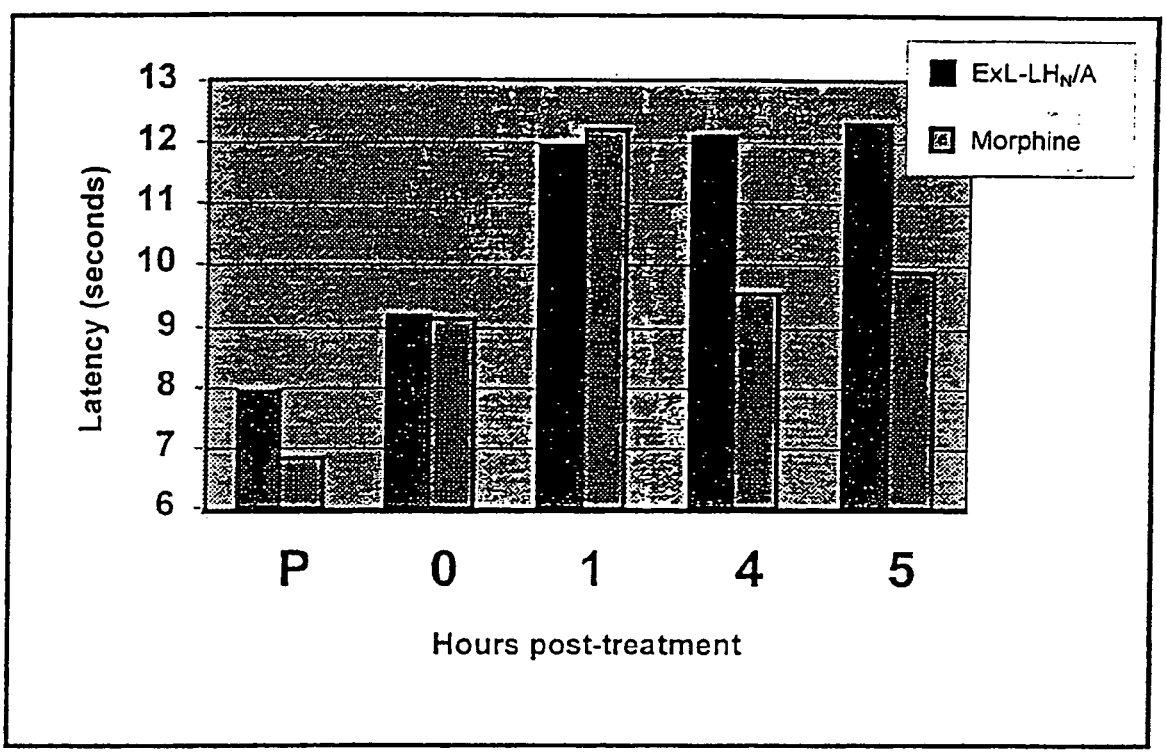
FIG. 10. Activity of ExL-$LH_N$/A in an in vivo behavioral model of analgesia.

In an accepted in vivo model of pain, the mouse hotplate test, ExL-$LH_N$/A has been demonstrated to exhibit analgesic properties. FIG. 10 illustrates the data obtained for ExL-$LH_N$/A where it is compared to a supramaximal dose of morphine. ExL-$LH_N$/A was applied intrathecally (30 microgrammes in a 5 microliter vehicle volume) to each of a group of 10 mice and analgesic response in the hot plate test determined. Data is presented as hot plate latency (seconds) plotted against assay time (P=pre-treatment, 0-5=hours post application). Onset of ExL-$LH_N$/A action had apparently reached a plateau at 1 hour that remained constant for at least 5 hours. The level of analgesia is similar to a supramaximal dose (50 microgrammes, 20× mouse $EC_{50}$) of morphine in this test, but is of much longer duration. This level of morphine achieves a maximal effect at 1 hour and then returns to control levels over a period of 5 hours. These data represent a clear indication of the analgesic potential of agents such as ExL-$LH_N$/A.

Materials

Adult outbred mice (MF1) of either sex, weight range 20 to 30 g.

Methods

Test material is injected into the intrathecal space of anaesthetized mice using a 30 gauge disposable needle attached to a 50 microliter Hamilton syringe. The site of injection was normally chosen to be between lumbar vertebrae 5 and 6. The needle is inserted into the tissue to one side of the vertebrae so that it slips into the groove between the spinous and transverse processes. The needle is then moved carefully forward to the intervertebral space. 5 micro liters of test material is then injected into the intrathecal space and the needle withdrawn. The skin incision is then closed with a single wound clip and the animal placed in a box to allow recovery.

EXAMPLE 9

Isolation of the Gene for *Erythrina cristagalli* Lectin (ECL)

The gene encoding *Erythrina cristagalli* lectin (ECL) was isolated as described in Stancombe et al 2003, Protein Expression & Purification, 30, 283-292. Briefly, *E. cristagalli* seeds (supplied by Sandeman Seeds) were germinated to obtain leaf material from the saplings, from which genomic DNA was prepared. Total genomic DNA was isolated and purified from leaf material using a plant DNeasy miniprep kit (Promega Corp.). PCR was performed using High Fidelity Taq polymerase (Roche Diagnostics Corp) according to the manufacturer's instructions. The full ECL sequence was amplified using 100 ng of genomic DNA as the template and the primers 5'-GTGGAAACCATATCGTTTAG-3' (SEQ ID 36) and 5'-GTAGGAATAACAGCATCGTTTG-3' (SEQ ID 37) in a Techne Genius thermal cycler. The PCR products were cloned into the pCR2.1 vector (Invitrogen Corp) and transformed into *E. coli* TOP10 cells to create clone pCR ECL. The complete DNA sequence of the ECL coding region was submitted to GenBank (AY158072) and is described in SEQ ID 1.

EXAMPLE 10

Creation of an *Erythrina cristagalli* Lectin-LH$_N$/A (ECL-LH$_N$/A) Expression Clone The LH$_N$/A amino acid sequence, obtained from freely available database sources such as GenBank (accession number P10845) or Swissprot (accession locus BXA1_CLOBO), was altered so the LC-H$_N$/A linker (in this case defined as the inter-domain polypeptide region that exists between the cysteines of the disulphide bridge between LC and H$_N$) included the recognition sequence for Factor Xa for specific protease activation. Using Backtranslation tool v2.0 (Entelechon), the DNA sequence encoding the modified LH$_N$/A was determined. A BamHI recognition sequence was incorporated at the 5' end and XbaI plus HindIII recognition sequences were incorporated at the 3' end of the LH$_N$/A. Two stop codons inserted between the XbaI and HindIII sites for efficient translation termination. Two further restriction sites, SalI and PstI, were inserted to flank the linker region. The DNA sequence was screened using MapDraw, (DNASTAR Inc.) for restriction enzyme cleavage sequences incorporated during the back translation. Any cleavage sequences that are found to be common to those required for cloning were removed manually from the proposed coding sequence ensuring common *E. coli* codon usage is maintained. *E. coli* codon usage was assessed Graphical Codon Usage Analyser (Geneart), and the % GC content and codon usage ratio assessed by reference to published codon usage tables. This optimised DNA sequence (SEQ ID 2) containing the LH$_N$/A open reading frame (ORF) was then commercially synthesized.

The DNA encoding mature ECL was amplified from the cloned pCR ECL (SEQ ID 1) using oligonucleotides incorporating XbaI and HindIII recognition sequences at the 5' and 3' ends respectively. The 5' oligonucleotide also encodes a glycine/serine flexible spacer region between the XbaI site and the ECL gene and the 3' oligonucleotide also contains two stop codons just before the HindIII site for efficient translation termination. The resulting PCR product is depicted in SEQ ID 3.

The LH$_N$/A was inserted into the pMAL (NEB) expression vector using the BamHI and HindIII restriction enzymes. The spacer-ECL was then inserted into the pMAL-LH$_N$/A DNA using the XbaI and HindIII restriction enzymes. The resultant construct is the final ECL-LH$_N$/A fusion product in the pMAL expression vector (SEQ ID 4 and SEQ ID 5)

EXAMPLE 11

Expression & Purification of ECL-LH$_N$/A

The pMAL expression vector expressing ECL-LH$_N$/A was transformed into *E. coli* HMS174 or AD494(DE3) (Novagen). Cultures were grown in Terrific broth complex medium supplemented with ZnCl$_2$ (1 µM), ampicillin (100 µg/ml), 0.2% (w/v) glucose. Parameters for expression of the constructs were initially determined in shake flask cultures. Pre-induction bacterial growth was maintained at 37° C. to an OD600 nm of 0.5, at which stage expression of ECL-LH$_N$/A was induced by addition of IPTG to 0.5 mM and a reduction in temperature to 30° C. After 4 h at 30° C. the bacteria were harvested by centrifugation and the resulting paste was stored at −70° C.

Typically, 16 g of cell paste was suspended in 160 ml PBS and lysed by sonication (MSE Soniprep 150). The resulting lysate was clarified by centrifugation prior loading onto a 25 ml amylose column and eluted with 10 mM maltose in PBS. The eluant contained approximately 50% pure fusion protein and was treated with Factor Xa (1 U Factor Xa/100 µg fusion protein; 20 h; 26° C.) to remove the maltose binding protein fusion partner and cleave the LC-H$_N$ junction to activate the protein. After incubation, the sample was filtered (0.45 µm) and diluted twofold with water to give a 0.5×PBS buffer composition. The cleaved, filtered, and diluted ECL-LH$_N$/A was processed through a Q-Sepharose FF column (10 ml) and eluted within a 0-500 mM NaCl gradient.

See FIG. 12 for an illustration of the purified soluble LH$_N$/A-ECL and its activation by treatment with protease.

EXAMPLE 12

Creation of an *Erythrina cristagalli* Lectin-LH$_N$/C (ECL-LH$_N$/C) Expression Clone The LH$_N$/C amino acid sequence obtained from freely available database sources such as GenBank (accession number X62389) was synthesised maintaining the native Factor Xa activation site within the linker region (SEQ ID 6) using the methods described in example 2. The spacer-ECL was also created using the method described in example 2 but with an alternative helical spacer region incorporated during PCR amplification (SEQ ID 7). The two genes were then subcloned into the PMAL expression vector using BamHI, XbaI and HindIII restriction enzymes to create ECL-LH$_N$/C (SEQ ID 8 and SEQ ID 9).

EXAMPLE 13

Expression, Purification and Characterisation of ECL-LH$_N$/C

The pMAL expression vector expressing ECL-LH$_N$/C was transformed into *E. coli* HMS174 or AD494(DE3) (Novagen). Cultures were grown in Terrific broth complex medium supplemented with ZnCl$_2$ (1 µM), ampicillin (100 µg/ml), 0.2% (w/v) glucose. Parameters for expression of the constructs were initially determined in shake flask cultures. Pre-induction bacterial growth was maintained at 37° C. to an OD600 nm of 0.5, at which stage expression of ECL-LH$_N$/C was induced by addition of IPTG to 0.5 mM and a reduction in temperature to 30° C. After 4 h at 30° C. the bacteria were harvested by centrifugation and the resulting paste was stored at −70° C.

Typically, 16 g of cell paste was suspended in 160 ml PBS and lysed by sonication (MSE Soniprep 150). The resulting lysate was clarified by centrifugation prior loading onto a 25 ml amylose column and eluted with 10 mM maltose in PBS. Taking advantage of the native Factor Xa protease recognition sequence in the $LH_N/C$ activation loop, the eluant was treated with Factor Xa (1 U Factor Xa/100 µg fusion protein; 20 h; 26° C.) to remove the maltose binding protein fusion partner and cleave the LC-$H_N$ junction to activate the protein. After incubation, the sample was filtered (0.45 µm) and diluted twofold with water to give a 0.5×PBS buffer composition. The cleaved, filtered, and diluted ECL-$LH_N/C$ was processed through a Q-Sepharose FF column (10 ml) and eluted within a 0-500 mM NaCl gradient.

See FIG. 11 for an illustration of the purified soluble $LH_N$/C-ECL and its activation by treatment with protease.

EXAMPLE 14

Creation of an *Erythrina corallodendron* Lectin-$LH_N/A$ (ECorL-$LH_N/A$) Expression Clone The ECorL amino acid sequence, obtained from freely available database sources such as GenBank (accession number CAA36986), was modified for *E. coli* expression by removal of amino acids at the N and C terminus of the ECorL precursor before back translation using Backtranslation tool v2.0 (Entelechon). The DNA sequence was further modified to incorporate XbaI and HindIII recognition sequences at the 5' and 3' ends respectively. Between the XbaI site and the ECorL gene, a glycine/serine flexible spacer region was added and after the ECorL gene, but before the HindIII site, two stop codons were also included. The DNA sequence was screened using MapDraw, (DNASTAR Inc.) for restriction enzyme cleavage sequences incorporated during the back translation. Any cleavage sequences that were found to be common to those required for cloning were removed manually from the proposed coding sequence ensuring common *E. coli* codon usage was maintained. *E. coli* codon usage was assessed Graphical Codon Usage Analyser (Geneart), and the % GC content and codon usage ratio assessed by reference to published codon usage tables. This optimised DNA sequence (SEQ ID 10) containing the ECorL ORF was then commercially synthesized.

The ECorL (SEQ ID10) and the $LH_N/A$ (SEQ ID2) synthetic genes were sub-cloned into the pMAL expression vector using BamHI, XbaI and HindIII restriction enzymes to create ECorL-$LH_N/C$ (SEQ ID 11 and SEQ ID 12).

EXAMPLE 15

Creation of a Soybean Agglutinin-$LH_N/C$ (SBA-$LH_N/C$) Expression Clone

The SBA amino acid sequence, obtained from freely available database sources such as GenBank (accession number P05046), was modified for *E. coli* expression by removal of N terminal signal sequence before back translation using Backtranslation tool v2.0 (Entelechon). The DNA sequence was modified to incorporate XbaI and HindIII recognition sequences at the 5' and 3' ends respectively. Between the XbaI site and the SBA gene a glycine/serine flexible spacer region was added and after the SBA gene, but before the HindIII, site two stop codons were also included. The DNA sequence was screened using MapDraw, (DNASTAR Inc.) for restriction enzyme cleavage sequences incorporated during the back translation. Any cleavage sequences that are found to be common to those required for cloning were removed manually from the proposed coding sequence ensuring common *E. coli* codon usage is maintained. *E. coli* codon usage was assessed Graphical Codon Usage Analyser (Geneart), and the % GC content and codon usage ratio assessed by reference to published codon usage tables. This optimised DNA sequence (SEQ ID 13) containing the SBA ORF was then commercially synthesized.

The SBA (SEQ ID 13) and the $LH_N/C$ (SEQ ID 6) synthetic genes were sub-cloned into the pMAL expression vector using BamHI, XbaI and HindIII restriction enzymes to create SBA-$LH_N/C$ (SEQ ID 14 and SEQ ID 15).

EXAMPLE 16

Creation of a *Pseudomonas aeruginosa*-$LH_N/A$ (PA-1-$LH_N/A$) Expression Clone The PA-I amino acid sequence, obtained from freely available database sources such as GenBank (accession number X65933), was back translated using Backtranslation tool v2.0 (Entelechon). The DNA sequence was modified to incorporate XbaI and HindIII recognition sequences at the 5' and 3' ends respectively. Between the XbaI site and the PA-I gene a glycine/serine flexible spacer region was added and after the PA-I gene but before the HindIII, site two stop codons were also included. The DNA sequence was screened using MapDraw, (DNASTAR Inc.) for restriction enzyme cleavage sequences incorporated during the back translation. Any cleavage sequences that are found to be common to those required for cloning were removed manually from the proposed coding sequence ensuring common *E. coli* codon usage is maintained. *E. coli* codon usage was assessed Graphical Codon Usage Analyser (Geneart), and the % GC content and codon usage ratio assessed by reference to published codon usage tables. This optimised DNA sequence (SEQ ID 16) containing the PA-I ORF was then commercially synthesized.

The PA-I (SEQ ID 16) and the $LH_N/A$ (SEQ ID 2) synthetic genes were sub-cloned into the pMAL expression vector using BamHI, XbaI and HindIII restriction enzymes to create PA-I-$LH_N/A$ (SEQ ID 17 and SEQ ID 18).

EXAMPLE 17

Creation of an *Erythrina cristagalli* lectin-LC/A-DT (ECL-LC/A-DT) Expression Clone The $LH_N/A$ and DT amino acid sequence, obtained from freely available database sources such as GenBank (accession numbers P10845 and 1×DTT respectively). The diphtheria toxin (DT) translocation domain (domain T) is known in the art to effect translocation of cargo proteins from an acidified endosomal compartment to the cytosol. To create a clostridial endopeptidase—DT-T—lectin hybrid, amino acids 202-378 of diphtheria toxin (INLDW . . . SYNRP) (SEQ ID 38) were identified as the suitable fragment for insertion to the C-terminus of the LC/A. To maintain the proximity of the cysteines within the DT protease sensitive loop (essential for disulphide bonding), the DT loop sequence was also utilized between the LC and the DT-T. This effectively led to a truncation of the LC/A sequence after the C-terminal cysteine. In order that cleavage of the loop was specifically achieved, the sequence of the DT protease loop was modified to incorporate a Factor Xa recognition sequence. The resultant junction (italicized) took the form of LC/A-CAGNIEGRSVGSSLSC-DT-T (SEQ ID 39). This hybrid amino acid sequence was back translated using the Backtranslation tool v2.0 (Entelechon). A BamHI recognition sequence was incorporated at the 5' end and XbaI plus HindIII recognition sequences were incorporated at the 3' end of the gene. Two stop codons inserted between the XbaI and HindIII sites for efficient translation termination. The DNA sequence was screened using MapDraw, (DNASTAR Inc.) for restriction enzyme cleavage sequences incorporated during the back translation. Any cleavage sequences that are found to be common to those required for cloning were removed manually from the proposed coding sequence ensuring common $E.$ $coli$ codon usage is maintained. $E.$ $coli$ codon usage was assessed Graphical Codon Usage Analyser (Geneart), and the % GC content and codon usage ratio assessed by reference to published codon usage tables. This optimised DNA sequence (SEQ ID 19) containing the LC/A-DT-T open reading frame (ORF) was then commercially synthesized.

The LC/A-DT (SEQ ID 19) was inserted into the pMAL expression vector using the BamHI and HindIII restriction enzymes. The spacer-ECL (SEQ ID 3) was then inserted into the pMAL-LC/A-DT DNA using the XbaI and HindIII restriction enzymes. The resultant construct is the final ECL-LC/A-DT fusion product in the pMAL expression vector (SEQ ID 20 and SEQ ID 21)

EXAMPLE 18

Creation of an *Erythrina cristagalli* Lectin-LC/A-$H_N$/C (ECL-LC/A-$H_N$/C) Expression Clone By taking the ECL-$LH_N$/A (SEQ ID 4) and the synthesised $LH_N$/C (SEQ ID 6) and digesting both with PstI and XbaI the $H_N$ regions have been switched to create the hybrid ECL-LC/A-$H_N$/C in the pMAL expression vector (SEQ ID 22 and SEQ ID 23).

EXAMPLE 19

Creation of an *Erythrina cristagalli* Lectin-IgA protease-HN/A (ECL-IgA-HN) Expression Clone The IgA protease and $LH_N$/A amino acid sequences were obtained from freely available database sources such as GenBank (accession number P09790 and P10845 respectively). Information regarding the structure of the *N. Gonorrhoeae* IgA protease gene is available in the literature (Pohlner et al., Gene structure and extracellular secretion of *Neisseria gonorrhoeae* IgA protease, Nature. 1987, 325(6103), 458-62). A hybrid amino acid sequence was created by fusing the IgA protease to the $H_N$/A translocation domain. The proximity of the cysteines within the original $LH_N$/A endopeptidase was maintained by engineering the IgA onto the N-terminus of the clostridial activation loop in place of the LC domain. Within the activation loop the recognition sequence for Factor Xa was incorporated to allow specific protease activation. Using Backtranslation tool v2.0 (Entelechon), the DNA sequence encoding the IgA-$H_N$/A fusion modified for $E.$ $coli$ expression as determined. A BamHI recognition sequence was incorporated at the 5' end and XbaI plus HindIII recognition sequences were incorporated at the 3' end of the IgA-$H_N$/A. Two stop codons were inserted between the XbaI and HindIII sites for efficient translation termination. Two further restriction sites, SalI and PstI, were inserted to flank the linker region between the cysteines. The DNA sequence was screened using MapDraw, (DNASTAR Inc.) for restriction enzyme cleavage sequences incorporated during the back translation. Any cleavage sequences that are found to be common to those required for cloning were removed manually from the proposed coding sequence ensuring common $E.$ $coli$ codon usage is maintained. $E.$ $coli$ codon usage was assessed Graphical Codon Usage Analyser (Geneart), and the % GC content and codon usage ratio assessed by reference to published codon usage tables. This optimised DNA sequence (SEQ ID 24) containing the IgA-$H_N$/A open reading frame (ORF) was then commercially synthesized.

The IgA-$H_N$/A (SEQ ID24) was inserted into the pMAL expression vector using the BamHI and HindIII restriction enzymes. The spacer-ECL (SEQ ID 3) was then inserted into the pMAL-IgA-$H_N$/A DNA using the XbaI and HindIII restriction enzymes. The resultant construct is the final ECL-IgA-HN/A fusion product in the pMAL expression vector (SEQ ID 25 and SEQ ID 26).

EXAMPLE 20

Creation of a Soybean Agglutinin-LC/A-influenza Haemagglutinin (SBA-LC/A-HA) Expression Clone The influenza haemagglutinin polypeptide (HA) amino acid sequence is obtained from freely available database sources such as GenBank (accession numbers NP_040980 respectively). Information regarding the structure of the influenza haemagglutinin gene, and a description of the HA1 and HA2 domain structure, is available in the literature (Winter, G. et al., Nucleotide sequence of the haemagglutinin gene of a human influenza virus H1 subtype, Nature 292 (5818), 72-75 (1981)). To create a clostridial endopeptidase-HA2-lectin hybrid, amino acids 345-566 of influenza haemagglutinin (GLFG . . . RICI) (SEQ ID 40) were identified as the suitable fragment for insertion to the C-terminus of the LC/A. To maintain the proximity of the cysteines within the original $LH_N$/A endopeptidase, the HA sequence was engineered onto the C-terminus of the clostridial activation loop in place of the $H_N$ domain. Within the activation loop the recognition sequence for Factor Xa was incorporated to allow specific protease activation. This hybrid amino acid sequence was back translated using the Backtranslation tool v2.0 (Entelechon). Using Backtranslation tool v2.0 (Entelechon), the DNA sequence encoding the LC/A-HA fusion modified for $E.$ $coli$ expression was determined. A BamHI recognition sequence was incorporated at the 5' end and XbaI plus HindIII recognition sequences were incorporated at the 3' end of the LC/A-HA. Two stop codons were inserted between the XbaI and HindIII sites for efficient translation termination. Two further restriction sites, SalI and PstI, were inserted to flank the linker region between the cysteines. The DNA sequence was screened using MapDraw, (DNASTAR Inc.) for restriction enzyme cleavage sequences incorporated during the back translation. Any cleavage sequences that are found to be common to those required for cloning were removed manually from the proposed coding sequence ensuring common $E.$ $coli$ codon usage is maintained. $E.$ $coli$ codon usage was assessed Graphical Codon Usage Analyser (Geneart), and the % GC content and codon usage ratio assessed by reference to published codon usage tables. This optimised DNA sequence (SEQ ID 27) containing the LC/A-HA open reading frame (ORF) was then commercially synthesized.

The LC/A-HA (SEQ ID27) was inserted into the pMAL expression vector using the BamHI and HindIII restriction enzymes. The spacer-SBA (SEQ ID 13) was then inserted into the pMAL-LC/A-HA DNA using the XbaI and HindIII restriction enzymes. The resultant construct is the final SBA-LC/A-HA fusion product in the pMAL expression vector (SEQ ID 28 and SEQ ID 29.

EXAMPLE 21

Creation of an *Erythrina cristagalli* Lectin-LH$_N$/B (ECL-LH$_N$/B) Expression Clone The LH$_N$/B amino acid sequence obtained from freely available database sources such as GenBank (accession number P10844) was synthesised with a modified linker region including an Enterokinase activation site (SEQ ID 30) using the methods described in Example 2. The spacer-ECL was also created using the method described in Example 2 (SEQ ID 3). The LH$_N$/B was inserted into the pMAL (NEB) expression vector using the BamHI and HindIII restriction enzymes. The spacer-ECL was then inserted into the pMAL-LH$_N$/B DNA using the XbaI and HindIII restriction enzymes. The resultant construct is the final ECL-LH$_N$/B fusion product in the pMAL expression vector (SEQ ID 31 and SEQ ID 32).

EXAMPLE 22

Expression, Purification and Characterisation of ECL-LH$_N$/B

The pMAL expression vector expressing ECL-LH$_N$/B was transformed into *E. coli* HMS174 or AD494(DE3) (Novagen). Cultures were grown in Terrific broth complex medium supplemented with ZnCl$_2$ (1 μM), ampicillin (100 μg/ml), 0.2% (w/v) glucose. Parameters for expression of the constructs were initially determined in shake flask cultures. Pre-induction bacterial growth was maintained at 37° C. to an OD600 nm of 0.5, at which stage expression of ECL-LH$_N$/B was induced by addition of IPTG to 0.5 mM and a reduction in temperature to 30° C. After 4 h at 30° C. the bacteria were harvested by centrifugation and the resulting paste was stored at −70° C.

Typically, 16 g of cell paste was suspended in 160 ml PBS and lysed by sonication (MSE Soniprep 150). The resulting lysate was clarified by centrifugation prior loading onto a 25 ml amylose column and eluted with 10 mM maltose in PBS. The eluant was treated with Factor Xa (1 U Factor Xa/100 μg fusion protein) and Enterokinase (0.00064 μg Enterokinase/100 μg fusion protein) for 20 hours at 26° C. to remove the maltose binding protein fusion partner and cleave the LC-H$_N$ junction to activate the protein. After incubation, the sample was filtered (0.45 μm) and diluted twofold with water to give a 0.5×PBS buffer composition. The cleaved, filtered, and diluted ECL-LH$_N$/B was processed through a Q-Sepharose FF column (10 ml) and eluted within a 0-500 mM NaCl gradient.

See FIG. 13 for an illustration of the purified soluble ECL-LH$_N$/B and its activation by treatment with protease.

SEQ ID NOs:
SEQ ID 1 PCR amplified DNA sequence of ECL
SEQ ID 2 Synthesised DNA sequence of LH$_N$/A with Factor Xa activation site
SEQ ID 3 PCR amplified DNA sequence of GSspacer-ECL
SEQ ID 4 DNA sequence of ORF from pMAL-LH$_N$/A-GSspacer-ECL
SEQ ID 5 Protein sequence of ORF from pMAL-LH$_N$/A-GSspacer-ECL
SEQ ID 6 Synthesised DNA sequence of LH$_N$/C
SEQ ID 7 PCR amplified DNA sequence of HXspacer-ECL
SEQ ID 8 DNA sequence of ORF from pMAL-LH$_N$/C-HXspacer-ECL
SEQ ID 9 Protein sequence of ORF from pMAL-LH$_N$/C-HXspacer-ECL
SEQ ID 10 Synthesised DNA sequence of GSspacer-ECorL
SEQ ID 11 DNA sequence of ORF from pMAL-LH$_N$/A-GSspacer-ECorL
SEQ ID 12 Protein sequence of ORF from pMAL-LH$_N$/A-GSspacer-ECorL
SEQ ID 13 Synthesised DNA sequence of GSspacer-SBA
SEQ ID 14 DNA sequence of ORF from pMAL-LH$_N$/C-GSspacer-SBA
SEQ ID 15 Protein sequence of ORF from pMAL-LH$_N$/C-GSspacer-SBA
SEQ ID 16 Synthesised DNA sequence of GSspacer-PA-I
SEQ ID 17 DNA sequence of ORF from pMAL-LH$_N$/A-GSspacer-PA-I
SEQ ID 18 Protein sequence of ORF from pMAL-LH$_N$/A-GSspacer-PA-I
SEQ ID 19 Synthesised DNA sequence of LC/A-DT with a Factor Xa activation site
SEQ ID 20 DNA sequence of ORF from pMAL-LC/A-DT-GSspacer-ECL
SEQ ID 21 Protein sequence of ORF from pMAL-LC/A-DT-GSspacer-ECL
SEQ ID 22 DNA sequence of ORF from pMAL-LC/A-H$_N$/C-GSspacer-ECL
SEQ ID 23 Protein sequence of ORF from pMAL-LC/A-H$_N$/C-GSspacer-ECL
SEQ ID 24 Synthesised DNA sequence of IgA-H$_N$/A with Factor Xa activation site
SEQ ID 25 DNA sequence of ORF from pMAL-IgA-H$_N$/A-GSspacer-ECL
SEQ ID 26 Protein sequence of ORF from pMAL-IgA-H$_N$/A-GSspacer-ECL
SEQ ID 27 Synthesised DNA sequence of LC/A-HA with Factor Xa activation site
SEQ ID 28 DNA sequence of ORF from pMAL-LC/A-HA-GSspacer-SBA
SEQ ID 29 Protein sequence of ORF from pMAL-LC/A-HA-GSspacer-SBA
SEQ ID 30 Synthesised DNA sequence of LH$_N$/B with Enterokinase activation site
SEQ ID 31 DNA sequence of ORF from pMAL-LH$_N$/B-GSspacer-ECL
SEQ ID 32 Protein sequence of ORF from pMAL-LH$_N$/B-GSspacer-ECL
SEQ ID 33 Protein sequence of *Pseudomonas aeruginosa* PA-I lectin
SEQ ID 34 Protein sequence of Soybean agglutinin (SBA) (modified to remove the signal sequence)
SEQ ID 35 Protein sequence of *Erythrina corallodendron* lectin (ECorL) (modified to remove the signal sequence)
SEQ ID 36 Primer sequence of ECL
SEQ ID 37 Primer sequence of ECL
SEQ ID 38 Amino acids 202-378 of diphtheria toxin (DT)
SEQ ID 39 Amino acid sequence of the DT protease loop
SEQ ID 40 Amino acids 345-566 of influenza haemagglutinin

The invention claimed is:

1. An agent for the treatment of pain, wherein the agent has been obtained in the form of a fusion protein by a method comprising expressing in a host cell a genetic construct that codes for the agent, said agent comprising: a galactose-binding lectin; an L-chain of a clostridial neurotoxin or a fragment thereof that cleaves vesicle and/or plasma membrane associated proteins involved in the exocytic process; and a translocating domain of a clostridial neurotoxin H-chain that translocates the L-chain or L-chain fragment into a target cell, wherein the agent is a fusion protein.

2. An agent according to claim 1, wherein the galactose-binding lectin is selected from the group consisting of *Erythrina cristagalli* lectin, *Erythrina corallodendron* lectin, soybean agglutinin, *Arachis hypogaea* lectin, *Bandeirea simplicfolia* lectin and *Pseudomonas aeringuosa* lectin.

3. An agent for the treatment of pain, wherein the agent has been obtained in the form of a fusion protein by a method comprising expressing in a host cell a genetic construct that codes for the agent, said agent comprising: a galactose-binding lectin; an L-chain of a clostridial neurotoxin or a fragment thereof that cleaves vesicle and/or plasma membrane associated proteins involved in the exocytic process; and a translocating domain of a diphtheria toxin that translocates the L-chain or L-chain fragment into a target cell, wherein the agent is a fusion protein.

4. An agent according to claim 3, wherein the galactose-binding lectin is selected from the group consisting of *Erythrina cristagalli* lectin, *Erythrina corallodendron* lectin, soybean agglutinin, *Arachis hypogaea* lectin, *Bandeirea simplicifolia* lectin and *Pseudomonas aeringuosa* lectin.

5. An agent for the treatment of pain, wherein the agent has been obtained in the form of a fusion protein by a method comprising expressing in a host cell a genetic construct that codes for the agent, said agent comprising: a galactose-binding lectin; an IgA protease of *Neisseria gonorrhoeae* that cleaves vesicle and/or plasma membrane associated proteins involved in the exocytic process; and a translocating domain of a clostridial neurotoxin H-chain that translocates the IgA protease into a target cell, wherein the agent is a fusion protein.

6. An agent according to claim 5, wherein the galactose-binding lectin is selected from the group consisting of *Erythrina cristagalli* lectin, *Erythrina corallodendron* lectin, soybean agglutinin, *Arachis hypogaea* lectin, *Bandeirea simplicifolia* lectin and *Pseudomonas aeringuosa* lectin.

7. An agent for the treatment of pain, wherein the agent has been obtained in the form of a fusion protein by a method comprising expressing in a host cell a genetic construct that codes for the agent, said agent comprising: a galactose-binding lectin; an IgA protease of *Neisseria gonorrhoeae* that cleaves vesicle and/or plasma membrane associated proteins involved in the exocytic process; and a translocating domain of a diphtheria toxin that translocates the IgA protease into a target cell, wherein the agent is a fusion protein.

8. An agent according to claim 7, wherein the galactose-binding lectin is selected from the group consisting of *Erythrina cristagalli* lectin, *Erythrina corallodendron* lectin, soybean agglutinin, *Arachis hypogaea* lectin, *Bandeirea simplicifolia* lectin and *Pseudomonas aeringuosa* lectin.

* * * * *